United States Patent
Hasegawa et al.

(10) Patent No.: US 6,309,561 B1
(45) Date of Patent: *Oct. 30, 2001

(54) LIQUID CRYSTAL COMPOUNDS HAVING A CHIRAL FLUORINATED TERMINAL PORTION

(75) Inventors: Masakazu Hasegawa, Hachioji (JP); Michael P. Keyes, Minneapolis, MN (US); Marc D. Radcliffe, Newport, MN (US); Patricia M. Savu, Maplewood, MN (US); Daniel C. Snustad, Woodbury, MN (US); Terence D. Spawn, West Lakeland Township, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/998,400

(22) Filed: Dec. 24, 1997

(51) Int. Cl.$^7$ ............ C09K 19/34; C09K 19/32; C07C 25/13; C07D 239/02; C07D 319/12; C07D 263/02

(52) U.S. Cl. ............ 252/299.61; 252/299.62; 252/299.63; 544/303; 546/346; 548/215; 549/324; 549/380; 568/634; 568/649; 568/669; 570/128; 570/130; 570/131; 570/132; 570/144; 570/183; 570/188

(58) Field of Search ............ 252/299.01, 299.61, 252/299.62, 299.63, 299.65, 299.66, 299.67; 544/303; 546/346; 549/324, 380; 548/215; 568/634, 649, 669; 570/128, 130, 131, 132, 144, 183, 188; 560/65

(56) References Cited

U.S. PATENT DOCUMENTS

| | | | |
|---|---|---|---|
| 2,519,983 | 8/1950 | Simons | 204/62 |
| 3,470,258 | 9/1969 | Tesoro | 260/615 |
| 4,001,137 | 1/1977 | Steinstrasser | 252/299 |

(List continued on next page.)

FOREIGN PATENT DOCUMENTS

| | | | |
|---|---|---|---|
| 33 32 692 | 3/1985 | (DE) | C07C/121/46 |
| 40 34 123 | 4/1992 | (DE) | C07C/19/08 |
| 43 08 028 | 9/1994 | (DE) | C07C/43/225 |
| 44 44 701 | 6/1995 | (DE) | C07D/239/34 |
| 0 047 877 | 3/1982 | (EP) | C07C/103/375 |
| 0 163 229 | 12/1985 | (EP) | C09K/19/02 |
| 0 181 601 | 5/1986 | (EP) | C09K/19/60 |
| 0 255 236 | 2/1988 | (EP) | C09K/19/20 |
| 0 301 511 | 2/1989 | (EP) | C07C/69/76 |
| 0 331 367 | 9/1989 | (EP) | C09K/19/20 |
| 0 332 025 | 9/1989 | (EP) | C07C/121/407 |
| 0 434 297 | 6/1991 | (EP) | C07D/239/26 |
| 0 499 221 | 8/1992 | (EP) | C07D/239/26 |
| 0 548 548 | 6/1993 | (EP) | G02F/1/137 |
| 0 641 850 | 3/1995 | (EP) | C09K/19/04 |
| 667384 | * 8/1995 | (EP) | |
| 0 708 165 A1 | 4/1996 | (EP) | |
| 2 162 515 | 2/1986 | (GB) | C07C/69/773 |
| 57-165334 | 10/1982 | (JP) | C07C/43/22 |
| 1-104031 | 4/1989 | (JP) | C07C/69/563 |
| 2-69443 | 3/1990 | (JP) | C07C/69/92 |
| WO 88/03530 | 5/1988 | (WO) | C07D/239/26 |
| WO 88/05803 | 8/1988 | (WO) | C09K/19/52 |
| WO 88/08441 | 11/1988 | (WO) | C09K/19/30 |
| WO 91/00897 | 1/1991 | (WO) | C09K/19/34 |
| WO 91/11418 | 8/1991 | (WO) | C09K/22/08 |
| WO 93/11280 | 6/1993 | (WO) | C23G/5/02 |
| WO 96/33251 | 10/1996 | (WO) | C09K/19/34 |

OTHER PUBLICATIONS

Jajer et al., Synthesis 1990,556.
Chaudhary et al., Tetrahedron Letters 1979, 95.
Middleton, J. Org. Chem. 40, 574 (1975).
Sakaguchi et al., Ferroelectrics 114, 265 (1991).
Byun et al., Tet, Lett. 30, 2751 (1989).
Gray et al., J. Chem. Soc., Perkin Trans. II 1989, 2041.
Iwakura et al., J. Org. Chem. 29, 379 (1964).
Miyasato et al., Jap. J. Appl. Phys. 22, L 661 (1983).
H. Nohira et al., Mol. Cryst. Liq. Cryst. 180B, 379–88 (1990).
Fukuda et al., "Antiferroelectric Chiral Smectic Liquid Crystals," J. Mater. Chem. 4 (7), 977 (1994).
Naciri et al., "Effect of Chiral End Group Variation on the Properties of Ferroelectric Copolymers," Ferroelectrics 148, 297 (1993).
Pelzl et al., Kristall Technik. 14, 817 (1979).
Pelzl et al., Liquid Crystals 2, 131 (1987).
Sierra et al., J. Am. Chem. Soc. 114, 7645 (1992).
Meyer, R.B. et al., J. Physique 36, L–69 (1975).
Zaschke, H. and Stolle, R., "Synthese niedrigschmelzender Kristallin–Flussiger Hetercyclen; 5–n–Alkyl–2–[4–n–alkanoyloxy–phenyl]pyrimidine," Z. Chem. 15, 441–43 (1975).

(List continued on next page.)

Primary Examiner—Shean C. Wu
(74) Attorney, Agent, or Firm—Kent S. Kokko

(57) ABSTRACT

Fluorine-containing, chiral liquid crystal compounds comprise (a) a chiral fluorochemical terminal portion comprising (i) at least one chiral center, which can optionally be heteroatom-substituted; (ii) a terminal fluoroalkyl, fluoroether, perfluoroalkyl, or perfluoroether group; and (iii) an alkylene or fluoroalkylene group optionally containing at least one catenary ether oxygen atom; (b) a chiral or achiral terminal portion consisting of a hydrocarbon or hydrocarbon ether group, and, when chiral, comprising at least one chiral center, which can optionally be heteroatom-substituted; and (c) a central core connecting the terminal portions; the alkylene or fluoroalkylene group of the chiral fluorochemical terminal portion having at least 3 in-chain atoms and being located between the chiral center of the chiral fluorochemical terminal portion and the central core. The compounds have smectic mesophases or latent smectic mesophases and are useful, for example, in liquid crystal display devices.

29 Claims, 1 Drawing Sheet

U.S. PATENT DOCUMENTS

| | | | |
|---|---|---|---|
| 4,011,173 | 3/1977 | Steinstrasser | 252/299 |
| 4,113,647 | 9/1978 | Coates et al. | 252/299 |
| 4,202,791 | 5/1980 | Sato et al. | 252/299 |
| 4,256,656 | 3/1981 | Beguim et al. | 260/465 D |
| 4,330,426 | 5/1982 | Eidenschink et al. | 252/299.63 |
| 4,367,924 | 1/1983 | Clark et al. | 350/334 |
| 4,393,231 | 7/1983 | Misaki et al. | 560/73 |
| 4,400,293 | 8/1983 | Romer et al. | 252/299.63 |
| 4,411,494 | 10/1983 | Crossland et al. | 350/339 R |
| 4,419,664 | 12/1983 | Crossland et al. | 340/784 |
| 4,439,015 | 3/1984 | Rich et al. | 350/350 R |
| 4,481,149 | 11/1984 | Misaki et al. | 260/465 D |
| 4,528,562 | 7/1985 | Crossland et al. | 340/805 |
| 4,564,694 | 1/1986 | Hirai et al. | 560/1 |
| 4,572,794 | 2/1986 | Eidenschink et al. | 252/299.2 |
| 4,576,732 | 3/1986 | Isogai et al. | 252/299.65 |
| 4,592,858 | 6/1986 | Higuchi et al. | 252/299.66 |
| 4,613,209 | 9/1986 | Goodby et al. | 350/350 S |
| 4,614,608 | 9/1986 | Le Barny et al. | 252/299.64 |
| 4,617,140 | 10/1986 | Eidenschink et al. | 252/299.61 |
| 4,668,427 | 5/1987 | Saito et al. | 252/299.66 |
| 4,780,242 | 10/1988 | Miyazawa et al. | 252/299.65 |
| 4,816,178 | 3/1989 | Katagiri et al. | 252/299.6 |
| 4,816,596 | 3/1989 | Langlois | 358/423 |
| 4,837,364 | 6/1989 | Desbois et al. | 568/43 |
| 4,876,027 | 10/1989 | Yoshinaga et al. | 252/299.65 |
| 4,879,060 | 11/1989 | Shionozaki et al. | 252/299.61 |
| 4,886,619 | 12/1989 | Janulis | 252/299.1 |
| 4,914,224 | 4/1990 | Shoji et al. | 560/65 |
| 5,051,527 | 9/1991 | Suzuki et al. | 560/51 |
| 5,062,691 | 11/1991 | Tristani-Kendra et al. | 359/56 |
| 5,082,587 | 1/1992 | Janulis | 252/299.01 |
| 5,141,669 | 8/1992 | Bloom et al. | 252/299.65 |
| 5,167,859 | 12/1992 | Wachtler et al. | 252/299.61 |
| 5,194,179 | 3/1993 | Suzuki et al. | 252/299.66 |
| 5,252,695 | 10/1993 | Niciri et al. | 528/30 |
| 5,262,082 | 11/1993 | Janulis et al. | 252/299.01 |
| 5,362,919 | 11/1994 | Costello et al. | 568/601 |
| 5,377,033 | 12/1994 | Radcliffe | 359/75 |
| 5,399,291 * | 3/1995 | Janulis et al. | 252/299.01 |
| 5,417,883 | 5/1995 | Epstein et al. | 252/299.01 |
| 5,474,705 * | 12/1995 | Janulis et al. | 252/299.01 |
| 5,482,650 * | 1/1996 | Janulis et al. | 252/299.01 |
| 5,545,345 | 8/1996 | Sekine et al. | 252/299.61 |
| 5,547,605 | 8/1996 | Fuss et al. | 252/299.6 |
| 5,550,273 * | 8/1996 | Savu | 252/299.61 |
| 5,554,317 | 9/1996 | Tsubata et al. | 252/299.01 |
| 5,641,427 * | 6/1997 | Shinjo et al. | 252/299.01 |
| 5,702,637 * | 12/1997 | Johnson et al. | 252/299.61 |
| 5,779,934 | 7/1998 | Higashii et al. | 252/299.61 |

OTHER PUBLICATIONS

Mochizuki, A. et al., SPIE 1665 108–09 (1992).

Pelzl, G. et al., Mol. Cryst. Liq. Cryst. 53, 167 (1979).

Clark, N.A. et al., Appl. Phys. Lett. 36, 899 (1980).

Holy, A. and Z. Arnold, Collection Chzechoslov. Chem. Commun. 38, 1371 (1973).

Sirutkaitis, R. et al., Advances in Liquid Crystal Research and Applications, Pergamon Press, Oxford, pp. 1023–1028 (1980).

Kahn, F.J., Appl. Phys. Lett. 22, 111 (1973).

Lagerwall et al., $1^{st}$ International Symposium On Ferroelectric Liquid Crystals, Bordeaux–Arcachon, France, 1987.

Partridge, M.W., and W.F. Short, J. Chem. Soc., 390 (1947).

P.M. Savu, Kirk–Othmer Encyclopedia of Chemical Technology, Fourth Edition, vol. 11, pp. 558–564, John Wiley & Sons, New York (1994).

Knunyants, I.L., L. Chih–yuan and V.V. Shokina, Advances in Chem. (Uspekhi Khimi) 42, original 1502, Eng. Trans, 461–76 (1963) Translation RSIC–165 (Redstone Information Center).

Arnold, Z. and F. Sorm, Coll. Czech. Chem. Commun. 23, 452 (1958).

Abe, T., and S. Nagase, "Electrochemical Fluorination (Simons Process) as a Route to Perfluorinated Organic Compounds of Industrial Interest," Preparation, Properties and Industrial Applications of Organofluorine Compounds, 37–38 (1982).

Patent Abstracts of Japan, vol. 15, No. 271 (C–0848), Jul. 10, 1991.

Zverkova, T.I. et al., Advances in Liquid Crystal Research & Applications, Pergamon Press, Oxford, pp. 991–995 (1980).

Schiller et al., Liquid Crystals 2, 21 (1987).

Molecular Crystals Liquid Crystals 47, 1 (1978).

Molecular Crystals Liquid Crystals 67, 235 (1981).

"The Silicon Liquid–Crystal Light Value," J. Appl. Phys. 57(4), 1356 (1985).

"Smectic Liquid Crystal from (Perfluorodecyl)decane," Molecular Crystals Liquid Crystals 2 (3–4), 111 (1985).

Molecular Crystals Liquid Crystals 114, 237 (1984).

J. Am. Chem. Soc. 86, 964 (1964).

Jap. Journal of Applied Physics 24(11), 1389 (1985).

J.W. Goodby and T.M. Leslie, "Some Novel Ferroelectric Smectic Liquid Crystals," Liquid Crystals & Ordered Fluids, vol. 4, pp. 1–32, Plenum Press, New York, 1984.

Gray, G.W., Liquid Crystals & Plastic Crystals, vol. 1, pp. 142–143, Ellis Horwood Limited (1974).

Le Barny, P. et al., Molecular Crystals and Liquid Crystals 127, 413 (1985).

Streitweiser, A. et al., Introduction to Organic Chemistry, pp. 378–380, 480, 837, Macmillan Publishing Co., New York (1976).

Nagashima et al., "The Synthesis and Mesomorphic Properties of Ferroelectric Liquid Crystals with a Fluorinated Asymmetric Frame," Liquid Crystals, vol. 23, No. 4, pp. 537–546 (1997).

* cited by examiner

LIQUID CRYSTAL COMPOUNDS HAVING A CHIRAL FLUORINATED TERMINAL PORTION

FIELD OF THE INVENTION

This invention relates to fluorinated chiral smectic liquid crystal compounds, to a process for the preparation of such compounds (and to intermediates for use therein), and to liquid crystal compound mixtures and electrooptical display devices containing such compounds.

BACKGROUND OF THE INVENTION

Devices employing liquid crystals have found use in a variety of electrooptical applications, in particular those which require compact, energy-efficient, voltage-controlled light valves, e.g., watch and calculator displays, as well as the flat-panel displays found in portable computers and compact televisions. Liquid crystal displays have a number of unique characteristics, including low voltage and low power of operation, which make them the most promising of the non-emissive electrooptical display candidates currently available.

One of the most important characteristics of a liquid crystal display device is its response time, i.e., the time required for the device to switch from the on (light) state to the off (dark) state. In a ferroelectric or anti-ferroelectric device, response time ($\tau=\eta/P_sE$) is proportional to the rotational viscosity ($\eta$) of the liquid crystal compound(s) contained within the device and is inversely proportional to their polarization ($P_s$) and to the applied electric field (E). Thus, response time can be reduced by using compound(s) having high polarizations or low viscosities, and such compounds are greatly desired in the art.

In the passive addressing of liquid crystal compounds exhibiting a spontaneous polarization, however, low polarization mixtures can be important for the practical operation of a liquid crystal device. Polarization reversal fields are larger for higher polarization mixtures, and polarization reversal fields cause switching or partial switching back to a material's original director alignment. This results in loss of the bistability that is crucial to the passive-matrix driving of ferroelectric liquid crystal devices.

Another potential disadvantage of using high polarization mixtures is the partial switching of their director alignment in response to non-switching (secondary) signals in a driving waveform. This continued response or fluctuation of the director causes a large decrease in the contrast ratio of a ferroelectric liquid crystal device.

In addition to fast response times, compounds should ideally possess broad smectic temperature ranges to enable operation of the device over a broad range of temperatures (or should be capable of combination with other liquid crystal compounds having different smectic temperature ranges without adversely affecting the smectic phase behavior of the base mixture).

SUMMARY OF THE INVENTION

Briefly, in one aspect, this invention provides fluorine-containing, chiral liquid crystal compounds having smectic mesophases or latent smectic mesophases. (Compounds having latent smectic mesophases are those which by themselves do not exhibit a smectic mesophase, but which, when in admixture with compounds having smectic mesophases or with other compounds having latent smectic mesophases, develop smectic mesophases under appropriate conditions.) The chiral liquid crystal compounds of the invention comprise (a) a chiral fluorochemical terminal portion that comprises (i) at least one chiral center (or chiral moiety), which can optionally be heteroatom-substituted; (ii) a terminal fluoroalkyl, fluoroether, perfluoroalkyl, or perfluoroether group (preferably, perfluoroalkyl or perfluoroether) wherein the fluoroalkyl and perfluoroalkyl groups are represented by the formula —$C_qF_{2q}X'$, wherein q is at least about 5 and X' is hydrogen or fluorine; and (iii) an alkylene or fluoroalkylene group optionally containing at least one catenary, i.e., in-chain, ether oxygen atom; (b) a chiral or achiral terminal portion consisting of a hydrocarbon or hydrocarbon ether group and, when chiral, comprising at least one chiral center, which can optionally be heteroatom-substituted; and (c) a central core connecting the terminal portions; the alkylene or fluoroalkylene group of the chiral fluorochemical terminal portion having at least 3 in-chain atoms and being located between the chiral center of the chiral fluorochemical terminal portion and the central core (an "extended group").

The chiral fluorochemical terminal portion of the compounds of the invention can be represented by the formula —D—R*—D—$R_f$, where R* is a cyclic or acyclic chiral moiety containing at least one chiral center (asymmetric carbon atom); $R_f$ is fluoroalkyl, perfluoroalkyl, fluoroether, or perfluoroether; and each D is independently and non-directionally selected from the group consisting of a covalent bond,

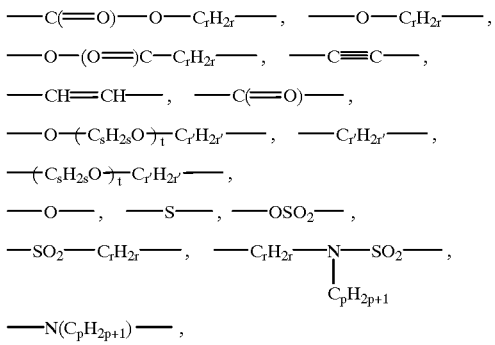

and combinations thereof, where one or more hydrogen atoms can optionally be replaced with fluorine, and where r and r' are independently integers of 0 to about 20, s is independently an integer of 1 to about 10 for each ($C_sH_{2s}O$), t is an integer of 1 to about 6, and p is an integer of 0 to about 4; with the proviso that at least one chiral center of R* is spaced from the central core by at least 3 in-chain atoms. Preferably, $R_f$ is perfluoroalkyl or perfluoroether; more preferably, $R_f$ is perfluoroether, as the perfluoroether-containing compounds of the invention exhibit, e.g., a broad smectic C mesophase, good compatibility with other smectic C compounds, and advantageous layer spacing behavior. When the $R_f$ group of the fluorochemical terminal portion is perfluoroalkyl or perfluoroether, it can contain small amounts of residual carbon-bonded hydrogen atoms but is preferably completely fluorinated.

In general, the compounds of this invention have a central core comprised of at least one or two rings independently selected from the group consisting of aromatic, heteroaromatic, alicyclic, substituted aromatic, substituted heteroaromatic, and substituted alicyclic rings, the rings being connected one with another by a covalent bond or by chemical groups selected from the group consisting of —COO—, —COS—, —HC=N—, —CH=CH—, —C≡C—, and —COSe—. The rings can be fused or non-fused. The heteroatoms within the heteroaromatic rings comprise at least one atom selected from the group consisting of nitrogen, oxygen, and sulfur. Non-adjacent ring carbon atoms in the alicyclic rings can be substituted by nitrogen, oxygen, or sulfur atoms. When the ring(s) are aromatic, heteroaromatic, substituted aromatic, or substituted heteroaromatic, the non-fused rings of the core are preferably no more than about two in number.

The chiral liquid crystal compounds of the invention exhibit exceptionally wide mesomorphic temperature ranges. When used in electrooptical devices, the compounds provide fast response times upon application of an electric field over broad temperature ranges. This makes them extremely useful in the preparation of mixtures that operate in their active mesomorphic phase in the range of from about −30° C. to about 70° C.

Surprisingly, in comparison with similar compounds having fewer than 3 in-chain atoms between at least one chiral center of the fluorochemical terminal portion and the central core, the compounds of the invention provide comparable electrooptic response speeds in spite of their lower measured polarization values. These lower polarization values in combination with broad mesogenic temperature ranges enable the utilization of liquid crystal mixtures that contain up to 100% of the chiral (optically active) compounds of the invention. In general, mixtures containing a high concentration of the compounds of this invention exhibit more temperature independent switching properties, which is important for the reliable and consistent operation of liquid crystal devices.

Furthermore, the use of high concentrations of liquid crystal compounds having low polarizations also provides a decrease (relative to the use of low concentrations of compounds having high polarizations) in the partial switching response of the resulting compositions to non-switching (secondary) signals in the driving waveform that is commonly used in the passive addressing of liquid crystal devices. Such a decrease in this response is critical for improving the contrast of a device.

The compounds of the invention are useful in admixture with themselves or with other chiral or achiral liquid crystal compounds (as dopants or as the major components), for electrooptical display applications. The compounds have a number of desirable properties when used in admixture with themselves or with other liquid crystal compounds, preferably compounds having fluorinated terminal portions such as those compounds disclosed, for example, in U.S. Pat. No. 4,886,619 (Janulis), U.S. Pat. No. 5,082,587 (Janulis), U.S. Pat. No. 5,262,082 (Janulis et al.), and U.S. Pat. No. 5,658,491 (Kistner et al.).

For example, the compounds of the invention when admixed with such preferred liquid crystal compounds show excellent compatibility, show a beneficial effect or only a minimal negative effect on the smectic C temperature range of the resulting mixtures (even when present at high concentrations), and provide ferroelectric mixtures having fast electrical response times. Mixtures containing the compounds exhibit favorable alignment, switching, response to an electric field, temperature dependence of response speed, temperature dependence of polarization, contrast, layer structure, and mesomorphic temperature ranges. Compounds of the invention can also be used to optimize mixture properties such as tilt angle, memory angle, spontaneous polarization and its temperature dependence, mesomorphic transition temperatures, switching behavior, birefringence, and the temperature dependence of layer spacing.

In other aspects, this invention also provides liquid crystal compounds (described below) having two fluorochemical terminal portions, a mixture of liquid crystal compounds comprising at least one liquid crystal compound of the invention, a liquid crystal display device containing at least one liquid crystal compound of the invention, and liquid crystal intermediate compounds.

BRIEF DESCRIPTION OF THE DRAWING

These and other features, aspects, and advantages of the present invention will become better understood with regard to the following description, appended claims, and accompanying drawing, wherein:

DETAILED DESCRIPTION OF THE INVENTION

Figure 1:
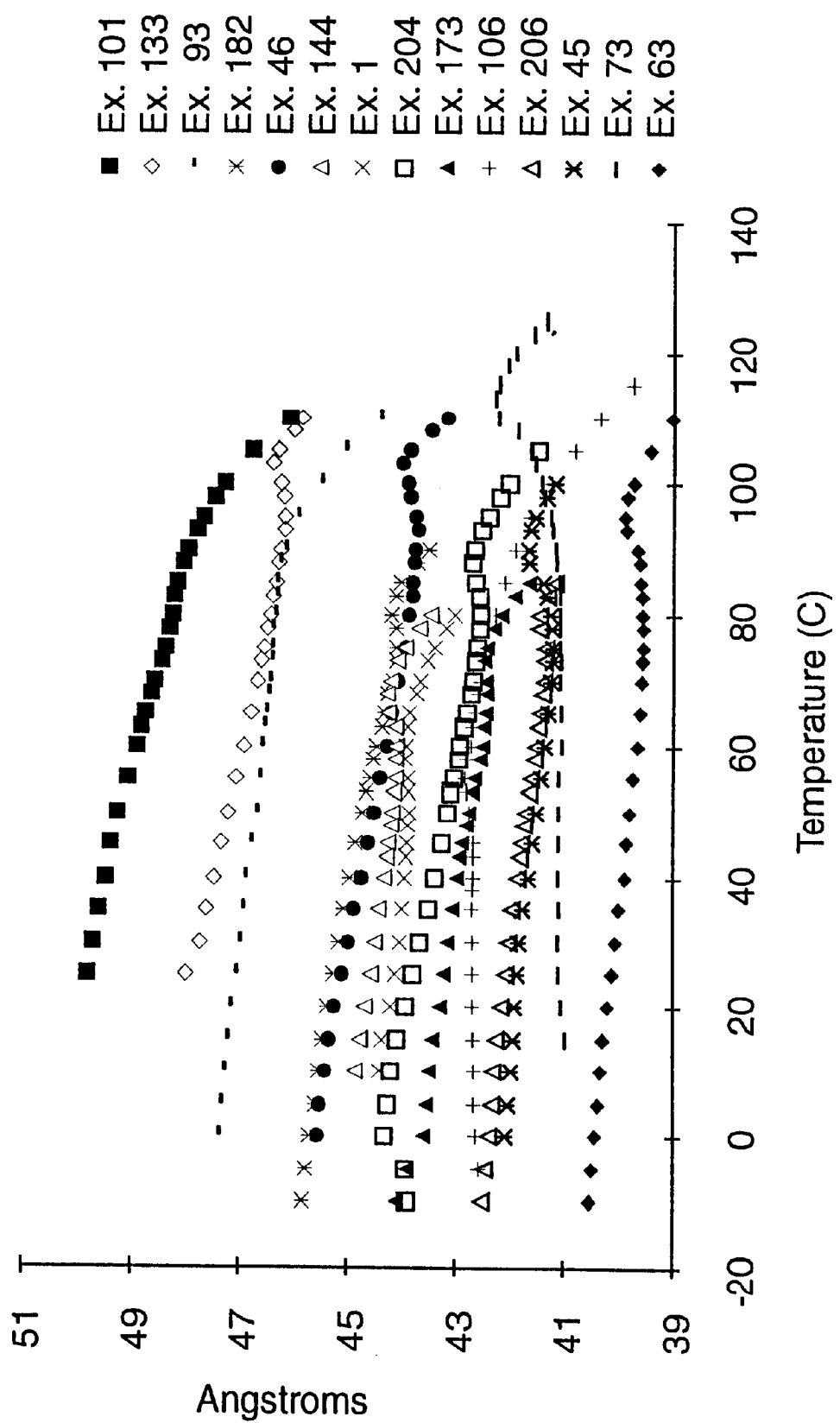
FIG. 1 shows a plot of smectic C layer spacing (in Angstroms) versus temperature (in degrees Centigrade) for selected compounds of the invention that were prepared by the procedures given in the designated Examples.

A class of the above-described liquid crystal compounds of the present invention can be represented by the general formula I:

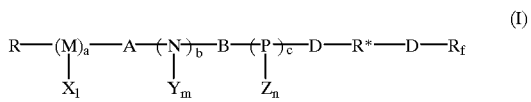

where M, N, and P are each independently selected from the group consisting of

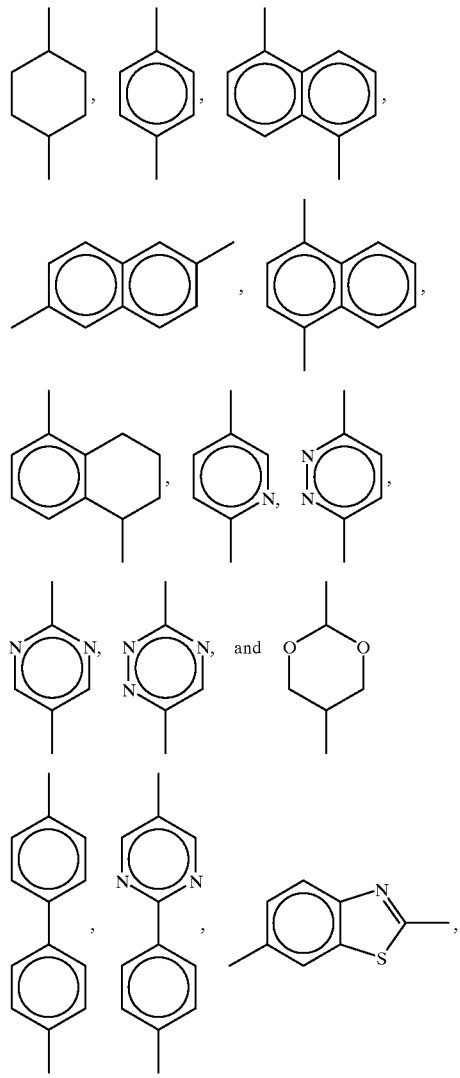

-continued

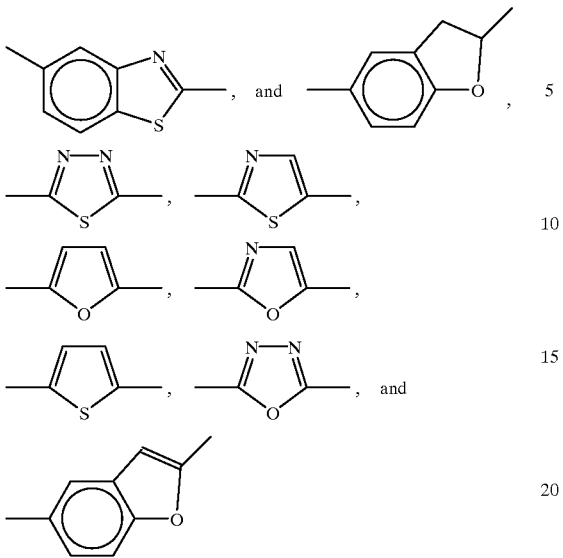

a, b, and c are each independently zero or an integer of from 1 to 3, with the proviso that the sum of a+b+c be at least 1 (and preferably no greater than 2);

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O— each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

each D is non-directionally and independently selected from the group consisting of a covalent bond,

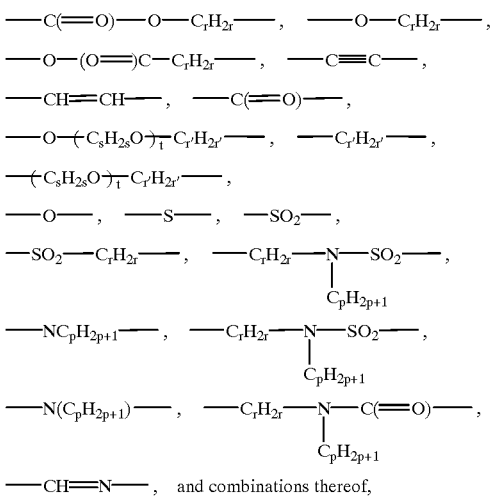

where one or more hydrogen atoms can optionally be replaced with fluorine, and where r and r' are independently integers of 0 to about 20, s is independently an integer of 1 to about 10 for each (C$_s$H$_{2s}$O), t is an integer of 1 to about 6, and p is an integer of 0 to about 4;

R is selected from the group consisting of

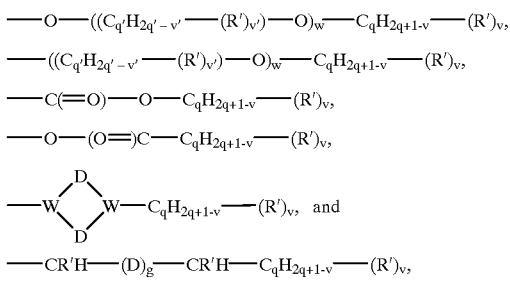

—CR'H—(D)$_g$—CR'H—C$_q$H$_{2q+1-v}$—(R')$_v$, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$ (preferably, —H or —F); q' is independently an integer of 1 to about 20 for each (C$_{q'}$H$_{2q'}$—O); q is an integer of 1 to about 20; w is an integer of 0 to about 10; v is an integer of 0 to about 2; each v' is independently an integer of 0 to about 2; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and R can be chiral or achiral; and R* is a cyclic or acyclic chiral moiety containing at least one chiral center; and R$_f$ is fluoroalkyl, perfluoroalkyl, fluoroether, or perfluoroether;

with the proviso that there are at least 3 in-chain atoms between the central core structure —(M)$_a$—A—(N)$_b$B—(P)$_c$— and at least one chiral center of R*.

Preferably, R$_f$ is a perfluoroalkyl or perfluoroether group and R* is selected from the group consisting of —O—((C$_{q'}$H$_{2q'-v'}$—(R')$_{v'}$)—O)$_w$—C$_q$H$_{2q-v}$—(R')$_v$—, —((C$_{q'}$H$_{2q'-v'}$—(R')$_{v'}$)—O)$_w$—C$_q$H$_{2q-v}$—(R')$_v$—, —C(=O)—O—C$_q$H$_{2q-v}$—(R')$_v$—, —O—(O=)C—C$_q$H$_{2q-v}$—(R')$_v$—,

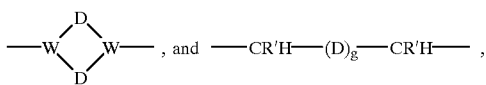

where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$ (preferably, —H, —F, —CF$_3$, —Br, —OH, or —OCH$_3$; more preferably, —H, —F, or —CF$_3$); q' is independently an integer of 1 to about 20 for each ((C$_q$H$_{2q'-v'}$—(R')$_{v'}$)—O); q is an integer of 1 to about 20; w is an integer of 0 to about 10; v is an integer of 0 to about 3; each v' is independently an integer of 0 to about 3; g is an integer of 1 to about 3; each D is independently and non-directionally selected from the group set forth for D above, with the proviso that the ring containing D has from about 3 to about 10 ring atoms; and each W is independently selected from the group consisting of N, CR', and SiR'. More preferably, R$_f$ is perfluoroether.

In defining R$_f$, particularly preferred perfluoroalkyl and fluoroalkyl groups are those which can be represented by the formula —C$_q$F$_{2q}$X', where q is as defined above (and, preferably, is at least about 5) and X' is hydrogen or fluorine. Particularly preferred perfluoroether groups are those which can be represented by the formula —(C$_x$F$_{2x}$O)$_z$C$_y$F$_{2y+1}$, where x is independently an integer of 1 to about 10 for each $(C_xF_{2x}O)$, y is an integer of 1 to about 10, and z is an integer of 1 to about 10. Preferably, the perfluoroether group is linear, x is independently an integer of 1 to about 6 for each $(C_xF_{2x}O)$, y is an integer of 1 to about 6, and z is an integer of 1 to about 6.

Preferred subclasses of the above-described chiral compounds of the invention can be represented by the following formula:

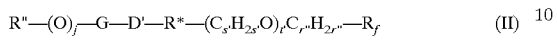  (II)

where R" is $(R')_v—C_qH_{2q+1-v}$, where q is an integer of 2 to about 10, each R' is independently selected from the group consisting of hydrogen, fluorine, chlorine, methyl, and perfluoromethyl, and v is an integer of 1 to about 2;

j is an integer of 0 or 1;

G is selected from the group consisting of

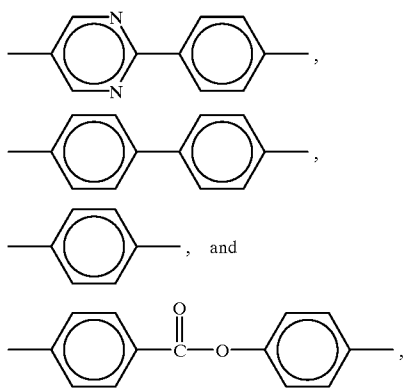

where one or more of the aromatic hydrogen atoms can be replaced with fluorine;

D' is selected from the group consisting of —O—$(C_sH_{2s}O)_t$—$C_{r'}H_{2r'}$—, —$C_rH_{2r}$—, —$(C_sH_{2s}O)_t$—$C_{r'}H_{2r'}$—, and —O—$C_rH_{2r}$—, where r and r' are independently integers of 0 to about 12, s is independently an integer of 1 to about 10 for each $(C_sH_{2s}O)$, and t is an integer of 1 to about 3;

R* is selected from the group consisting of —$C_qH_{2q-v}$—$(R')_v$— and

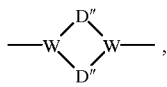

where R' is —F, q is an integer of 1 to about 4, v is an integer of 1 to about 3, W is N or CH, and D" is —C(=O)—O— or —$CH_2$—;

s' in Formula II is an integer of 1 to about 6;

t' in Formula II is an integer of 0 or 1;

r" in Formula II is an integer of 1 to about 3; and $R_f$ is selected from the group consisting of —$C_qF_{2q+1}$ and —$(C_xF_{2x}O)_zC_yF_{2y+1}$, where q is an integer of 1 (preferably 5) to about 6, x is independently an integer of 1 to about 10 for each $(C_xF_{2x}O)$, y is an integer of 1 to about 8, and z is an integer of 1 to about 5;

with the proviso that there are at least 3 in-chain atoms between the central core structure G and at least one chiral center of R*.

More preferably, s', t', and r" in Formula II are each an integer of 1.

The fluorine-containing liquid crystal compounds of the invention can be prepared by a process comprising the steps of (a) mixing at least one compound represented by the formula

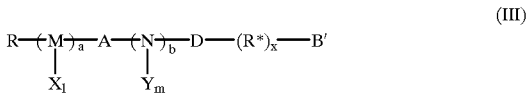  (III)

with at least one compound represented by the formula

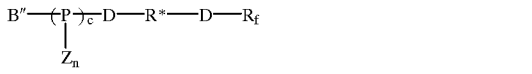  (IV)

or mixing at least one compound represented by the formula

  (V)

with at least one compound represented by the formula

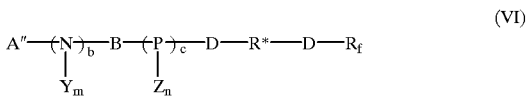  (VI)

or mixing at least one compound represented by the formula

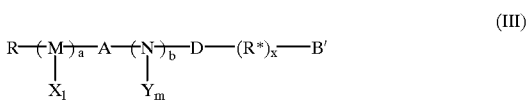  (III)

with at least one compound represented by the formula $B''—D—R_f$   (VII), where M, N, P, a, b, c, A, B, X, Y, Z, l, m, n, D, R, R*, and $R_f$ are as defined above for formula I; x is an integer of 0 or 1; and each A', A", B', and B" are independently selected from the group consisting of —H, —Cl, —Br, —I, —OH, —COOH, —$CH(CH_2OH)_2$, —SH, —SeH, —TeH, —$NH_2$, —COCl, —CHO, —$OSO_2R_f'''$, —$OSO_2CH_3$, —C≡CH, dialkyl borane, —CH=$CH_2$, —NH(C=O)O$C_qH_{2q+1}$, —NCO, —$OSO_2$-cyclo($C_6H_4$)—$CH_3$, —$CH_2COOH$, and —CH(C(O)O—$C_qH_{2q+1})_2$, where $R_f'''$ is a perfluoroalkyl group having from 1 to about 10 carbon atoms and q is an integer of 0 to about 20, and with the proviso that $(R*)_x$—A' can enter into an addition or condensation reaction with A" and that $(R*)_x$—B' can enter into an addition or condensation reaction with B";

and (b) allowing compounds III and IV, compounds V and VI, or compounds III and VII to react, optionally in the presence of suitable coupling agent(s), i.e., reagent(s) which effect coupling. For Formula IV, B" is preferably selected from the group consisting of —C≡CH, dialkyl borane, and —CH=$CH_2$ (more preferably —CH=$CH_2$), and —D—R*—D—$R_f$ is preferably —D'—R*—$(C_sH_{2s'}O)_{t'}C_{r''}H_{2r''}$—$R_f$ as defined above for Formula II.

In another aspect, liquid crystal compounds of the present invention also include compounds that have two fluorochemical terminal portions and can be represented by the general formula VIII:

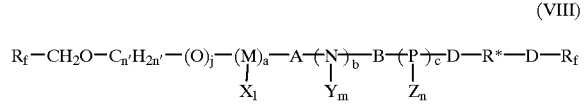  (VIII)

where n' is an integer of 0 to about 10 (preferably from about 2 to about 6); j is an integer of 0 or 1; each $R_f$ moiety is independently selected from the group consisting of fluoroalkyl, fluoroether, perfluoroalkyl, and perfluoroether (preferably, perfluoroalkyl or perfluoroether; more preferably, perfluoroether); and definitions (and preferred definitions) for the other moieties are as stated above for Formula I. Such compounds can be prepared by the above-described methods involving Formulas III, IV, V, VI, and VII, wherein the R moiety is replaced with $R_f$—$CH_2O$—$C_{n'}H_{2n'}O$— (wherein $R_f$ and n' are as defined for Formula VIII).

Preferred subclasses of the above-described chiral compounds of the invention having two fluorochemical terminal portions can be represented by the following formula:

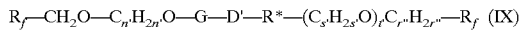

$$R_f\text{—}CH_2O\text{—}C_{n'}H_{2n'}O\text{—}G\text{—}D'\text{—}R^*\text{—}(C_sH_{2s}O)_t C_{r'}H_{2r'}\text{—}R_f \quad (IX)$$

where n' is an integer of about 2 to about 6 (preferably, 3 or 4); each $R_f$ is independently selected from the group defined above for $R_f$ in regard to Formula II; and all other moieties (and preferred moieties) are as defined above for Formula II.

Most of the compounds of the present invention have enhanced smectic mesophases. Mixtures of the compounds of the invention with other liquid crystal materials can be formulated to provide desired transition temperatures and broad mesophase temperature ranges. Such mixtures preferably contain compounds having fluorinated terminal portions, such as those compounds described, for example, in U.S. Pat. No. 4,886,619 (Janulis) and U.S. Pat. No. 5,082,587 (Janulis) and, most preferably, U.S. Pat. No. 5,262,082 (Janulis et al.) and U.S. Pat. No. 5,658,491 (Kistner et al.), the descriptions of which are incorporated herein by reference. The liquid crystal compounds of the invention can also be used to prepare ferroelectric liquid crystal devices such as, e.g., those described in U.S. Pat. No. 5,417,883 (Radcliffe) and U.S. Pat. No. 5,641,427 (Shinjo) and in EP 769582 and EP 769543.

The compounds of this invention in admixture with other chiral or achiral liquid crystal compounds may exhibit chiral smectic liquid crystal behavior. Furthermore, many of the perfluoroether group-containing liquid crystal compounds of the invention when used alone or when mixed with other liquid crystal compounds of the invention or with achiral, fluorine-containing liquid crystal compounds (preferably, the perfluoroether group-containing liquid crystal compounds described in U.S. Pat. No. 5,262,082 (Janulis et al.)) exhibit a reduced temperature dependence of the smectic interlayer spacing. This property provides for the spontaneous generation of an essentially bookshelf type layer structure, which is ideal for a ferroelectric liquid crystal device. In general, the compounds of the invention exhibit maintenance or expansion of the smectic C layer spacing with decreasing temperature.

Another advantage of using the materials of this invention in the formulation of liquid crystal mixtures is the low birefringence which can be obtained. The low birefringence of the liquid crystal compounds of the invention (relative to their non-fluorine-containing analoques) allows the fabrication of devices with larger device spacings. Light transmission through, e.g., a surface-stabilized ferroelectric device (as described in U.S. Pat. No. 4,367,924, the description of which is incorporated by reference herein) with two polarizers is represented by the following equation:

$$I=I_o\ (\sin^2(4\Theta))\ (\sin^2(\pi\Delta nd/\lambda))$$

where $I_o$=transmission through parallel polarizers

Θ=material tilt angle

Δn=liquid crystal birefringence d=device spacing

λ=wavelength of light used

To maximize the transmission, both $\sin^2\ (4\Theta))$ and $\sin^2 (\pi\Delta nd/\lambda)$ must be at maximum. This occurs when each term equals one. The first term is a maximum when the tilt angle equals 22.5°. This is a function of the liquid crystal and is constant for a given material at a given temperature. The second term is maximum when $\Delta nd=\lambda/2$. This demonstrates the criticality of the low birefringence of the materials of this invention. Low birefringence allows a larger device thickness, d, for a given wavelength of light. Thus, a larger device spacing is possible while still maximizing transmission, allowing easier device construction.

Objects and advantages of this invention are further illustrated by the following examples, but the particular materials and amounts thereof recited in these examples, as well as other conditions and details, should not be construed to unduly limit this invention.

In the following examples, all temperatures are in degrees Celsius and all parts and percentages are by weight unless indicated otherwise. Commercially available materials were chemically transformed by reaction pathways well-known to those skilled in the art and detailed in the examples. Chemical transformations were comprised of acylation, esterification, etherification, alkylation, and combinations thereof using fluorine-containing and non-fluorine-containing reactants to provide the precursor compounds, which, in turn, were caused to react together to yield the chiral, fluorine-containing liquid crystal compounds of this invention.

Compounds prepared in the various examples of this invention were characterized by their melting or boiling point, and structures were confirmed by using at least one of the following methods of analysis: chromatography; $^{13}C$—, $^{1}H$—, and $^{19}F$—NMR; and infrared and mass spectroscopies.

EXAMPLES

The 5-alkyl-2-(4-hydroxyphenyl) pyrimidines used in the examples were prepared essentially as described by Zaschke and Stolle in "Synthese niedrigschmelzender Kristallin-Flussiger Heterocyclen; 5-n-Alkyl-2-[4-n-alkanoyloxyphenyl]pyrimidine," Z.Chem. 15, 441–3 (1975). (S)- and (R)-2-fluoro-decyl-p-toluenesulfonate were prepared essentially as described by Nohira et al. in Mol. Cryst. Liq. Cryst. 180B, 379 (1990). Fluorinated alcohols were prepared essentially as described in U.S. Pat. No. 5,262,082 (Janulis et al.; the description of which is incorporated herein by reference) by sodium borohydride reduction of the corresponding perfluorinated acids (or derivatives), which had been prepared by electrochemical fluorination (ECF) or by direct fluorination (using elemental fluorine) of the corresponding hydrocarbon acids (or derivatives). See, e.g., the description of ECF given in U.S. Pat. No. 2,519,983 (Simons), the description of which is incorporated herein by reference. Direct fluorination is described, e.g., in U.S. Pat. No. 5,362,919 (Costello et al.), the description of which is also incorporated herein by reference.

Example 1

Preparation of (S)-5-Octyl-2-[4-(8-(2-(2-(2-(trifluoromethoxy(tetrafluoroethoxy)tetrafluoroethoxy)-2,2-difluoroethoxy)-7-fluorooctyl)phenyl]pyrimidine Preparation of Starting Material:

(S)-8-(2-(2-(2-(Trifluoromethoxy(tetrafluoroethoxy)(tetrafluoroethoxy)-2,2-difluoroethoxy)-7-fluorooct-1-ene Into a dry 3 liter flask fitted with a reflux condenser, a nitrogen inlet, a thermocouple, and an addition funnel, were placed magnesium turnings (37.8 g, 1.55 mol) and dry t-butylmethylether (100 mL). 5-bromo-1-pentene (225 g, 1.51 mol) was added to the flask dropwise at a rate which maintained the reflux temperature of the reaction mixture (55–6° C.). Additional t-butylmethylether (about 1.5 L) was added in 50 mL portions during the addition of the bromide. After the addition was complete, the resulting mixture was heated to reflux for an additional 30 minutes. The mixture was then cooled to −65° C. Dilithiotetrachlorocuprate (302 mL, 0.1 M in tetrahydrofuran (THF)) was added, and the resulting reaction mixture was stirred for 45 minutes at −65° C. followed by addition of R(−)-epichlorohydrin (125.7 g, 1.36 mol) at a rate not to exceed a reaction mixture temperature of −40° C. The reaction mixture was stirred for an additional 30 minutes, was warmed to −5° C., and was then quenched by the addition of 250 g of ammonium chloride in 2.5 liters of water. The resulting aqueous phase was extracted with t-butylmethylether (300 mL), and the combined ether layers were washed with ammonium chloride/ammonium hydroxide buffer (2×500 mL) and saturated sodium chloride (2×500 mL). The solvent was removed under reduced pressure, and the resulting residue was distilled (b.p.=57–72° C. at 0.15 torr) to give 183 g of (R)-8-chloro-7-hydroxy-oct-1-ene.

This chlorohydrin was converted in situ to (R)-1,2-epoxy-7-octene and reacted with 2-(2-(2-(trifluoromethoxy (tetrafluoroethoxy)tetrafluoroethoxy)-2,2-difluoroethanol using the following procedure: (R)-8-chloro-7-hydroxy-oct-1-ene (100 g, 0.61 mol), aqueous potassium hydroxide (45 mL of 45 wt. %), 2-(2-(2-(trifluoromethoxy (tetrafluoroethoxy)tetrafluoroethoxy)-2,2-difluoroethanol (291 g, 0.733 mol), Adogen™ 464 (60 g), and 1,2-dimethoxyethane (60 mL) were added to a one liter flask fitted with a mechanical stirrer, an addition funnel, a reflux condenser, and a thermometer. The resulting solution was stirred for one hour at 45° C. and then warmed to 60° C., at which time aqueous potassium hydroxide (70 mL of 45 wt %) was added dropwise. This solution was heated for 2 hours at 60° C. and then at 70° C. for 8 hours. Water (300 mL) was added, and the resulting organic phase was separated and washed with 7 weight % HCl (300 mL). The organic phase was again separated and was concentrated under reduced pressure (25 torr). The resulting crude product was then purified by silica gel chromatography using toluene as eluent to give 268 g of (R)-8-(2-(2-(2-(trifluoromethoxy(tetrafluoroethoxy)tetrafluoroethoxy)-2,2-difluoroethoxy)-7-hydroxyoct-1-ene.

Under a nitrogen atmosphere, (R)-8-(2-(2-(2-(trifluoromethoxy(tetrafluoroethoxy) tetrafluoroethoxy)-2,2-difluoroethoxy)-7-hydroxyoct-1-ene (60 g, 0.103 mol) and dry toluene (120 mL) were added to an oven-dried flask with stirring. The resulting solution was cooled to −15° C., perfluorobutanesulfonyl fluoride (58.9 g, 0.185 mol) was added, and the resulting reaction mixture was stirred for 5 minutes. 1,8-Diazabicyclo[5.4.0]undec-7-ene (28.7 g, 0.189 mol) was then added at a rate so as not to exceed a temperature of 5° C. for the reaction mixture. The reaction mixture was stirred for 1 hour at ambient temperature and was quenched by the addition of toluene (120 mL) and water (60 mL). The resulting organic phase was separated from the resulting aqueous phase, and the aqueous phase was washed with toluene. The combined organic extracts were washed with 120 mL of 7 volume % HCl. The combined extracts were concentrated under reduced pressure (25 torr), and the resulting crude product was distilled (b.p. 58–65° C. at 0.01 torr) to give 33.8 g of (S)-8-(2-(2-(2-(trifluoromethoxy (tetrafluoroethoxy)tetrafluoroethoxy)-2,2-difluoroethoxy)-7-fluorooct-1-ene.

Preparation of Starting Material:

4-(5-Octylpyrimidine-2-yl)phenyl Nonafluorobutane Sulfonate

A 12 liter flask fitted with a mechanical stirrer, a constant addition funnel, a thermometer, and a reflux condenser was charged with of 5-octyl-2-(4-hydroxyphenyl)pyrimidine (300 g, 1.05 mol), perfluorobutanesulfonyl fluoride (378 g, 1.25 mol), and tert-butylmethylether (3 L) under positive nitrogen pressure and was cooled with an ice bath to 16° C. 1,8-Diazabicyclo[5.4.0]undec-7-ene (180 g, 1.18 mol) was added to the resulting mixture over 25 minutes, while maintaining the temperature of the mixture below 20° C. After the addition was complete, the mixture was stirred at room temperature for 2 hours, and then 3 liters of water was added. The resulting aqueous phase was separated from the resulting organic phase, and the organic phase was washed with a mixture of 2.25 liters of water and 0.75 liters of concentrated HCl. The solvent was removed from the organic phase under reduced pressure to yield 697 g of crude product, which was recrystallized from ethanol to yield 4-(5-octyl pyrimidine-2-yl)phenyl nonafluorobutane sulfonate (499 g, 84% yield).

Preparation of Product:

A 1 liter flask fitted with a magnetic stirring bar, a thermocouple, and a nitrogen inlet was charged with anhydrous tetrahydrofuran (230 mL) and 9-borabicyclo[3.3.1] nonane (229 mL, 0.5 M in THF) under a nitrogen atmosphere. The resulting solution was cooled to 5° C. and then (S)-8-(2-(2-(2-(trifluoromethoxy(tetrafluoroethoxy) tetrafluoroethoxy)-2,2-difluoroethoxy)-7-fluorooct-1-ene (50 g, 95.4 mmol) was added via syringe at a rate such that the temperature of the resulting mixture was maintained below 7° C. The mixture was stirred for 14 hours, and then PdCl$_2$(Ph$_3$P)$_2$ (2.0 g, 2.86 mmol), NaOH (11.4 g, 286.1 mmol), and 4-(5-octyl pyrimidine-2-yl)phenyl nonafluorobutane sulfonate (54.0 g, 95.4 mmol) were added. The resulting mixture was heated to 50° C. for 1.5 hours and was then poured into 1 liter of water. The resulting product was extracted with toluene (3×100 mL), and the toluene extracts were washed with water (3×100 mL). The solvent was removed under reduced pressure, and the resulting crude brown product was chromatographed through 200 g of silica gel (10 volume % ethyl acetate in heptanes eluent) and was further purified by recrystallization from heptane at −20° C. followed by Kugelrohr distillation (b.p. 195–197° C. at 0.02 torr; yield 54.7 g).

Examples 2 Through 140

Example 2–140 were prepared essentially as described in Example 1 using homologous starting materials according to the following general Scheme (where n is an integer of 0 to 7 and R$_f$ and R are as defined above for Formula I.

Scheme 1

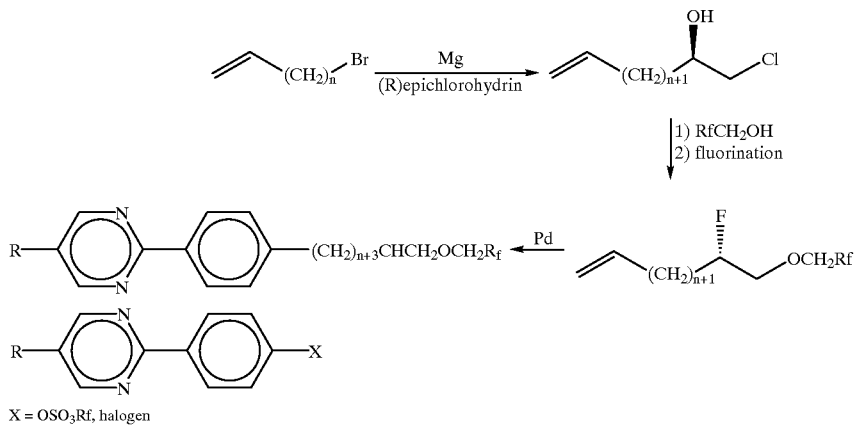

X = OSO₃Rf, halogen

Example 141

Preparation of 5-Hexyloxy-2-[4(-6-(2-pentafluoroethoxy)-2,2-difluoroethoxy)-(S)-7-fluorooctyl)phenyl]pyrimidine The starting material, 5-hexyloxy-2-[4(-6-(2-pentafluoroethoxy)-2,2-difluoroethoxy)-(R)-7-hydroxyoctyl)phenyl]pyrimidine, was prepared by combining 5-hexyloxy-2-[4-(1,2-epoxyhexyl)phenyl]pyrimidine (3.0 g, 7.85 mmol; which can be prepared from (R)-1,2-epoxy-7-octene and 4-(5-hexyloxypyrimidine-2-yl)phenyl trifluoromethanesulfonate by the method described in Oh-e, T. et. al., J. Org. Chem. 58, 2201 (1993).), 2-pentfluoroethoxy-2,2-difluoroethanol (2.04 g, 9.42 mmol), Adogen™ 464 (0.4 mL), potassium hydroxide (1.0 mL 50 weight % in H₂O), and THF (1 mL). The resulting mixture was heated at 75° C. for 12 hours. The resulting alcohol was purified by recrystallization from acetonitrile (yield 3.99 g).

The title compound was prepared by dropwise addition of 5-hexyloxy-2-[4(-6-(2-pentafluoroethoxy)-2,2-difluoroethoxy)-(R)-7-hydroxyoctyl)phenyl]pyrimidine (3.99 g, 6.68 mmol) in THF (13 mL) to a solution of diethylaminosulfur trifluoride (1.2 g, 7.35 mmol) in THF (22 mL) at −50° C. The resulting mixture was then warmed to 0° C. and subsequently cooled to −50° C. before addition of pyridine (1.1 mL). The mixture was stirred at room temperature for 12 hours and was then added to a slurry of silica gel (15 g in 100 mL diethyl ether). Solvent was removed under reduced pressure, and the resulting product was purified by column chromatography (silica gel), eluting with 10:1 hexane/ethyl acetate, followed by Kugelrohr distillation (b.p. 156–165° C. at 0.1 torr; yield 0.93 g).

Examples 142 Through 163

Examples 142–163 were prepared essentially as described in Example 141 using homologous materials as shown in the following general Scheme 2. In Scheme 2, n is an integer of 4 to 6, and R$_f$ and R are as defined above for Formula I.

Scheme 2

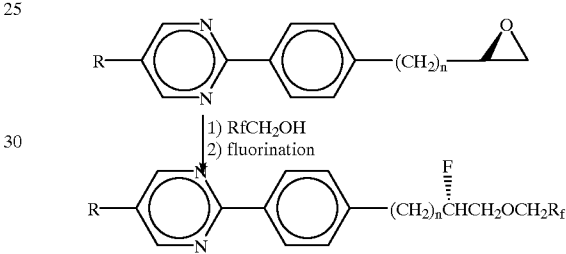

Examples 164 Through 175

Examples 164–175 were prepared essentially as described in Example 141 using (S) 3-(3-butenyloxy)-1,2-epoxy-propane (prepared from (R) epichlorohydrin and 3-buten-1-ol using BF₃·Et₂O and subsequent treatment with base) in place of (R)-1,2-epoxy-7-octene according to the following general Scheme 3. In Scheme 3, n is an integer of 4, and R$_f$ and R are as defined above for Formula I.

Scheme 3

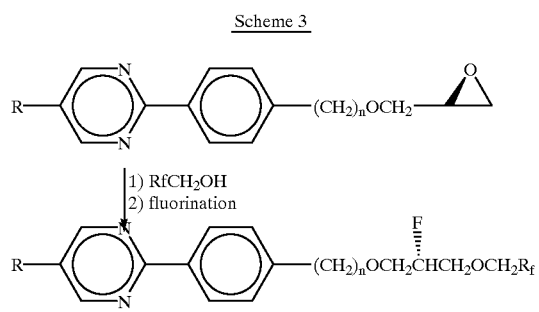

Examples 176 Through 186

Examples 176–186 were prepared essentially as described in Example 1 using (R) 1-chloro-3-(5-hexenyloxy)-2-propanol (prepared from (R) epichlorohydrin and 5-hexen-1-ol using BF₃·Et₂O) in place of (R)1-chloro-7-octen-2-ol according to the following general Scheme 4 (where n is an integer of 4 to 6, and R and R$_f$ are as defined above for Formula I);

Scheme 4

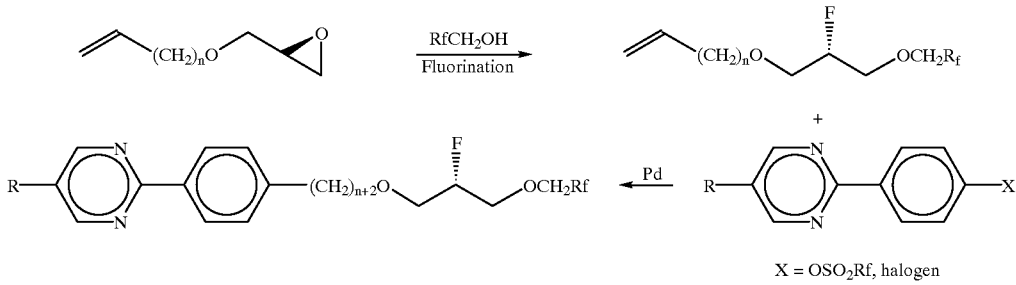

X = OSO$_2$Rf, halogen

Example 187

Example 187 was prepared essentially as described in Example 1 using (S) 1-chloro-3-(5-octenyloxy)-2-propanol (prepared from (R) epichlorohydrin and 7-octen-1-ol using BF$_3$·Et$_2$O) in place of (R) 1-chloro-7-octen-2-ol.

Examples 188 Through 201

Examples 188–201 were prepared essentially as described in Example 176 using 5-benzyloxy-2-(4-trifluoromethanesulfonyloxyphenyl) pyrimidine in place of 5-octyloxy-2-(4-nonafluorobutanesulfonyloxyphenyl) pyrimidine. The resulting compound was treated with 10 weight % palladium on carbon under hydrogen pressure (3100 torr) to obtain 5-hydroxy-2-[4-(6-(3-(2-(2-(2-(trifluoromethoxy (tetrafluoroethoxy)tetrafluoroethoxy)-2,2-difluoroethoxy)-(S)-2-fluoropropyloxy)hexyl)phenyl]pyrimidine. This material was then treated under basic conditions with the corresponding chloride or methane sulfonate to give the final products. The procedure is shown in the following general Scheme 5 (where Bn is a benzyl protecting group, n is an integer of 3 or 4, m is an integer of 0 or 1, and R$_f$ and R are as defined above for Formula I):

Example 202

Preparation of 5-Octyloxy-2-[4-(2-(3-(2-(2-(nonafluorobutoxy)tetrafluoroethoxy)-2,2-difluoroethoxy)-(R)-2-fluoropropoxy)ethoxy)phenyl] pyridine The title compound was prepared by combining 5-octyloxy-2-[4-hydroxyphenyl]pyrimidine (2.2 g, 7.4 mmol), 2-(3-(2-(2-(nonafluorobutoxy)tetrafluoroethoxy)-2,2-difluoroethoxy)-(R)-2-hydroxypropoxy)ethyl chloride (4.2 g, 7.4 mmol), and potassium carbonate (1.2 g, 8.9 mmol) in a 1:1 mixture of acetonitrile and dimethyl formamide. After heating overnight, the resulting mixture was poured into deionized water (40 mL), was filtered, and the resulting product purified by chromatography, eluting with 4:1 and then 2:1 hexane/ethyl acetate (yield 2.56 g). The resulting chiral (R)-hydroxy compound (2.5 g, 3.0 mmol) was treated with diethylaminosulfur trifluoride (0.58 g, 3.6 mmol) to produce the title compound, which was purified by recrystallization from ethanol, followed by Kugelrohr distillation (b.p. 210–20° C. at 0.4 torr; yield 1.42 g).

Example 203

Preparation of 5-heptyl-2-[4-(3-(3-(2-(2-(nonafluorobutoxy)tetrafluoroethoxy)-2,2-difluoroethoxy)-(S)-2-fluoropropoxy)propoxy) phenyl]pyrimidine The starting material, 3-(3-(2-(2-(nonafluorobutoxy) tetrafluoroethoxy)-2,2-difluoroethoxy)-(S)-2-fluoropropoxy)propyl chloride, was prepared by combining

Scheme 5

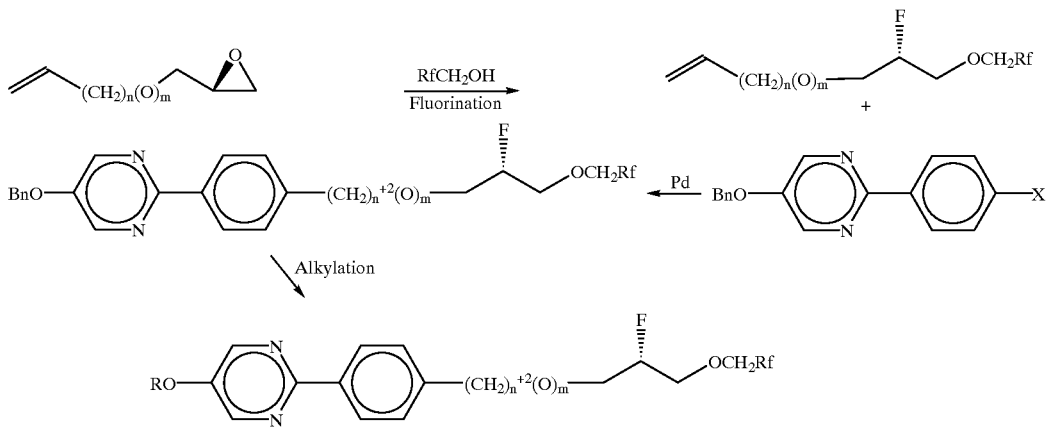

3-(2-(2-(nonafluorobutoxy)tetrafluoroethoxy)-2,2-difluoroethoxy)-(S)-2-fluoropropanol (20 g, 39.4 mmol) and 1-bromo-3-chloropropane (18.6 g, 118 mmol). The resulting compound (2.0 g, 3.4 mmol) was then combined with 5-heptyl-2-(4-hydroxyphenyl)pyrimidine (0.9 g, 3.4 mol) in acetonitrile/dimethyl formamide (1:1, 20 mL) using essentially the procedure of Example 8 of International Patent Publication No. WO 96/33251. The resulting crude product was further purified by chromatography, eluting with 30:1 toluene/ethyl acetate, followed by Kugelrohr distillation (180–90° C. at 0.01 torr; yield 0.96 g).

Example 204

Preparation of 5-Hexyloxy-2-[4-(3-(3-(2-(2-(nonafluorobutoxy)tetrafluoroethoxy)-2,2-difluoroethoxy)-(S)-2-fluoropropoxy)propoxy) phenyl]pyrimidine The title compound was prepared essentially as described in Example 8 of International Patent Publication No. WO 96/33251 by combining 3-(3-(2-(2-(nonafluorobutoxy) tetrafluoroethoxy)-2,2-difluoroethoxy)-(S)-2-fluoropropoxy)propyl chloride (3.0 g, 5.1 mmol) with 5-hexyloxy-2-(4-hydroxyphenyl)pyrimidine (1.4 g, 5.1 mmol). The resulting crude product was purified by Kugelrohr distillation (b.p. 170–80° C. at 0.01 torr).

Example 205

Preparation of 5-Octyloxy-2-[4-(4-(2-(2-(nonafluorobutoxy)tetrafluoroethoxy)-2,2-difluoroethoxy)-(S)-3-fluorobutoxy)phenyl] pyrimidine The starting material, 4-(2-(2-(nonafluorobutoxy) tetrafluoroethoxy)-2,2-difluoroethoxy)-(S)-3-fluorobutane-1-methanesulfonate, was prepared by the following procedure: 4-benzyloxy-(R)-1,2-epoxybutane (8.0 g, 44.9 mmol, prepared essentially as described by J. A. Frick in Synthesis 7, 621 (1992)) was combined with 2-(2-(nonafluorobutoxy) tetrafluoroethoxy)-2,2-difluoroethoxy (23.3 g, 53.9 mmol), potassium hydroxide (3.0 g, 53.9 mmol, aqueous) in tetrahydrofuran (3 mL) and refluxed for 3 hours to produce 4-(2-(2-(nonafluorobutoxy)tetrafluoroethoxy)-2,2-difluoroethoxy)-(R)-3-hydroxybutane-1-methanesulfonate. This (R)-hydroxy compound (20 g, 32.8 mmol) was treated with diethylaminosulfur tetrafluoride (6.3 g, 39.3 mmol) and was then hydrogenated using Pd(OH)$_2$ on carbon to remove the benzyl protecting group.

The title compound was prepared by combining 5-octyloxy-2-(4-hydroxyphenyl)pyrimidine (1.1 g, 3.8 mmol) and 4-(2-(2-(nonafluorobutoxy)tetrafluoroethoxy)-2, 2-difluoroethoxy)-(S)-3-fluorobutane-1-methanesulfonate (2.3 g, 3.8 mmol) using essentially the procedure of Example 8 of International Patent Publication No. WO 96/33251. The resulting crude product was further purified by chromatography, followed by Kugelrohr distillation (yield 1.92 g).

Example 206

Preparation of 5-Hexyloxy-2-[3-(4-(2-(2-(nonafluorobutoxy)tetrafluoroethoxy)-2,2-difluoroethoxy)-(S)-3-fluorobutoxy)propyl)phenyl] pyrimidine The title compound was prepared by adding (nonafluorobutoxy)tetrafluoroethoxy)-2,2-difluoroethoxy)-(S)-3-fluorobutoxy)prop-1-ene (3.5 g, 6.2 mmol, prepared by addition of 3-bromopropene to 4-(2-(2-(nonafluorobutoxy)tetrafluoroethoxy)-2,2-difluoroethoxy)-(S)-3-fluorobutanol) to a mixture of 5-hexyloxy-2-[trifluoromethylsulfonyloxyphenyl]pyrimidine (2.5 g, 6.22 mmol), 9-borabicyclononane (12.4 mL of 0.5 M in THF), PdCl$_2$dPPF ([1,1'-bis(diphenylphosphino)ferrocene] palladium(II) chloride, 50 mg, 0.062 mmol), and K$_3$PO$_4$ (2.8 g, 13.1 mmol) in dioxane (17 mL) at a temperature less than 5° C. After stirring the resulting mixture at 100° C. for 16 hours, water was added, and the mixture was extracted with toluene. The combined toluene extracts were dried, and the resulting crude product was purified by chromatography, eluting first with 10:1 then 4:1 hexanes/ethyl acetate, followed by Kugelrohr distillation (b.p. 180° C. at 0.01 torr; yield 0.95 g).

Example 207

Preparation of 5-Octyloxy-2-[1-(4-(2-(2-(nonafluorobutoxy) tetrafluoroethoxy)-2,2-difluoroethoxy)-(S)-3-fluorobutoxy)methyl)phenyl] pyrimidine The title compound was prepared by combining 2-(2-(nonafluorobutoxy)tetrafluoroethoxy)-2,2-difluoroethoxy)-(S)-3-fluorobutanol(2.0 g, 3.8 mmol), 5-octyloxy-2-[bromomethylphenyl]pyrimidine (prepared essentially as described in EP 474196, 1.44 g, 3.8 mmol), potassium hydroxide (0.21 g, 3.8 mmol), and Adogen™ 464 (0.15 g) in tetrahydrofuran and then heating the resulting mixture overnight at 75° C. The resulting crude product was purified by chromatography, eluting with 8:1 hexanes/ethyl acetate, followed by Kugelrohr distillation (yield 0.45 g).

Example 208

Preparation of 5-Hexyloxy-2-[4-(4-(2-( 2-(nonafluorobutoxy)tetrafluoroethoxy)-2,2-difluoroethoxy)-(S)-3-fluorobutoxy)butoxy)phenyl] pyrimidine The starting material, 4-(4-(2-(2-(nonafluorobutoxy) tetrafluoroethoxy)-2,2-difluoroethoxy)-(S)-3-fluorobutoxy) butyl bromide, was prepared by combining 1,4-dibromobutane (4.9 g, 22.8 mmol) with 2-(2-(nonafluorobutoxy)tetrafluoroethoxy)-2,2-difluoroethoxy)-(S)-3-fluorobutanol (4.0 g, 7.6 mmol). The title compound was prepared essentially as described in Example 8 of International Patent Publication No. WO 96/33251 by combining 4-(4-(2-(2-(nonafluorobutoxy)tetrafluoroethoxy)-2, 2-difluoroethoxy)-(S)-3-fluorobutoxy)butyl bromide (2.7 g, 4.1 mmol) with 5-hexyloxy-2-(4-hydroxyphenyl)pyrimidine (1.1 g, 4.1 mmol). The resulting crude product was purified by chromatography, eluting with 6:1 hexanes/ethyl acetate (yield 0.58 g).

Example 209

Preparation of 5-Octyl-2-[4-(4-(2-(2-(nonafluorobutoxy) tetrafluoroethoxy)-2,2-difluoroethoxy)-(S)-3-fluorobutoxy)butoxy)phenyl] pyrimidine The title compound was prepared essentially as described in Example 8 of International Patent Publication No. WO 96/33251 by combining 4-(4-(2-(2-(nonafluorobutoxy)

tetrafluoroethoxy)-2,2-difluoroethoxy)-(S)-3-fluorobutoxy) butyl bromide (2.6 g, 3.95 mmol) with 5-octyl-2-(4-hydroxyphenyl)pyrimidine (1.1 g, 3.95 mmol). The resulting crude product was purified by chromatography, eluting with 6:1 hexanes/ethyl acetate (yield 2.4 g).

Example 210

Preparation of 5-Heptyl-2-[4-(7-(2-(2-(nonafluorobutoxy)tetrafluoroethoxy)-2,2-difluoroethoxy)-(R)-6-fluoroheptyloxy)phenyl] pyrimidine The starting material, 7-(2-(2-(nonafluorobutoxy) tetrafluoroethoxy)-2,2-difluoroethoxy)-(R)-6-fluoroheptane-1-methanesulfonate, was prepared by the following procedure: 7-(2-(2-(nonafluorobutoxy) tetrafluoroethoxy)-2,2-difluoroethoxy)-(R)-6-fluorohept-1-ene (10 g, 18.8 mmol) was treated with $BH_3$. THF (9.4 mmol) in tetrahydrofuran, followed by oxidation with hydrogen peroxide (30% aqueous, 9.4 mmol) to produce the corresponding heptanol. This heptanol (8.9 g, 15.7 mmol) was treated with methanesulfonyl chloride (1.98 g, 17.3 mmol) to produce the methanesulfonate derivative The title compound was prepared by combining 5-heptyl-2-(4-hydroxyphenyl)pyrimidine (1.1 g, 3.8 mmol) and 4-(2-(2-(nonafluorobutoxy)tetrafluoroethoxy)-2,2-difluoroethoxy)-(S)-3-fluoropropoxy) butane-1-methanesulfonate (2.3 g, 3.8 mmol) essentially as described in Example 8 of International Patent Publication No. WO 96/33251. The resulting crude product was further purified by recrystallization from heptane, then from ethanol, followed by Kugelrohr distillation (b.p. 200° C. at 0.1 torr; yield 1.79 g).

Example 211

Preparation of 5-Hexyloxy-2-[4-(7-(2-(2-(nonafluorobutoxy)tetrafluoroethoxy)-2,2-difluoroethoxy)-(R)-6-fluoroheptyloxy)phenyl] pyrimidine The title compound was prepared by combining 5-hexyloxy-2-(4-hydroxyphenyl)pyrimidine (0.36 g, 1.32 mmol) and 4-(2-(2-(nonafluorobutoxy)tetrafluoroethoxy)-2,2-difluoroethoxy)-(S)-3-fluoropropoxy)butane-1-methanesulfonate (0.85 g, 1.32 mmol) essentially as described in Example 8 of International Patent Publication No. WO 96/33251. The resulting crude product was further purified by chromatography, eluting with 10:1 hexanes/ethyl acetate, followed by Kugelrohr distillation (b.p. 190–210° C. at 0.01 torr; yield 0.67 g).

Example 212

Preparation of 5-Octyloxy-2-[4-(7-(2-(2-(nonafluorobutoxy)tetrafluoroethoxy)-2,2-difluoroethoxy)-(R)-6-fluoroheptyloxy)-2,3-difluorophenyl]pyrimidine The title compound was prepared essentially as described in Example 211 by combining 5-octyloxy-2-(4-hydroxyphenyl)-2,3-difluoropyrimidine and 4-(2-(2-(nonafluorobutoxy)tetrafluoroethoxy)-2,2-difluoroethoxy)-(S)-3-fluoropropoxy)butane-1-methanesulfonate essentially as described in Example 8 of International Patent Publication No. WO 96/33251. The resulting crude product was further purified by chromatography, eluting with 10:1 hexanes/ethyl acetate, followed by Kugelrohr distillation.

Example 213

Preparation of 5-Octyloxy-2-[4-(7-(2-(2-(nonafluorobutoxy)tetrafluoroethoxy)-2,2-difluoroethoxy)-(R)-6-fluoroheptyloxy)-2,3-difluorophenyl]pyrimidine The title compound was prepared essentially as described in Example 211 by combining 5-octyloxy-2-(4-hydroxyphenyl)-3-fluoropyrimidine and 4-(2-(2-(nonafluorobutoxy)tetrafluoroethoxy)-2,2-difluoroethoxy)-(S)-3-fluoropropoxy)butane-1-methanesulfonate essentially as described in Example 8 of International Patent Publication No. WO 96/33251. The resulting crude product was further purified by chromatography, eluting with 10:1 hexanes/ethyl acetate, followed by Kugelrohr distillation.

Example 214

Preparation of 5-(2-(S)-Fluorodecyloxy-2-[4-(6-(2-(2-(nonafluorobutoxy)tetrafluoroethoxy)-2,2-difluoroethoxy)-(S)-5-fluorohexyl)phenyl]pyrimidine The title compound was prepared by adding (nonafluorobutoxy)tetrafluoroethoxy)-2,2-difluoroethoxy)-(S)-5-fluorohex-1-ene (4.0 g, 7.5 mmol) to a mixture of 5-(2-(S)-fluorodecyloxy-2-[6-(2-(2-(nonafluorobutoxy)tetrafluoroethoxy)-2,2-difluoroethoxy)-(S)-5-fluorohexyl) phenyl]pyrimidine (3.6 g, 7.5 mmol), 2-(2, 9-borabicyclononane (15 mL of 0.5 M in THF), $PdCl_2dPPF$ (60 mg, 0.075 mmol), and $K_3PO_4$ (3.3 g, 15.8 mmol) in dioxane (17 mL) at a temperature less than 5° C. After stirring the resulting mixture at room temperature overnight, water was added, and the mixture was extracted with toluene. The combined toluene extracts were dried, and the resulting crude product was purified by chromatography, eluting with 10:1 hexanes/ethyl acetate, followed by Kugelrohr distillation (b.p. 190–210° C. at 0.01 torr) and recrystallization from heptane (yield 2.2 g).

Example 215

Preparation of 5-Hexyloxy-2-[4-(3-(2-(2-(nonafluorobutoxy)tetrafluoroethoxy)-2,2-difluoroethoxy) )-(R)-2-fluoropropyloxy)-(R)-2-methylpropyloxy)phenyl]pyrimidine The starting material, 3-(2-(2-(nonafluorobutoxy) tetrafluoroethoxy)-2,2-difluoroethoxy))-(R)-2-fluoropropyloxy)-(R)-2-methylpropane-1-methanesulfonate, was prepared as follows: (S)-2-methyl-3-bromopropanol was alkylated with benzyl bromide to produce (S)-2-methyl-3-bromo-1-benzyloxypropane, which was then combined with 3-(2-(2-(nonafluorobutoxy) tetrafluoroethoxy)-2,2-difluoroethoxy))-(R)-2-fluoropropanol, followed by hydrogenation with 10% Pd/C to remove the benzyl protecting group. The title compound was prepared by combining 5-hexyloxy-2-(4-hydroxyphenyl)pyrimidine (0.7 g, 2.58 mmol) and 3-(2-(2-

(nonafluorobutoxy)tetrafluoroethoxy)-2,2-difluoroethoxy))-(R)-2-fluoropyloxy)-(R)-2-methylpropane-1-methanesulfonate (1.7 g, 2.58 mmol) essentially as described in Example 8 of International Patent Publication No. WO 96/33251. The resulting crude product was further purified by chromatography, eluting with 10:1 hexanes/ethyl acetate, and was recrystallized from heptane, followed by Kugelrohr distillation (b.p. 180–190° C. at 0.02 torr; yield 1.28 g).

Example 216

Preparation of 5-Heptyloxy-2-[4-(3-(2-(2-(nonafluorobutoxy)tetrafluoroethoxy)-2,2-difluoroethoxy))-(S)-1-(trifluoromethyl)ethyl)propyl)phenyl]pyrimidine The title compound was prepared by adding 3-(2-(2-(nonafluorobutoxy)tetrafluoroethoxy)-2,2-difluoroethoxy))-(S)-1-(trifluoromethyl)ethyl)prop-1-ene (6.0 g, 10.3 mmol, prepared by addition of 3-bromopropene to 2-(2-(2-(nonafluorobutoxy) tetrafluoroethoxy)-2,2-difluoroethoxy)-(S)-1-(trifluoromethyl)ethanol) to a mixture of 5-heptyloxy-2-[trifluoromethylsulfonyloxyphenyl]pyrimidine (4.3 g, 10.3 mmol), 9-borabicyclononane (20.6 mL of 0.5 M in THF), $PdCl_2dPPF$ (82 mg, 0.1 mmol), and $K_3PO_4$ (2.8 g, 13.1 mmol) in dioxane (17 mL) at a temperature less than 5° C. After stirring the resulting mixture at 100° C. for 16 hours, water was added, and the mixture was extracted with toluene. The combined toluene extracts were dried, and the resulting crude product was purified by chromatography, eluting with 10:1 hexanes/ethyl acetate, and was recrystallized from heptane, followed by Kugelrohr distillation (b.p. 160–70° C. at 0.02 torr; yield 3.04 g).

Example 217

Preparation of 5-Hexyloxy-2-[4-(2-(2-(2-(trifluoromethoxy)tetrafluoroethoxy)tetrafluoroethoxy)-2,2-difluoroethoxy)-(R)-8-fluorononyloxy)phenyl]pyrimidine The starting material, 2-(2-(2-(trifluoromethoxy)tetrafluoroethoxy)tetrafluoroethoxy)-2,2-difluoroethoxy)-(R)-8-fluorononyl-1-methanesulfonate, was prepared by hydroboration of 2-(2-(2-(trifluoromethoxy)tetrafluoroethoxy)tetrafluoroethoxy)-2,2-difluoroethoxy)-(R)-8-fluoronon-1-ene using $BH_3$ in tetrahydrofuran, followed by mesylation of the resulting nonanol. The title compound was prepared by combining 5-hexyloxy-2-(4-hydroxyphenyl)pyrimidine (2.0 g, 7.8 mmol) and 2-(2-(2-(trifluoromethoxy)tetrafluoroethoxy)tetrafluoroethoxy)-2,2-difluoroethoxy)-(R)-8-fluorononyl-1-methanesulfonate (4.9 g, 7.8 mmol) essentially as described in Example 8 of International Patent Publication No. WO 96/33251. The resulting crude product was further purified by recrystallization from hexanes, followed by chromatography (eluting with 10:1 hexanes/ethyl acetate) and then by Kugelrohr distillation (b.p. 185–95° C. at 0.01 torr; yield 2.3 g)

Example 218

Preparation of 5-Heptyloxy-2-(4-[5-(3-(2-(2-(nonafluorobutoxy)tetrafluoroethoxy)-2,2-difluoroethoxy))-(S)-2-(fluoropropoxy)-2,2,3,3,4,4-hexafluoropentyloxy)phenyl]pyrimidine The title compound was prepared essentially as in Example 97 of International Patent Publication No. 96/15092 by combining 5-heptyloxy-2-(4-hydroxyphenyl)pyrimidine with 5-(3-(2-(2-(nonafluorobutoxy)tetrafluoroethoxy)-2,2-difluoroethoxy))-(S)-2-(fluoropropoxy)-2,2,3,3,4,4-hexafluoropentyl-1-butanesulfonate. The resulting product was purified by chromatography, followed by Kugelrohr distillation (b.p. 200–5° C. at 0.008 torr).

Example 219

Preparation of 5-Heptyloxy-2-(4-[4-(3-(2-(2-(nonafluorobutoxy)tetrafluoroethoxy)- 2,2-difluoroethoxy))-(S)-2-(fluoropropoxy)-2,2,3,3,-tetrafluorobutyloxy)phenyl]pyrimidine The title compound was prepared essentially as in Example 97 of International Patent Publication No. 96/15092 by combining 5-heptyloxy-2-(4-hydroxyphenyl)pyrimidine with 4-(3-(2-(2-(nonafluorobutoxy)tetrafluoroethoxy)-2,2-difluoroethoxy))-(S)-2-(fluoropropoxy)-2,2,3,3-tetrafluorobutyl-1-butanesulfonate. The resulting product was purified by chromatography, followed by Kugelrohr distillation (b.p. 195–200° C. at 0.01 torr)

The compounds of the Examples were evaluated for transition temperatures by differential scanning calorimetry (DSC) and/or optical observation of material phase changes using a hot stage and a polarizing microscope. The transition temperatures (° C.) were obtained upon cooling through the isotropic state (I) to the smectic A mesophase ($S_A$), the smectic C mesophase ($S_C$), and higher order mesophases (M1 and M2) and are set forth in Table 1 below.

TABLE 1

| Ex. No. | Structure | I to $S_A$ | to $S_C$ | to $S_{M1}$ | to K | to $S_C$ | to $S_A$ |
|---|---|---|---|---|---|---|---|
| 1 | $C_8H_{17}$–pyridine–phenyl–$(CH_2)_6$–CHF–$CH_2OCH_2CF_2(OC_2F_4)_2OCF_3$ | 79.3 | 56.7 | −4.2 | | 22.2 | 59.2 |
| 2 | $C_4H_9O$–pyridine–phenyl–$(CH_2)_6$–CHF–$CH_2OCH_2CF_2OC_2F_4OC_3F_7$ | 90.9 | 61.3 | 41.5 | | 46.6 | 63.2 |
| 3 | $C_4H_9O$–pyridine–phenyl–$(CH_2)_6$–CHF–$CH_2OCH_2CF_2OC_2F_4OC_4F_9$ | 92.3 | 70.1 | 43.2 | | 48.2 | 72.5 |
| 4 | $C_4H_9O$–pyridine–phenyl–$(CH_2)_6$–CHF–$CH_2OC_2F_4OC_4F_9$ | 92.1 | 57.6 | 41.1 | | 52.8 | 59.5 |
| 5 | $C_5H_{11}O$–pyridine–phenyl–$(CH_2)_6$–CHF–$CH_2OCH_2CF_2OC_2F_4OCF_3$ | 83.4 | | 34.3 | | | 48.7 |
| 6 | $C_5H_{11}O$–pyridine–phenyl–$(CH_2)_6$–CHF–$CH_2OCH_2CF_2(OC_2F_4)_2OCF_3$ | 95 | 61 | 27.7 | | 37.7 | 63.3 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 7 | C$_5$H$_{11}$O—pyridine—phenyl—(CH$_2$)$_6$—CHF—CH$_2$OCH$_2$CF$_2$OC$_2$F$_4$OC$_2$F$_5$ | 89.6 | | 32.4 | | | 45.2 |
| 8 | C$_5$H$_{11}$O—pyridine—phenyl—(CH$_2$)$_6$—CHF—CH$_2$OCH$_2$C$_2$F$_4$OC$_2$F$_5$ | 84.1 | | 30 | | | 47.9 |
| 9 | C$_5$H$_{11}$O—pyridine—phenyl—(CH$_2$)$_6$—CHF—CH$_2$OCH$_2$C$_3$F$_6$OC$_2$F$_5$ | 95 | 50 | 38 | | | |
| 10 | C$_5$H$_{11}$O—pyridine—phenyl—(CH$_2$)$_6$—CHF—CH$_2$OCH$_2$CF$_2$OC$_2$F$_4$OC$_3$F$_7$ | 91.7 | 59.7 | 25.8 | | 34.1 | 62 |
| 11 | C$_5$H$_{11}$O—pyridine—phenyl—(CH$_2$)$_6$—CHF—CH$_2$OCH$_2$C$_3$F$_6$OC$_3$F$_7$ | 98.4 | 63.6 | 34 | | 42.7 | 65.9 |
| 12 | C$_5$H$_{11}$O—pyridine—phenyl—(CH$_2$)$_6$—CHF—CH$_2$OCH$_2$CF$_2$OC$_4$F$_9$ | 83.5 | | 29.9 | | | 42.9 |
| 13 | C$_5$H$_{11}$O—pyridine—phenyl—(CH$_2$)$_6$—CHF—CH$_2$OCH$_2$CF$_2$OC$_2$F$_4$OC$_4$F$_9$ | 93.1 | 69.6 | 27.4 | | 34.7 | 72.1 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 14 | C$_5$H$_{11}$O-pyrimidine-phenyl-(CH$_2$)$_6$-CHF-CH$_2$-OCH$_2$C$_2$F$_4$OC$_4$F$_9$ | 91.5 | 54.8 | 23.5 | | 40.8 | 57.6 |
| 15 | C$_6$H$_{12}$-pyrimidine-phenyl-(CH$_2$)$_6$-CHF-CH$_2$-OCH$_2$CF$_2$(OC$_2$F$_4$)$_2$OCF$_3$ | 72.8 | 40.9 | 21.4 | | 33.9 | 43.6 |
| 16 | C$_6$H$_{12}$-pyrimidine-phenyl-(CH$_2$)$_6$-CHF-CH$_2$-OCH$_2$C$_2$F$_4$OC$_4$F$_3$ | 67.2 | 31.5 | 17.2 | | 25 | 33.9 |
| 17 | C$_6$H$_{12}$-phenyl-phenyl-(CH$_2$)$_6$-CHF-CH$_2$-OCH$_2$CF$_2$OC$_2$F$_4$OC$_2$F$_5$ | 65.9 | | 26.1 | | | 40.5 |
| 18 | C$_6$H$_{12}$-pyrimidine-phenyl-(CH$_2$)$_6$-CHF-CH$_2$-OCH$_2$CF$_2$OC$_2$F$_4$OC$_3$F$_7$ | 67.7 | 38 | 18.2 | | 26.6 | 40.3 |
| 19 | C$_6$H$_{12}$-pyrimidine-phenyl-(CH$_2$)$_6$-CHF-CH$_2$-OCH$_2$CF$_2$OC$_2$F$_4$OC$_4$F$_9$ | 72.8 | 48.4 | 19.2 | | 26.1 | 51 |
| 20 | C$_6$H$_{12}$O-pyrimidine-phenyl-(CH$_2$)$_6$-CHF-CH$_2$-OCH$_2$CF$_2$OC$_2$F$_4$OCF$_3$ | 92 | | 14.9 | | | 31.3 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 21 | C$_6$H$_{12}$O—[pyridine]—[phenyl]—(CH$_2$)$_6$—CHF—CH$_2$—OCH$_2$CF$_2$(OC$_2$F$_4$)$_2$OCF$_3$ | 103.4 | 74.6 | 12.1 | | 33.4 | 76.2 |
| 22 | C$_6$H$_{12}$O—[pyridine]—[phenyl]—(CH$_2$)$_6$—CHF—CH$_2$—OCH$_2$CF$_2$(OC$_2$F$_4$)$_2$OCF$_3$ | 98.3 | 53 | 19.4 | | 41.5 | |
| 23 | C$_6$H$_{12}$O—[pyridine]—[phenyl]—(CH$_2$)$_6$—CHF—CH$_2$—OCH$_2$C$_2$F$_4$OC$_2$F$_5$ | 91.8 | | 13.5 | | | 27.2 |
| 24 | C$_6$H$_{12}$O—[pyridine]—[phenyl]—(CH$_2$)$_6$—CHF—CH$_2$—OCH$_2$CF$_2$OC$_2$F$_4$OC$_3$F$_7$ | 98.6 | 74.1 | 11.6 | | 30.5 | 76.3 |
| 25 | C$_6$H$_{12}$O—[pyridine]—[phenyl]—(CH$_2$)$_6$—CHF—CH$_2$—OCH$_2$C$_3$F$_6$OC$_3$F$_7$ | 103.1 | 69.6 | 15.3 | | 29.9 | 72 |
| 26 | C$_6$H$_{12}$O—[pyridine]—[phenyl]—(CH$_2$)$_6$—CHF—CH$_2$—OCH$_2$C$_2$F$_4$OC$_4$F$_9$ | 98.1 | 70.3 | 2.6 | | 17.6 | 72.6 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 27 | C7H15—pyridine—phenyl—(CH2)6—CHF—CH2—OCH2CF2(OC2F4)2OCF3 | 80.4 | 46.7 | 8 | | 24.8 | 49.4 |
| 28 | C7H15—pyridine—phenyl—(CH2)6—CHF—CH2—OCH2CF2OC2F4OC2F5 | 73 | 19 | 13 | | | 32 |
| 29 | C7H15—pyridine—phenyl—(CH2)6—CHF—CH2—OCH2CF2OC4F9 | 65.4 | 9 | 7 | | | 16.3 |
| 30 | C7H15—pyridine—phenyl—(CH2)6—CHF—CH2—OCH2C2F4OC4F9 | 78 | 53 | <RT | | | |
| 31 | C7H15—pyridine—phenyl—(CH2)6—CHF—CH2—OCH2CF2OC2F4OC4F9 | 73.1 | 35.2 | −1.7 | | 21.3 | 37.4 |
| 32 | C7H15O—pyridine—phenyl—(CH2)6—CHF—CH2—OCH2CF2OC2F4OCF3 | 92.4 | 58.1 | 5.9 | | 20 | 60.8 |
| 33 | C7H15O—pyridine—phenyl—(CH2)6—CHF—CH2—OCH2C2F4OCF3 | 100.3 | 74.7 | −15.1 | | 12.5 | 77.1 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 34 | C$_7$H$_{15}$O—[pyrimidine]—[phenyl]—(CH$_2$)$_6$—CHF—CH$_2$—OCH$_2$CF$_2$OC$_2$F$_4$OC$_2$F$_5$ | 98.7 | 75.5 | 0 | | 28.4 | 77.8 |
| 35 | C$_7$H$_{15}$O—[pyrimidine]—[phenyl]—(CH$_2$)$_6$—CHF—CH$_2$—OCH$_2$C$_2$F$_4$OC$_2$F$_5$ | 93.1 | 59.5 | 5 | | 21.6 | 62 |
| 36 | C$_7$H$_{15}$O—[pyrimidine]—[phenyl]—(CH$_2$)$_6$—CHF—CH$_2$—OCH$_2$C$_3$F$_6$OC$_2$F$_5$ | 100 | 73.6 | 18.1 | | 29.1 | 76.1 |
| 37 | C$_7$H$_{15}$O—[pyrimidine]—[phenyl]—(CH$_2$)$_6$—CHF—CH$_2$—OCH$_2$C$_3$F$_6$OC$_3$F$_7$ | 103.7 | 80.2 | 1.1 | | 21 | 82.4 |
| 38 | C$_7$H$_{15}$O—[pyrimidine]—[phenyl]—(CH$_2$)$_6$—CHF—CH$_2$—OCH$_2$CF$_2$OC$_4$F$_9$ | 90.8 | 67.6 | 1.1 | | 13.6 | 70.6 |
| 39 | C$_7$H$_{15}$O—[pyrimidine]—[phenyl]—(CH$_2$)$_6$—CHF—CH$_2$—OCH$_2$C$_2$F$_4$OC$_4$F$_9$ | 98.6 | 80.7 | −14.9 | | 15.3 | 82.8 |
| 40 | C$_8$H$_{17}$—[pyridine]—[phenyl]—(CH$_2$)$_6$—CHF—CH$_2$—OCH$_2$CF$_2$(OC$_2$F$_4$)$_2$OCF$_3$ | 78.7 | 50.4 | −4.5 | | 19.6 | 53.5 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 41 | C$_8$H$_{17}$–[pyridine]–[phenyl]–(CH$_2$)$_6$–CHF–CH$_2$–OCH$_2$C$_2$F$_4$OC$_2$F$_4$OCF$_3$ | 74 | 41 | −0.1 | | 22.5 | 45.1 |
| 42 | C$_8$H$_{17}$–[pyridine]–[phenyl]–(CH$_2$)$_8$–CHF–CH$_2$–OCH$_2$C$_2$F$_4$OC$_4$F$_9$ | 72.5 | 47 | −0.1 | | 24.5 | |
| 43 | C$_8$H$_{17}$O–[pyridine]–[phenyl]–(CH$_2$)$_8$–CHF–CH$_2$–OCH$_2$CF$_2$OC$_2$F$_5$ | 88.1 | 61.9 | −15.1 | | 29.5 | 64.4 |
| 44 | C$_8$H$_{17}$O–[pyridine]–[phenyl]–(CH$_2$)$_8$–CHF–CH$_2$–OCH$_2$C$_2$F$_4$OC$_2$F$_5$ | 95.5 | 79.9 | −12.1 | | 18.6 | 82.5 |
| 45 | C$_8$H$_{17}$O–[pyridine]–[phenyl]–(CH$_2$)$_6$–CHF–CH$_2$–OCH$_2$CF$_2$OC$_4$F$_9$ | 93.8 | 82.2 | −12.1 | | 20.9 | 84.6 |
| 46 | C$_8$H$_{17}$O–[pyridine]–[phenyl]–(CH$_2$)$_6$–CHF–CH$_2$–OCH$_2$CF$_2$OC$_2$F$_4$OC$_4$F$_9$ | 104.4 | 96.4 | −8 | | −0.2 | 98.7 |
| 48 | C$_4$H$_9$O–[pyridine]–[phenyl]–(CH$_2$)$_4$–CHF–CH$_2$–OCH$_2$CF$_2$OC$_2$F$_4$OC$_2$F$_5$ | 94.6 | 37 | 16.7 | | | 39 |

TABLE 1-continued
| Ex. No. | Structure | I to $S_A$ | to $S_C$ | to $S_{M1}$ | to K | to $S_C$ | to $S_A$ |
|---|---|---|---|---|---|---|---|
| 49 | 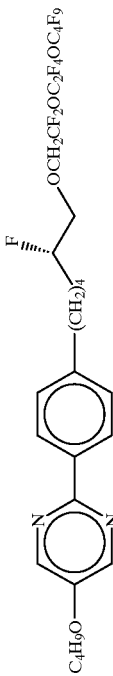 | 97.6 | 70.6 | 13.8 | | 27.1 | 72.9 |
| 50 | 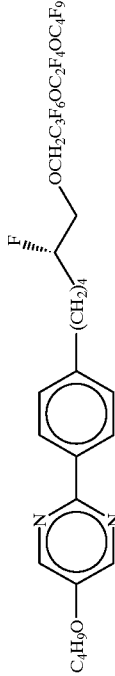 | 112.4 | 89.5 | 26.3 | | 30 | 91.9 |
| 51 | 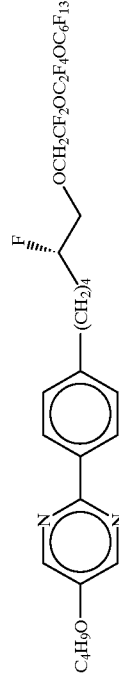 | 100.7 | 80.6 | 20.6 | | 42.9 | 83.2 |
| 52 | 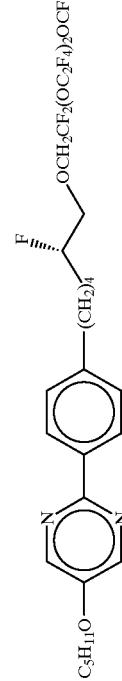 | 101.4 | 68.6 | −0.4 | | 28.9 | 71 |
| 53 | 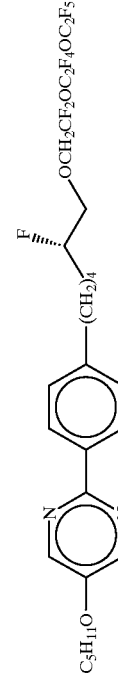 | 95.2 | 46.4 | 3.2 | | 38.5 | 49.1 |
| 54 | 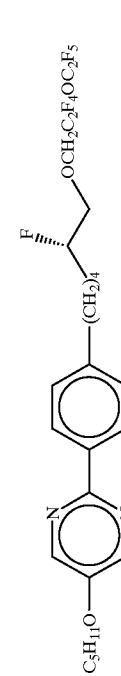 | 88.9 | 5 | −4.7 | | 31.3 | |
| 55 | 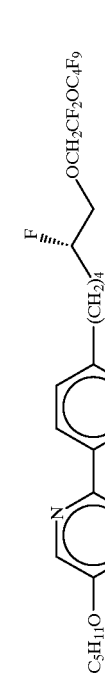 | 87.6 | 32 | −4.1 | | 32.1 | |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 56 | $C_5H_{11}O$–[pyridine]–[phenyl]–$(CH_2)_4$–CHF–$CH_2OCH_2C_3F_6OC_2F_4OC_4F_9$ | 112.1 | 89.3 | 43 | 0.7 | 7 | 91.5 |
| 57 | $C_5H_{11}O$–[pyridine]–[phenyl]–$(CH_2)_4$–CHF–$CH_2OCH_2C_2F_4OC_4F_9$ | 97.3 | 59.2 | −7.5 | | 33.7 | 61.6 |
| 58 | $C_5H_{11}O$–[pyridine]–[phenyl]–$(CH_2)_4$–CHF–$CH_2OCH_2CF_2OC_2F_4OC_6H_{12}$ | 101.3 | 80.4 | 15 | | 49.8 | 82.5 |
| 59 | $C_6H_{13}$–[pyridine]–[phenyl]–$(CH_2)_4$–CHF–$CH_2OCH_2CF_2OC_2F_4OC_4F_9$ | 74.1 | 42.7 | −8.1 | | 4.9 | 45.2 |
| 60 | $C_6H_{13}O$–[pyridine]–[phenyl]–$(CH_2)_4$–CHF–$CH_2OCH_2CF_2OC_2F_4OC_2F_5$ | 101.5 | 70.3 | −28 | | 29.2 | 72.7 |
| 61 | $C_6H_{13}O$–[pyridine]–[phenyl]–$(CH_2)_4$–CHF–$CH_2OCH_2C_3F_6OC_2F_5$ | 107.3 | 76.6 | −23.2 | | 7.6 | 79.1 |
| 62 | $C_6H_{13}O$–[pyridine]–[phenyl]–$(CH_2)_4$–CHF–$CH_2OCH_2CF_2OC_4F_9$ | 93.6 | 55 | −38.8 | | 9.7 | |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 63 | C$_6$H$_{13}$O–pyrimidine–phenyl–(CH$_2$)$_4$–CHF–CH$_2$–OCH$_2$CF$_2$OC$_2$F$_4$OC$_4$F$_9$ | 105.8 | 81.2 | −31.8 | | 5 | 83.1 |
| 64 | C$_6$H$_{13}$O–pyrimidine–phenyl–(CH$_2$)$_4$–CHF–CH$_2$–OCH$_2$C$_3$F$_6$OC$_2$F$_4$OC$_4$F$_9$ | 116.4 | 97.9 | 42 | −29 | −22 | 100.2 |
| 65 | C$_6$H$_{13}$O–pyrimidine–phenyl–(CH$_2$)$_4$–CHF–CH$_2$–OCH$_2$C$_2$F$_4$OC$_4$F$_9$ | 103.2 | 76.7 | −38.5 | | −28.7 | 78.8 |
| 66 | C$_6$H$_{13}$O–pyrimidine–phenyl–(CH$_2$)$_4$–CHF–CH$_2$–OCH$_2$CF$_2$OC$_2$F$_4$OC$_6$H$_{13}$ | 107.1 | 89.8 | −24.2 | | 23.7 | 92 |
| 67 | C$_7$H$_{15}$–pyridine–phenyl–(CH$_2$)$_4$–CHF–CH$_2$–OCH$_2$CF$_2$(OC$_2$F$_4$)$_2$OCF$_3$ | 81 | 48 | −23.9 | | 3.3 | 50.2 |
| 68 | C$_7$H$_{15}$–pyridine–phenyl–(CH$_2$)$_4$–CHF–CH$_2$–OCH$_2$CF$_2$OC$_2$F$_4$OC$_6$H$_{13}$ | 81.6 | 60.9 | −19.6 | | 18.7 | 63.3 |
| 69 | C$_7$H$_{15}$O–pyridine–phenyl–(CH$_2$)$_4$–CHF–CH$_2$–OCH$_2$C$_2$F$_4$OC$_2$F$_5$ | 94.3 | 70.4 | −22.5 | | −12.4 | 72.8 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 70 | C$_7$H$_{15}$O-[pyridine]-[phenyl]-(CH$_2$)$_4$-CHF-CH$_2$-OCH$_2$CF$_2$OC$_4$F$_9$ | 92.6 | 73 | −23 | | 14.8 | 75.4 |
| 71 | C$_7$H$_{15}$O-[pyridine]-[phenyl]-(CH$_2$)$_4$-CHF-CH$_2$-OCH$_2$C$_2$F$_4$OC$_4$F$_9$ | 99.7 | 83.1 | −19.9 | | −10.1 | 85.4 |
| 72 | C$_8$H$_{17}$-[pyridine]-[phenyl]-(CH$_2$)$_4$-CHF-CH$_2$-OCH$_2$CF$_2$OC$_2$F$_4$OC$_3$F$_7$ | 74.8 | 56.2 | <−30 | | 9 | 58.7 |
| 73 | C$_6$H$_{13}$O-[pyridine]-[phenyl]-(CH$_2$)$_5$-CHF-CH$_2$-OCH$_2$CF$_2$OC$_2$F$_4$OC$_4$F$_9$ | 105.8 | | −22.8 | | | 20.8 |
| 74 | C$_6$H$_{13}$O-[pyridine]-[phenyl]-(CH$_2$)$_5$-CHF-CH$_2$-OCH$_2$C$_3$F$_6$C$_4$F$_9$ | 109.9 | | −5.9 | | | 18.3 |
| 75 | C$_6$H$_{13}$O-[pyridine]-[phenyl]-(CH$_2$)$_5$-CHF-CH$_2$-OCH$_2$CF$_2$OC$_2$F$_4$OC$_6$F$_{13}$ | 108.3 | | 6.3 | | | 39.9 |
| 76 | C$_7$H$_{15}$-[pyridine]-[phenyl]-(CH$_2$)$_5$-CHF-CH$_2$-OCH$_2$CF$_2$OC$_2$F$_4$OC$_4$F$_9$ | 83.9 | | 11.8 | | | 34.7 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 77 | C7H15-pyridine-phenyl-(CH2)5-CHF-CH2-OCH2C3F6OC4H9 | 86.7 | | 17 | | | 34.9 |
| 78 | C7H15O-pyridine-phenyl-(CH2)5-CHF-CH2-OCH2CF2(OC2F4)2OCF3 | 108.1 | | −7.3 | | | 29.2 |
| 79 | C7H15O-pyridine-phenyl-(CH2)5-CHF-CH2-OCH2CF2OC2F4OC2F5 | 103 | | −5.2 | | | 36.7 |
| 80 | C7H15O-pyridine-phenyl-(CH2)5-CHF-CH2-OCH2CF2OC2F4OC4F9 | 107.9 | | −17.2 | | | 27.9 |
| 81 | C7H15O-pyridine-phenyl-(CH2)5-CHF-CH2-OCH2C2F4OC4F9 | 101.5 | 88.1 | −25.3 | | 15.8 | 88.6 |
| 82 | C7H15O-pyridine-phenyl-(CH2)5-CHF-CH2-OCH2C2F4OC4F9 | 102.3 | | −24.9 | | | 15.6 |
| 83 | C7H15O-pyridine-phenyl-(CH2)5-CHF-CH2-OCH2C3F6OC4F9 | 109.3 | | −9.8 | | | 24.3 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 84 | C$_7$H$_{15}$O—[pyridine]—[phenyl]—(CH$_2$)$_5$—CHF—CH$_2$—OCH$_2$CF$_2$OC$_2$F$_4$OC$_6$H$_{13}$ | 109.2 | 70.7 | 8.6 | | 43.5 | 73.7 |
| 85 | C$_8$H$_{17}$—[pyrazine]—[phenyl]—(CH$_2$)$_5$—CHF—CH$_2$—OCH$_2$CF$_2$(OC$_2$F$_4$)$_2$OCF$_3$ | 84 | | 14 | | | 36 |
| 86 | C$_8$H$_{17}$—[pyrazine]—[phenyl]—(CH$_2$)$_5$—CHF—CH$_2$—OCH$_2$CF$_2$OC$_2$F$_4$OC$_2$F$_5$ | 78.1 | | 17.8 | | | 44.3 |
| 87 | C$_8$H$_{17}$—[pyrazine]—[phenyl]—(CH$_2$)$_5$—CHF—CH$_2$—OCH$_2$CF$_2$OC$_2$F$_4$OC$_4$F$_9$ | 83.2 | | 14.5 | | | 36.8 |
| 88 | C$_8$H$_{17}$—[pyrazine]—[phenyl]—(CH$_2$)$_5$—CHF—CH$_2$—OCH$_2$C$_2$F$_4$OC$_4$F$_9$ | 77.4 | | 2.5 | | | 23.1 |
| 89 | C$_8$H$_{17}$—[pyrazine]—[phenyl]—(CH$_2$)$_5$—CHF—CH$_2$—OCH$_2$C$_2$F$_4$OC$_4$F$_9$ | 76.7 | | −2.5 | | | 20.8 |
| 90 | C$_8$H$_{17}$—[pyridine]—[phenyl]—(CH$_2$)$_5$—CHF—CH$_2$—OCH$_2$CF$_2$OC$_2$F$_4$OC$_6$F$_{13}$ | 86.3 | | 25.7 | | | 49 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 91 | C$_8$H$_{17}$O—[pyridine]—[phenyl]—(CH$_2$)$_5$—CHF—CH$_2$—OCH$_2$CF$_2$(OC$_2$F$_4$)$_2$OCF$_3$ | 110.3 | 66 | −17.7 | | 28.9 | |
| 92 | C$_8$H$_{17}$O—[pyridine]—[phenyl]—(CH$_2$)$_5$—CHF—CH$_2$—OCH$_2$CF$_2$OC$_2$F$_4$OC$_2$F$_5$ | 105.5 | 35 | −5.3 | | | 35.4 |
| 93 | C$_8$H$_{17}$O—[pyridine]—[phenyl]—(CH$_2$)$_5$—CHF—CH$_2$—OCH$_2$CF$_2$OC$_2$F$_4$OC$_4$F$_9$ | 108.3 | 72 | −18 | | 29.2 | |
| 94 | C$_8$H$_{17}$O—[pyridine]—[phenyl]—(CH$_2$)$_5$—CHF—CH$_2$—OCH$_2$CF$_2$OC$_2$F$_4$OC$_4$F$_9$ | 109.7 | 70 | −17.3 | | 28 | |
| 95 | C$_8$H$_{17}$O—[pyridine]—[phenyl]—(CH$_2$)$_5$—CHF—CH$_2$—OCH$_2$CF$_2$OC$_4$F$_9$ | 104.6 | 62.7 | −14.8 | | 21.5 | 65.7 |
| 96 | C$_8$H$_{17}$O—[pyridine]—[phenyl]—(CH$_2$)$_5$—CHF—CH$_2$—OCH$_2$CF$_2$OC$_4$F$_9$ | 104.2 | 58 | −15.1 | | 20.5 | |
| 97 | C$_{10}$H$_{21}$—[pyridine]—[phenyl]—(CH$_2$)$_7$—CHF—CH$_2$—OCH$_2$CF$_2$(OC$_2$F$_4$)$_2$OCF$_3$ | 86.6 | 43.3 | 25.7 | | | 49.6 |

TABLE 1-continued
| Ex. No. | Structure | I to $S_A$ | to $S_C$ | to $S_{M1}$ | to K | to $S_C$ | to $S_A$ |
|---|---|---|---|---|---|---|---|
| 98 | 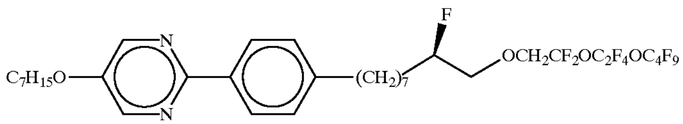 | 102.5 | 14 | | | 38.6 | |
| 99 | 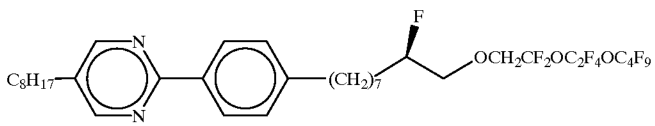 | 79.7 | 22.6 | | | 43.8 | |
| 100 | 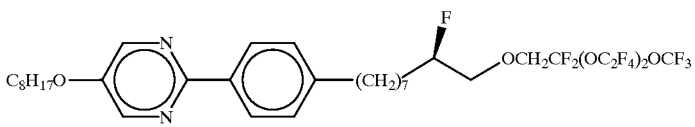 | 107.7 | 45 | 11.2 | | 39.2 | |
| 101 | 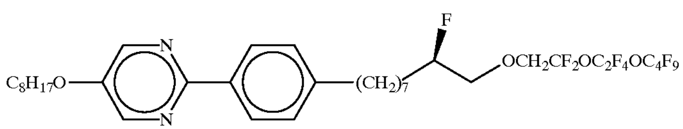 | 106.7 | 80 | 9.4 | | 37.8 | |
| 102 | 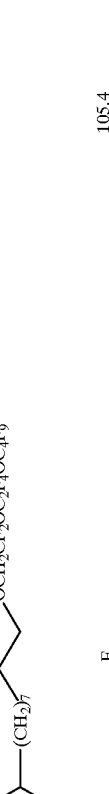 | 105.4 | −3.3 | −34 | | | 9.4 |
| 103 | 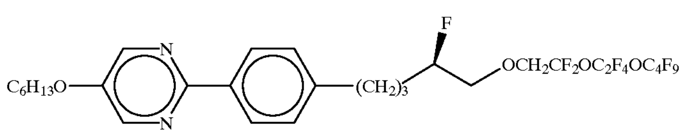 | 111.4 | −3.3 | <−30 | | | 8.5 |

TABLE 1-continued

| Ex. No. | Structure | I to S_A | to S_C | to S_M1 | to K | to S_C | to S_A |
|---|---|---|---|---|---|---|---|
| 104 | $C_7H_{15}O$—pyridine—phenyl—(CH$_2$)$_3$—CHF—CH$_2$—OCH$_2$CF$_2$(OC$_2$F$_4$)$_2$OCF$_3$ | 112.7 | 37 | −15.6 | | 23 | |
| 105 | $C_7H_{15}O$—pyridine—phenyl—(CH$_2$)$_3$—CHF—CH$_2$—OCH$_2$CF$_2$OC$_2$F$_4$OC$_3$F$_7$ | 109 | 38.8 | −13.5 | | 27.6 | 41 |
| 106 | $C_7H_{15}O$—pyridine—phenyl—(CH$_2$)$_3$—CHF—CH$_2$—OCH$_2$CF$_2$OC$_2$F$_4$OC$_4$F$_9$ | 109.9 | 77.1 | −15 | | 19 | 79.3 |
| 107 | $C_7H_{15}O$—pyridine—phenyl—(CH$_2$)$_3$—CHF—CH$_2$—OCH$_2$C$_2$F$_4$OC$_4$F$_9$ | 105.9 | 50.6 | −11.6 | | −6.1 | 53.6 |
| 108 | $C_8H_{17}O$—pyridine—phenyl—(CH$_2$)$_3$—CHF—CH$_2$—OCH$_2$CF$_2$(OC$_2$F$_4$)$_2$OCF$_3$ | 113.5 | 72.1 | −10.9 | | 23.7 | 73.9 |
| 109 | $C_8H_{17}O$—pyridine—phenyl—(CH$_2$)$_3$—CHF—CH$_2$—OCH$_2$CF$_2$OC$_2$F$_4$OC$_3$F$_7$ | 109.7 | 70.6 | −16.1 | | 30.1 | 73.2 |
| 110 | $C_8H_{17}O$—pyridine—phenyl—(CH$_2$)$_3$—CHF—CH$_2$—OCH$_2$C$_2$F$_4$OC$_4$F$_9$ | 106.4 | 73.6 | −7.1 | | 4.5 | 75.9 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 111 | $C_5H_{11}O$-pyridine-phenyl-$(CH_2)_8$-CHF-$CH_2OCH_2CF_2(OC_2F_4)_2OCF_3$ | 89.9 | 63.1 | 42.8 | | 47.6 | 65.4 |
| 112 | $C_5H_{11}O$-pyridine-phenyl-$(CH_2)_8$-CHF-$CH_2OCH_2CF_2OC_2F_4OC_4F_9$ | 90.5 | 64.9 | 36.8 | | 42.2 | 67.2 |
| 113 | $C_6H_{13}O$-pyridine-phenyl-$(CH_2)_8$-CHF-$CH_2OCH_2CF_2(OC_2F_4)_2OCF_3$ | 98 | 73.6 | 30.4 | 40.2 | 75.9 | |
| 114 | $C_6H_{13}O$-pyridine-phenyl-$(CH_2)_8$-CHF-$CH_2OCH_2CF_2OC_2F_4OC_2F_5$ | 91.2 | 33 | 31.2 | | | 45.6 |
| 115 | $C_6H_{13}O$-pyridine-phenyl-$(CH_2)_8$-CHF-$CH_2OCH_2C_3F_6OC_3F_7$ | 96.4 | 62.8 | 35.2 | | 42.3 | 64.5 |
| 116 | $C_6H_{13}O$-pyridine-phenyl-$(CH_2)_8$-CHF-$CH_2OCH_2CF_2OC_2F_4OC_4F_9$ | 96.2 | 80.7 | 28.5 | | 37.1 | 83.2 |
| 117 | $C_7H_{15}$-pyridine-phenyl-$(CH_2)_8$-CHF-$CH_2OCH_2C_3F_6OC_3F_7$ | 75.3 | 46.5 | 28.4 | | 35.2 | 48.2 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 118 | C$_7$H$_{15}$O—[pyridine]—[phenyl]—(CH$_2$)$_8$—CHF—CH$_2$—OCH$_2$CF$_2$(OC$_2$F$_4$)$_2$OCF$_3$ | 95 | 77.2 | 23.5 | | 39.2 | 79.3 |
| 119 | C$_7$H$_{15}$O—[pyridine]—[phenyl]—(CH$_2$)$_8$—CHF—CH$_2$—OCH$_2$CF$_2$OC$_2$F$_4$OC$_2$F$_5$ | 93.5 | 68 | 18.8 | | 46.6 | 69.8 |
| 120 | C$_7$H$_{15}$O—[pyridine]—[phenyl]—(CH$_2$)$_8$—CHF—CH$_2$—OCH$_2$C$_2$F$_4$OC$_2$F$_5$ | 86 | 37 | 15.5 | | 26.8 | |
| 121 | C$_7$H$_{15}$O—[pyridine]—[phenyl]—(CH$_2$)$_8$—CHF—CH$_2$—OCH$_2$C$_3$F$_6$OC$_2$F$_5$ | 94.8 | 61.5 | 31.1 | | 38.6 | 60.9 |
| 122 | C$_7$H$_{15}$O—[pyridine]—[phenyl]—(CH$_2$)$_8$—CHF—CH$_2$—OCH$_2$C$_3$F$_5$OC$_3$F$_7$ | 97.9 | 75.8 | 25.3 | | 34.1 | 77.5 |
| 123 | C$_7$H$_{15}$O—[pyridine]—[phenyl]—(CH$_2$)$_8$—CHF—CH$_2$—OCH$_2$CF$_2$OC$_4$F$_9$ | 88.1 | 57.3 | 22.5 | | 41.4 | 59.9 |
| 124 | C$_8$H$_{17}$—[pyridine]—[phenyl]—(CH$_2$)$_8$—CHF—CH$_2$—OCH$_2$CF$_2$(OC$_2$F$_4$)$_2$OCF$_3$ | 77.6 | 59.9 | 9.2 | | 34 | 81.1 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 125 | C$_8$H$_{17}$—[pyridine]—[phenyl]—(CH$_2$)$_8$—CHF—CH$_2$—OCH$_2$CF$_2$OC$_2$F$_4$OC$_2$F$_5$ | 71.1 | 30 | 15.6 | | | 36.1 |
| 126 | C$_8$H$_{17}$—[pyridine]—[phenyl]—(CH$_2$)$_8$—CHF—CH$_2$—OCH$_2$C$_3$F$_6$OC$_3$F$_7$ | 74.5 | 49.8 | 22 | | 36 | 51.5 |
| 127 | C$_8$H$_{17}$—[pyridine]—[phenyl]—(CH$_2$)$_8$—CHF—CH$_2$—OCH$_2$CF$_2$OC$_4$F$_9$ | 64.5 | 26.4 | 21 | | | 32.6 |
| 128 | C$_8$H$_{17}$O—[pyridine]—[phenyl]—(CH$_2$)$_8$—CHF—CH$_2$—OCH$_2$CF$_2$OC$_2$F$_4$OC$_2$F$_5$ | 97.9 | 85.1 | 8.9 | | 37.7 | 87.4 |
| 129 | C$_8$H$_{17}$O—[pyridine]—[phenyl]—(CH$_2$)$_8$—CHF—CH$_2$—OCH$_2$C$_2$F$_4$OC$_2$F$_5$ | 93 | 69.6 | −3.5 | | 30.4 | 71.3 |
| 130 | C$_8$H$_{17}$O—[pyridine]—[phenyl]—(CH$_2$)$_8$—CHF—CH$_2$—OCH$_2$C$_3$F$_6$OC$_2$F$_5$ | 97.9 | 85.1 | 8.9 | | 37.7 | 87.4 |
| 131 | C$_8$H$_{17}$O—[pyridine]—[phenyl]—(CH$_2$)$_8$—CHF—CH$_2$—OCH$_2$C$_3$F$_6$OC$_3$F$_7$ | 101.4 | 89.2 | 11.7 | | 29.8 | 90.5 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 132 | $C_8H_{17}O$–pyridine–phenyl–$(CH_2)_8$–CHF–$CH_2OCH_2CF_2OC_4F_9$ | 92.7 | 79.3 | 6 | | 20 | 81.5 |
| 133 | $C_8H_{17}O$–pyridine–phenyl–$(CH_2)_8$–CHF–$CH_2OCH_2CF_2OC_2F_4OC_4F_9$ | 103 | 93.7 | 12.9 | | 32.9 | 95.6 |
| 134 | $C_9H_{19}$–pyridine–phenyl–$(CH_2)_8$–CHF–$CH_2OCH_2CF_2OC_2F_4OC_2F_5$ | 76.7 | 48 | 26.8 | | 36.9 | |
| 135 | $C_9H_{19}$–pyridine–phenyl–$(CH_2)_8$–CHF–$CH_2OCH_2C_3F_8OC_3F_7$ | 80 | 60 | 23.5 | 15.6 | 41.4 | 64 |
| 136 | $C_9H_{19}$–pyridine–phenyl–$(CH_2)_8$–CHF–$CH_2OCH_2CF_2OC_4F_8$ | 70.3 | 38 | 14.8 | | 32.6 | |
| 137 | $C_5H_{11}O$–pyridine–phenyl–$(CH_2)_{10}$–CHF–$CH_2OCH_2CF_2(OC_2F_4)_2OCF_3$ | 86.3 | 64.9 | 45.6 | | 50.7 | 67.3 |
| 138 | $C_6H_{13}O$–pyridine–phenyl–$(CH_2)_{10}$–CHF–$CH_2OCH_2CF_2(OC_2F_4)_2OCF_3$ | 94.3 | 67 | 35 | | | 40.4 |

TABLE 1-continued

| Ex. No. | Structure | I to S_A | to S_C | to S_M1 | to K | to S_C | to S_A |
|---|---|---|---|---|---|---|---|
| 139 | C8H17-pyridine-phenyl-(CH2)10-CHF-CH2-OCH2CF2(OC2F4)2OCF3 | 77.6 | 59.9 | 9.2 | | 34 | 81.1 |
| 140 | C9H19O-pyridine-phenyl-C6H12CHCH2OCH2C2F4OCF3 (F) | 88.3 | 79.2 | 15.4 | | 37.5 | 80.4 |
| 141 | C6H13O-pyridine-phenyl-(CH2)8-CHF-CH2-OCH2CF2OC2F5 | 82.6 | | 23.5 | | | 37.7 |
| 142 | C6H13O-pyridine-phenyl-(CH2)6-CHF-CH2-OCH2C3F6OC2F5 | 99.2 | 51 | 21.3 | | 38.3 | |
| 143 | C6H13O-pyridine-phenyl-(CH2)6-CHF-CH2-OCH2CF2OC4F9 | 90 | 27 | 8.8 | | | 29 |
| 144 | C8H17-pyridine-phenyl-(CH2)6-CHF-CH2-OCH2CF2OC2F4OC4F9 | 76.9 | 59.5 | −5.7 | | 14.5 | 62 |
| 145 | C6H13O-pyridine-phenyl-(CH2)6-CHF-CH2-OCH2CF2OC2F4OC4F9 | 100.2 | 82.5 | 9.1 | | 18.9 | 84.8 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 146 | C$_8$H$_{17}$O–[pyrimidine]–[phenyl]–(CH$_2$)$_6$–CHF–CH$_2$–OCH$_2$CF$_2$OC$_2$F$_4$OCF$_3$ | 96 | 74 | | | | |
| 147 | C$_8$H$_{17}$O–[pyrimidine]–[phenyl]–(CH$_2$)$_6$–CHF–CH$_2$–OCH$_2$CF$_2$(OC$_2$F$_4$)$_2$OCF$_3$ | 106.1 | 95.6 | −8.8 | | 9.1 | 97.8 |
| 148 | C$_8$H$_{17}$O–[pyrimidine]–[phenyl]–(CH$_2$)$_6$–CHF–CH$_2$–OCH$_2$C$_3$F$_7$ | 88 | 61 | | | | |
| 149 | C$_8$H$_{17}$O–[pyrimidine]–[phenyl]–(CH$_2$)$_6$–CHF–CH$_2$–OCH$_2$C$_2$F$_4$OC$_4$F$_9$ | 100.8 | 90.9 | −8.2 | | 13.6 | 93.4 |
| 150 | C$_{10}$H$_{21}$–[pyrimidine]–[phenyl]–(CH$_2$)$_4$–CHF–CH$_2$–OCH$_2$CF$_2$OC$_2$F$_4$OCF$_3$ | 64.80 | 59.1 | −4.4 | 19.3 | 25.1 | 61.6 |
| 151 | C$_5$H$_{11}$O–[pyrimidine]–[phenyl]–(CH$_2$)$_4$–CHF–CH$_2$–OCH$_2$CF$_2$OC$_2$F$_4$OCF$_3$ | 96.3 | 68.7 | | | 25.6 | 71.7 |
| 152 | C$_6$H$_{13}$–[pyrimidine]–[phenyl]–(CH$_2$)$_4$–CHF–CH$_2$–OCH$_2$CF$_2$(OC$_2$F$_4$)$_2$OCF$_3$ | 75.2 | 32.3 | −8.7 | | 5.1 | 34.6 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 153 | C$_6$H$_{13}$-pyridine-phenyl-(CH$_2$)$_4$-CHF-CH$_2$-OCH$_2$CF$_2$OC$_2$F$_4$OC$_2$F$_5$ | 67.9 | 19 | −8.4 | | 12.6 | |
| 154 | C$_6$H$_{13}$O-pyridine-phenyl-(CH$_2$)$_4$-CHF-CH$_2$-OCH$_2$CF$_2$OC$_2$F$_4$OCF$_3$ | 96.1 | 40 | −32 | | 8.7 | |
| 155 | C$_6$H$_{13}$O-pyridine-phenyl-(CH$_2$)$_4$-CHF-CH$_2$-OCH$_2$CF$_2$(OC$_2$F$_4$)$_2$OCF$_3$ | 106.1 | 83.2 | −27.4 | | 22.8 | 85.7 |
| 156 | C$_6$H$_{13}$O-pyridine-phenyl-(CH$_2$)$_4$-CHF-CH$_2$-OCH$_2$CF$_2$OC$_2$F$_4$OC$_3$F$_7$ | 102.1 | 79.2 | −27.3 | | 20.9 | 81.7 |
| 157 | C$_7$H$_{15}$-pyridine-phenyl-(CH$_2$)$_4$-CHF-CH$_2$-OCH$_2$CF$_2$OC$_2$F$_4$OC$_4$F$_9$ | 78.4 | 55.2 | −24.5 | | 2.7 | 57.6 |
| 158 | C$_8$H$_{17}$-pyridine-phenyl-(CH$_2$)$_4$-CHF-CH$_2$-OCH$_2$CF$_2$(OC$_2$F$_4$)$_2$OCF$_3$ | 79.00 | 57.5 | | −29.8 | 9.9 | |
| 159 | C$_8$H$_{17}$-pyridine-phenyl-(CH$_2$)$_4$-CHF-CH$_2$-OCH$_2$CF$_2$OC$_2$F$_5$ | 55.9 | 12 | −24.5 | | | 16.4 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 160 | C$_8$H$_{17}$–pyridine–phenyl–(CH$_2$)$_4$–CHF–CH$_2$–OCH$_2$CF$_2$OC$_2$F$_4$OC$_2$F$_5$ | 72.00 | 47.6 | | | 15.7 | |
| 161 | C$_8$H$_{17}$–pyridine–phenyl–(CH$_2$)$_4$–CHF–CH$_2$–OCH$_2$CF$_2$OC$_2$F$_4$OC$_4$F$_9$ | 79.50 | 62.00 | −25.40 | −25 | −10.40 | |
| 162 | C$_8$H$_{17}$–pyridine–phenyl–(CH$_2$)$_4$–CHF–CH$_2$–OCH$_2$C$_2$F$_4$OC$_4$F$_9$ | 73.20 | 55.1 | | | 25.4 | |
| 163 | C$_8$H$_{17}$O–pyridine–phenyl–(CH$_2$)$_4$–CHF–CH$_2$–OCH$_2$CF$_2$OC$_2$F$_4$OCF$_3$ | 94.6 | 81.6 | −16.7 | −29 | −9.8 | 84 |
| 164 | C$_4$H$_9$O–pyridine–phenyl–(CH$_2$)$_4$–O–CH$_2$–CHF–CH$_2$–OCH$_2$CF$_2$(OC$_2$F$_4$)$_2$OCF$_3$ | 73.9 | 35.3 | −22.9 | | | 28.9 |
| 165 | C$_4$H$_9$O–pyridine–phenyl–(CH$_2$)$_4$–O–CH$_2$–CHF–CH$_2$–OCH$_2$CF$_2$OC$_2$F$_4$OC$_4$F$_9$ | 71.8 | 35.3 | −21.6 | | 26.6 | 39.8 |
| 166 | C$_4$H$_9$O–pyridine–phenyl–(CH$_2$)$_4$–O–CH$_2$–CHF–CH$_2$–OCH$_2$C$_5$F$_{10}$OC$_5$F$_{11}$ | 91.6 | 57.6 | 12.6 | | 20 | 60.3 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 167 | C$_5$H$_{11}$O-pyridine-phenyl-(CH$_2$)$_4$-O-CHF-CH$_2$-OCH$_2$CF$_2$(OC$_2$F$_4$)$_2$OCF$_3$ | 76.8 | 4 | <-40 | | | 20 |
| 168 | C$_5$H$_{11}$O-pyridine-phenyl-(CH$_2$)$_4$-O-CHF-CH$_2$-OCH$_2$CF$_2$OC$_2$F$_4$OC$_4$F$_9$ | 74.7 | 40 | -36.5 | 22.4 | 43.7 | |
| 169 | C$_6$H$_{13}$O-pyridine-phenyl-(CH$_2$)$_4$-O-CHF-CH$_2$-OCH$_2$CF$_2$(OC$_2$F$_4$)$_2$OCF$_3$ | 84.4 | 56 | <-35 | | -34.7 | |
| 170 | C$_6$H$_{13}$O-pyridine-phenyl-(CH$_2$)$_4$-O-CHF-CH$_2$-OCH$_2$C$_6$F$_{10}$OC$_2$F$_4$OCF$_3$ | 94.5 | 62.8 | <-47 | | | 65.3 |
| 171 | C$_6$H$_{13}$O-pyridine-phenyl-(CH$_2$)$_4$-O-CHF-CH$_2$-OCH$_2$C$_3$F$_6$OC$_2$F$_5$ | 76.7 | | <-47 | | | |
| 172 | C$_6$H$_{13}$O-pyridine-phenyl-(CH$_2$)$_4$-O-CHF-CH$_2$-OCH$_2$C$_3$F$_6$OC$_3$F$_7$ | 80.2 | 25 | <-47 | | | |
| 173 | C$_6$H$_{13}$O-pyridine-phenyl-(CH$_2$)$_4$-O-CHF-CH$_2$-OCH$_2$CF$_2$OC$_2$F$_4$OC$_4$F$_9$ | 82 | 63.5 | -44.5 | | -32 | 65.8 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 174 | C$_6$H$_{13}$O-pyridine-phenyl-(CH$_2$)$_4$-O-CH(F)-CH$_2$-OCH$_2$C$_3$F$_6$OC$_4$F$_9$ | 84.3 | 55.7 | <−47 | | −35.5 | 58.2 |
| 175 | C$_6$H$_{13}$O-pyridine-phenyl-(CH$_2$)$_4$-O-CH(F)-CH$_2$-OCH$_2$C$_7$F$_{15}$ | 83.1 | | −14.8 | | | 36.2 |
| 176 | C$_4$H$_9$O-pyridine-phenyl-(CH$_2$)$_6$-O-CH(F)-CH$_2$-OCH$_2$CF$_2$OC$_2$F$_4$OC$_4$F$_9$ | 70.7 | 49.1 | 10.1 | | 14.7 | 50.5 |
| 177 | C$_5$H$_{11}$O-pyridine-phenyl-(CH$_2$)$_6$-O-CH(F)-CH$_2$-OCH$_2$CF$_2$OC$_2$F$_4$OC$_4$F$_9$ | 73.8 | 50.1 | −9.6 | | 17 | 52.1 |
| 178 | C$_6$H$_{13}$O-pyridine-phenyl-(CH$_2$)$_6$-O-CH(F)-CH$_2$-OCH$_2$CF$_2$OC$_2$F$_4$OC$_2$F$_5$ | 78.3 | | −40.2 | | | 5.7 |
| 179 | C$_6$H$_{13}$O-pyridine-phenyl-(CH$_2$)$_6$-O-CH(F)-CH$_2$-OCH$_2$C$_3$F$_6$OC$_3$F$_7$ | 80.3 | | −35.9 | | | 6.4 |
| 180 | C$_6$H$_{13}$O-pyridine-phenyl-(CH$_2$)$_6$-O-CH(F)-CH$_2$-OCH$_2$CF$_2$OC$_2$F$_4$OC$_4$F$_9$ | 83.1 | 69.8 | <−40 | | 0.7 | 71.2 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 181 | C6H13O–[pyridine]–[phenyl]–(CH2)6–O–CHF–CH2–OCH2C3F6OC4F9 | 84.3 | 57.4 | −34.5 | | 6.8 | 59.8 |
| 182 | C7H15O–[pyridine]–[phenyl]–(CH2)6–O–CHF–CH2–OCH2CF2(OC2F4)2OCF3 | 86.3 | 73.7 | −20.3 | | −12.6 | 75.9 |
| 183 | C7H15O–[pyridine]–[phenyl]–(CH2)6–O–CHF–CH2–OCH2CF2OC2F4OC2F5 | 79.1 | 58 | −23.3 | | 6.6 | |
| 184 | C7H15O–[pyridine]–[phenyl]–(CH2)6–O–CHF–CH2–OCH2C3F6OC3F7 | 80.3 | 55 | −24.7 | | 7.8 | 58.6 |
| 185 | C8H17O–[pyridine]–[phenyl]–(CH2)6–O–CHF–CH2–OCH2CF2OC2F4OC2F9 | 78 | 70.4 | −33 | | 11.9 | 72.6 |
| 186 | C9H19O–[pyridine]–[phenyl]–(CH2)6–O–CHF–CH2–OCH2CF2OC2F4OC2F5 | 77.6 | 74 | 0.6 | −11.2 | 3.2 | 77.3 |
| 187 | C5H11O–[pyridine]–[phenyl]–(CH2)6–O–CHF–CH2–OCH2CF2OC2F4OC4F9 | 73/71 | 54.4 | 8.7 | | 15.6 | 56.6 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 188 | CH₃OC₆H₁₂O–[pyridine]–[phenyl]–(CH₂)₆–O–CH₂CHF–CH₂–OCH₂CF₂(OC₂F₄)₂OCF₃ | 93.5 | 34.4 | <–47 | | <47 | 86.9 |
| 189 | C₂H₆OC₂H₄O–[pyridine]–[phenyl]–(CH₂)₆–O–CH₂CHF–CH₂–OCH₂CF₂(OC₂F₄)₂OCF₃ | 61.9 | 54.4 | 16.3 | | 21.8 | 56.5 |
| 190 | C₆H₁₃OC₂H₄O–[pyridine]–[phenyl]–(CH₂)₆–O–CH₂CHF–CH₂–OCH₂CF₂(OC₂F₄)₂OCF₃ | 55.2 | 47.2 | 8.2 | | 22.1 | 50.1 |
| 191 | C₄H₉OC₄H₆O–[pyridine]–[phenyl]–(CH₂)₆–O–CH₂CHF–CH₂–OCH₂CF₂(OC₂F₄)₂OCF₃ | 69.2 | 61.3 | –22.2 | –29.4 | –8.6 | 63.9 |
| 192 | C₂F₅OC₃F₆CH₂OC₄H₆O–[pyridine]–[phenyl]–C₆H₁₂CHFCH₂OCH₂CF₂OC₂F₄OC₄F₉ | 61.6 | 57 | 4.2 | | 16.4 | |
| 193 | C₄F₉OC₂F₄OCF₂CH₂OC₃H₆O–[pyridine]–[phenyl]–C₆H₁₂CHFCH₂OCH₂CF₂OC₂F₄OC₄F₉ | 32 | 24 | –14 | | 12.5 | 26.6 |
| 194 | (CH₃)₂CHC₅H₁₀O–[pyridine]–[phenyl]–C₆H₁₂OCH₂CHFCH₂OCH₂CF₂OC₂F₄OC₄F₅ | 69.6 | 63 | | 16.2 | 17.8 | 65 |

TABLE 1-continued

| Ex. No. | Structure | I to S$_A$ | to S$_C$ | to S$_{M1}$ | to K | to S$_C$ | to S$_A$ |
|---|---|---|---|---|---|---|---|
| 195 | CH$_3$OC$_4$H$_8$O—[pyridine]—[phenyl]—C$_6$H$_{12}$OCH$_2$CHCH$_2$OCH$_2$CF$_2$OC$_2$F$_4$OC$_2$F$_5$ (F) | 78.8 | 51.8 | −19 | | 10.5 | 55 |
| 196 | C$_2$H$_5$OC$_3$H$_6$O—[pyridine]—[phenyl]—C$_6$H$_{12}$OCH$_2$CHCH$_2$OCH$_2$CF$_2$O(C$_2$F$_4$O)$_2$CF$_3$ (F) | 50 | 37.1 | | <5 | | |
| 197 | CH$_3$OC$_4$H$_8$O—[pyridine]—[phenyl]—C$_6$H$_{12}$OCH$_2$CHCH$_2$OCH$_2$CF$_2$O(C$_2$F$_4$O)$_2$CF$_3$ (F) | 56.7 | 38.6 | 9.8 | 2.9 | 23.8 | 40.7 |
| 198 | C$_2$H$_5$OC$_2$H$_4$O—[pyridine]—[phenyl]—C$_6$H$_{12}$OCH$_2$CHCH$_2$OCH$_2$CF$_2$O(C$_2$F$_4$O)$_2$CF$_3$ (F) | 61.9 | 54.4 | 16.3 | | 21.8 | 56.5 |
| 199 | CH$_3$OC$_4$H$_8$O—[pyridine]—[phenyl]—C$_6$H$_{12}$OCH$_2$CHCH$_2$OCH$_2$CF$_2$O(C$_2$F$_4$O)$_2$CF$_3$ (F) | 85.4 | 71.1 | −0.9 | | 10.1 | 73.1 |
| 200 | CF$_3$CH$_2$OC$_4$H$_8$O—[pyridine]—[phenyl]—C$_6$H$_{12}$OCH$_2$CHCH$_2$OCH$_2$CF$_2$OC$_2$F$_4$OC$_4$F$_9$ (F) | 86.7 | 78.1 | −5 | | 22.7 | 80.4 |
| 201 | C$_5$F$_{11}$CH$_2$OC$_3$H$_6$O—[pyridine]—[phenyl]—C$_6$H$_{12}$OCH$_2$CHCH$_2$OCH$_2$CF$_2$OC$_2$F$_4$OC$_4$F$_9$ (F) | | 47.1 | −2 | | 13.3 | |
| 202 | C$_8$H$_{17}$O—[pyridine]—[phenyl]—OC$_2$H$_4$OCH$_2$CHCH$_2$OCH$_2$CF$_2$OC$_2$F$_4$OC$_4$F$_9$ (F) | 108.9 | 93.6 | −19.9 | | 39.2 | |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 203 | $C_7H_{15}$—[pyridine]—[phenyl]—O—CH₂CH₂—O—CH₂—CHF—CH₂—OCH₂CF₂OC₂F₄OC₄F₉ | 73 | | −41.9 | | | −31.5 |
| 204 | $C_6H_{13}O$—[pyridine]—[phenyl]—O—CH₂CH₂—O—CH₂—CHF—CH₂—OCH₂CF₂OC₂F₄OC₄F₉ | 99.5 | 77.8 | −14.5 | | −1.6 | 80.3 |
| 205 | $C_8H_{17}O$—[pyridine]—[phenyl]—O—CH₂CH₂—CHF—CH₂—OCH₂CF₂OC₂F₄OC₄F₉ | 129.7 | 80.4 | −5 | | 17.6 | 82.8 |
| 206 | $C_6H_{13}O$—[pyridine]—[phenyl]—CH₂CH₂CH₂—O—CH₂—CHF—CH₂—OCH₂CF₂OC₂F₄OC₄F₉ | 82 | 70.6 | −39.5 | | −30.8 | 73 |
| 207 | $C_8H_{17}O$—[pyridine]—[phenyl]—CH₂—O—CH₂—CHF—CH₂—OCH₂CF₂OC₂F₄OC₄F₉ | 81 | 68 | <RT | | | |

TABLE 1-continued
| Ex. No. | Structure | I to $S_A$ | to $S_C$ | to $S_{M1}$ | to K | to $S_C$ | to $S_A$ |
|---|---|---|---|---|---|---|---|
| 208 | 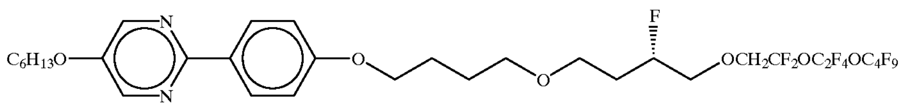 | 100.8 | 94.1 | −12.7 | | 19.2 | 96.5 |
| 209 | 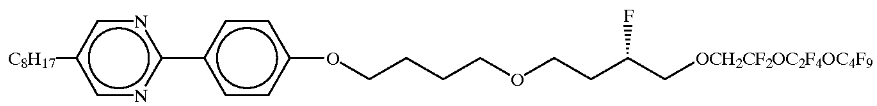 | 78.2 | 60.3 | −11.3 | | 32.5 | 62.5 |
| 210 | 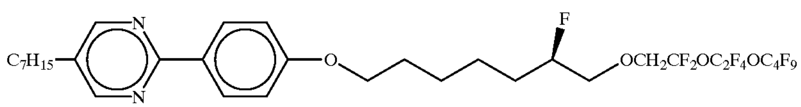 | 100.5 | 79.8 | −0.6 | | 11.7 | 82.3 |
| 211 | 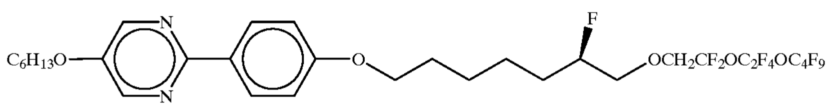 | 120.1 | 103.1 | −5.3 | | 17.9 | 105.9 |
| 212 | 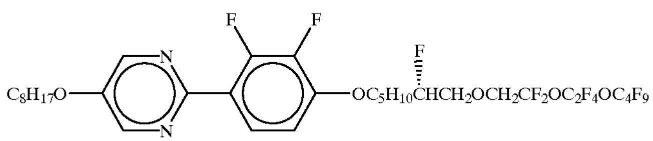 | 100.9 | 75.5 | 2.2 | | 24 | 78 |
| 213 | 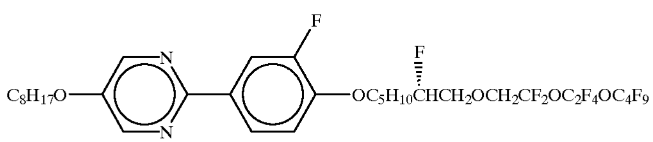 | 111.5 | 94.2 | −7.3 | | 14.4 | 96.7 |

TABLE 1-continued

| Ex. No. | Structure | I to $S_A$ | to $S_C$ | to $S_{M1}$ | to K | to $S_C$ | to $S_A$ |
|---|---|---|---|---|---|---|---|
| 214 | pyridine-phenyl core with C$_8$H$_{17}$, F chiral center, and OCH$_2$CF$_2$OC$_2$F$_4$OC$_4$F$_9$ tail | 96.4 | 85.4 | 59.2 | | 63.2 | 87.6 |
| 215 | C$_6$H$_{13}$O-phenyl-pyridine with CH$_3$ chiral center and OCH$_2$OC$_2$F$_4$OC$_2$F$_4$OC$_4$F$_9$ | 82 | 65 | 2 | | | |
| 216 | C$_7$H$_{15}$O-phenyl-pyridine with CF$_3$ chiral center and OCH$_2$CF$_2$OC$_2$F$_4$OC$_4$F$_9$ | 68 | 48 | −7 | | | |
| 217 | OC$_6$H$_{12}$-phenyl-pyridine with F chiral center and OCH$_2$CF$_2$O(C$_2$F$_4$)$_2$CF$_3$ | 93 | 81 | 24 | | | |
| 218 | C$_6$H$_{13}$O-phenyl-pyridine with F chiral center and OCH$_2$C$_3$F$_6$CH$_2$OCH$_2$CHCH$_2$OCH$_2$CF$_2$OC$_4$F$_9$ | 82.5 | 67.4 | 4 | | | |
| 219 | C$_7$H$_{15}$O-phenyl-pyridine with F chiral center and OCH$_2$C$_2$F$_4$CH$_2$OCH$_2$CHCH$_2$OCH$_2$CF$_2$OC$_4$F$_9$ | 73.8 | 57.7 | 1.7 | | | |

The data in Table 1 shows that most of the compounds of the invention exhibit smectic mesophases and that many of the compounds exhibit a broad smectic C mesophase, which makes the compounds well-suited for use in liquid crystal display devices. As a result of the breadth of the smectic C mesophase, the compounds are useful in admixture with themselves or with other liquid crystal compounds, even at high concentration.

The smectic C layer spacing of selected compounds of the invention was measured as a function of temperature by Small Angle X-ray Scattering (SAXS), essentially as described in U.S. Pat. No. 5,417,883, and a plot of the data is shown in FIG. 1. This data indicates that the compounds of the invention generally exhibited maintenance or expansion of the smectic C layer spacing with decreasing temperature (and can be used to control layer spacing with respect to temperature as described in U.S. Pat. No. 5,417,883). The expansion rate varied with structure.

Examples 220 Through 236

A series of devices, each containing a chiral compound of this invention (designated by a parenthetical reference to Example No. in Table 2 below), was prepared essentially as described in U.S. Pat. No. 5,377,033 (Radcliffe). The ITO-constituted electrodes of each device were connected to an arbitrary waveform generator with variable output voltage. The device was driven by a voltage waveform consisting of bipolar, square pulses of ±10 V/$\mu$m amplitude, spaced 30 milliseconds apart by a train of square pulses having the same width and 3.3 V/$\mu$m amplitude. The device was heated to the temperatures noted in Table 3 (below) and the polarization (nC/cm$^2$), the $\tau_{electric}$, the smectic viscosity, and the tilt angle $\phi_t$ were determined as described below:

The polarization of the device was determined essentially as described by Miyasato et al. in Jap. J. Appl. Phys. 22, 661 (1983). The electronic response time, $\tau_{electric}$, was derived from the displacement current of the ferroelectric liquid crystal device under an applied square voltage pulse. The current was viewed on a 100 megahertz bandwidth oscilloscope. The usual decaying exponential, associated with a dielectric filled capacitor, was followed by the spontaneous polarization ($P_s$) switching pulse. The time from the rising edge of the voltage pulse to the peak of the $P_s$ pulse was taken to be $\tau_{electric}$. The rotational viscosity (smectic viscosity, $\eta$) was calculated as shown below:

$$\eta(10^{-3} \text{ kg/m·s}) = 0.01 \cdot P_s \cdot E \cdot \tau_{electric},$$

where the units of $P_s$, E, and $\tau_{electric}$ are respectively nC/cm$^2$†, V/$\mu$m, and $\mu$s. The tilt angle $\phi_t$ of the mixture was taken to be half the angle separating the extinction points of the driven states. The results given in Table 2 show fast response times over a wide temperature range.

TABLE 2

| Example No. | Temperature (° C.) | Reduced Temperature (T-T$_c$, ° C.) | Polarization (nC/cm$^2$) | Response Time ($\mu$s) | Smectic Viscosity (mPa.s) | Tilt Angle (degrees) |
|---|---|---|---|---|---|---|
| 220 | 50.2 | −9.3 | 25.3 | 5.8 | 14.6 | 22.6 |
| (using | 39.6 | −19.9 | 31.6 | 7.0 | 22.0 | 24.1 |
| compound | 29.6 | −29.9 | 37.1 | 8.1 | 29.9 | 24.6 |
| Of Ex. | 19.5 | 40.0 | 42.2 | 9.9 | 41.7 | 24.7 |
| No. 144) | 14.2 | −45.3 | 45.0 | 11.2 | 50.4 | 24.7 |
| 221 | 40.5 | 9.9 | 27.1 | 5.0 | 13.6 | 20.8 |
| (using | 30.3 | −20.1 | 33.1 | 6.4 | 21.2 | 21.7 |
| compound | 20.1 | −30.3 | 38.8 | 7.5 | 29.1 | 22.1 |
| of Ex. | 9.9 | 40.5 | 45.2 | 9.4 | 42.5 | 0.0 |
| No. 40) | | | | | | |
| 222 | 53.0 | 3.0 | 2.1 | 8.0 | 1.7 | |
| (using | 42.7 | −7.3 | 3.7 | 37.9 | 14.0 | 16.1 |
| compound | 32.5 | −17.5 | 3.8 | 76.5 | 29.1 | 18.1 |
| of Ex. | 22.1 | −27.9 | 2.1 | 18.9 | | |
| No. 106) | | | | | | |
| 223 | 73.5 | −8.5 | 27.5 | 5.2 | 14.4 | 23.3 |
| (using | 62.9 | −19.1 | 34.6 | 6.1 | 21.0 | 24.9 |
| compound | 52.7 | −29.3 | 41.2 | 7.0 | 28.6 | 25.6 |
| of Ex. | 42.7 | −39.3 | 47.0 | 8.2 | 38.4 | 25.8 |
| No. 45) | 32.3 | 49.7 | 53.3 | 10.3 | 54.8 | 25.9 |
| | 22.3 | −59.7 | 59.3 | 13.4 | 79.6 | 25.7 |
| | 12.0 | −70.1 | 61.2 | 19.5 | 119.6 | 25.5 |
| 224 | 87.6 | −8.4 | 26.7 | 5.5 | 14.7 | 28.6 |
| (using | 77.5 | −18.5 | 32.7 | 6.3 | 20.5 | 30.2 |
| compound | 67.2 | −28.8 | 38.0 | 7.0 | 26.5 | 31.8 |
| of Ex. | 57.0 | −39.0 | 42.6 | 8.0 | 33.9 | 32.0 |
| No. 46) | 46.8 | 49.2 | 47.3 | 9.4 | 44.7 | 32.0 |
| | 36.5 | −59.5 | 52.4 | 11.5 | 60.5 | 31.7 |
| | 26.2 | −69.8 | 57.5 | 15.4 | 88.3 | 31.4 |
| | 16.0 | −80.1 | 63.7 | 21.9 | 139.5 | 31.1 |
| 225 | 70.7 | −1.3 | 6.4 | 6.2 | 4.0 | 15.3 |
| (using | 60.3 | −11.7 | 9.7 | 10.5 | 10.2 | 18.0 |
| compound | 50.2 | 41.8 | 11.7 | 13.1 | 15.2 | 18.8 |
| Of Ex. | 40.1 | −31.9 | 13.1 | 16.5 | 21.6 | 19.1 |
| No. 93) | 30.0 | 42.0 | 14.2 | 22.1 | 31.4 | 19.1 |

TABLE 2-continued

| Example No. | Temperature (° C.) | Reduced Temperature (T-$T_c$, ° C.) | Polarization (nC/cm²) | Response Time (µs) | Smectic Viscosity (mPa.s) | Tilt Angle (degrees) |
|---|---|---|---|---|---|---|
| 226 | 91.6 | −12.4 | 23.7 | 6.4 | 15.3 | 28.7 |
| (using | 78.0 | −26.0 | 31.2 | 8.1 | 25.4 | 31.4 |
| compound | 64.1 | −39.9 | 38.5 | 10.6 | 40.9 | 32.6 |
| of Ex. | 50.1 | −53.9 | 47.0 | 14.8 | 69.8 | 33.2 |
| No. 73) | 36.1 | −67.9 | 58.1 | 22.6 | 131.4 | 33.6 |
|  | 22.2 | −81.8 | 72.6 | 39.9 | 289.4 | 33.9 |
| 227 | 85.6 | −9.9 | 17.0 | 6.6 | 11.2 | 26.4 |
| (using | 75.8 | −19.7 | 20.5 | 7.5 | 15.4 | 27.9 |
| compound | 65.6 | −29.9 | 23.1 | 8.5 | 19.5 | 28.4 |
| of Ex. | 55.8 | −39.7 | 25.2 | 9.7 | 24.5 | 28.4 |
| No. 133) | 45.6 | −49.9 | 27.9 | 11.4 | 31.9 | 28.3 |
|  | 35.6 | −59.9 | 30.8 | 14.0 | 43.0 | 28.0 |
|  | 25.5 | −70.0 | 34.8 | 18.3 | 63.7 |  |
| 228 | 69.1 | −9.9 | 19.0 | 7.4 | 14.1 | 22.2 |
| (using | 58.9 | −20.1 | 22.0 | 9.7 | 21.3 | 23.2 |
| compoun4 | 49.0 | −30.0 | 23.9 | 12.7 | 30.4 | 23.3 |
| Of Ex. | 38.8 | 40.2 | 25.6 | 17.3 | 44.3 | 22.9 |
| No. 204) | 29.1 | 49.9 | 27.0 | 24.8 | 67.0 | 22.2 |
|  | 19.0 | −60.0 | 28.5 | 42.0 | 119.7 | 21.4 |
|  | 9.1 | −69.9 | 30.1 | 77.2 | 232.4 | 20.6 |
| 229 | 55.3 | −10.2 | 21.4 | 7.9 | 16.8 | 23.5 |
| (using | 45.4 | −20.1 | 24.2 | 9.3 | 22.5 | 24.6 |
| compound | 35.5 | −30.0 | 27.5 | 11.7 | 32.1 | 24.8 |
| of Ex. | 25.2 | 40.3 | 30.0 | 15.8 | 47.4 | 24.7 |
| No. 173) | 15.2 | −50.3 | 31.6 | 23.3 | 73.8 | 24.4 |
|  | 5.4 | −60.1 | 33.8 | 39.7 | 134.5 | 23.9 |
| 230 | 62.1 | −10.1 | 21.7 | 8.8 | 19.0 | 27.4 |
| (using | 52.1 | −20.1 | 27.9 | 10.2 | 28.3 | 29.1 |
| compound | 42.0 | −30.2 | 34.6 | 12.1 | 41.8 | 29.8 |
| Of Ex. | 32.1 | −40.1 | 41.4 | 15.3 | 63.5 | 30.0 |
| No. 206) | 22.1 | −50.1 | 49.2 | 20.5 | 100.9 | 30.1 |
|  | 12.1 | −60.1 | 56.2 | 30.2 | 169.8 | 30.0 |
|  | 2.1 | −70.1 | 65.4 | 51.8 | 338.6 | 29.8 |
| 231 | 72.1 | 4.6 | 4.4 | 8.7 | 3.9 | 15.2 |
| (using | 67.2 | −9.5 | 5.2 | 10.3 | 5.3 | 16.2 |
| compound | 56.8 | −19.9 | 6.9 | 11.1 | 7.7 | 16.3 |
| of Ex. | 46.8 | −29.9 | 8.1 | 12.1 | 9.8 | 16.1 |
| No. 101) | 36.7 | 40.0 | 9.0 | 13.8 | 12.4 | 15.8 |
|  | 26.7 | −50.0 | 10.5 | 16.4 | 17.2 | 15.6 |
|  | 16.6 | −60.1 | 11.4 | 21.5 | 24.6 | 15.2 |
| 232 | 39.4 | −9.9 | 74.3 | 11.5 | 85.6 | 35.3 |
| (using | 29.1 | −20.2 | 89.8 | 16.4 | 147.2 | 37.1 |
| compound | 19.1 | 30.2 | 98.3 | 25.6 | 251.5 | 37.9 |
| of Ex. | 9.1 | −40.2 | 101.3 | 46.2 | 467.7 | 38.3 |
| No. 216) | −1.0 | −50.3 | 104.9 | 106.2 | 1114.0 | 38.4 |
| 233 | 39.3 | −6.5 | 38.1 | 5.0 | 19.2 |  |
| (using | 32.2 | −13.6 | 47.5 | 6.9 | 33.0 |  |
| compound | 24.2 | −21.6 | 58.2 | 8.7 | 50.6 |  |
| of Ex. | 17.0 | −28.8 | 69.3 | 10.6 | 73.7 |  |
| No. 59) | 9.6 | −36.2 | 82.2 | 14.0 | 115.1 |  |
| 234 | 77.0 | −11.5 | 38.2 | 4.6 | 17.8 |  |
| (using | 66.8 | −21.7 | 46.3 | 5.2 | 24.0 | 27.9 |
| compound | 56.8 | −31.7 | 55.6 | 6.0 | 33.3 | 28.6 |
| of Ex. | 46.9 | A1.6 | 61.1 | 7.0 | 42.7 | 28.8 |
| No. 63) | 36.9 | −S1.6 | 68.1 | 8.7 | 59.4 | 28.8 |
|  | 26.8 | −61.7 | 74.4 | 11.5 | 85.2 |  |
|  | 16.7 | −71.8 | 80.1 | 16.4 | 131.2 |  |
| 235 | 43.1 | −7.1 | 42.7 | 4.2 | 17.9 |  |
| (using | 38.4 | −11.8 | 49.0 | 5.1 | 25.1 |  |
| compound | 33.7 | −16.5 | 55.5 | 6.0 | 33.6 |  |
| of Ex. | 28.7 | −21.5 | 62.8 | 7.1 | 44.4 |  |
| No. 53) | 23.7 | −26.5 | 70.0 | 8.3 | 57.8 |  |
|  | 18.8 | −31.4 | 78.1 | 9.7 | 76.0 |  |
|  | 13.6 | −36.6 | 88.4 | 11.5 | 101.8 |  |
| 236 | 68.0 | −10.0 | 13.0 | 7.4 | 9.6 | 23.4 |
| (using | 58.0 | −20.0 | 16.2 | 8.4 | 13.6 | 24.7 |
| compound | 48.0 | −30.0 | 17.6 | 10.0 | 17.6 | 25.0 |
| of Ex. | 38.0 | 40.0 | 19.1 | 12.6 | 24.1 | 24.9 |
| No. 182) | 28.0 | −50.0 | 20.4 | 16.7 | 34.1 | 24.6 |
|  | 18.0 | −60.0 | 21.9 | 24.0 | 52.6 | 24.1 |
|  | 8.0 | −70.0 | 23.4 | 39.9 | 93.4 | 23.6 |

Example 237

A device was prepared essentially as described above using a mixture of 90 weight % of the compound of the invention prepared in Example 93 and 10 weight % 5-octyloxy-2-[4-(3-(4-(nonafluorobutoxy)octafluorobutoxy)-2,2,3,3,4,4-hexafluorobutoxy)2-(S)-fluoropropoxyphenyl]pyrimidine (prepared essentially as described in Example 12 of International Patent Publication No. WO 96/33251), and the electrooptical properties of the mixture were measured essentially as previously described. The results are shown in Table 4.

Example 238–242

In the following Examples, a series of devices, each containing at least one chiral compound of this invention, were prepared essentially as described in U.S. Pat. No. 5,377,033 (Radcliffe) and filled with a mixture of liquid crystal compounds. The composition of each mixture (in weight percent) and the phase transition temperatures of the mixtures are shown in Table 3.

Compound A, 5-hexyl-2-[4-(6-(2-(2-(2-(trifluoromethoxy)tetrafluoroethoxy)tetrafluoroethoxy)-2,2-difluoroethoxy)hexyl)phenyl]pyrimidine, was prepared essentially as in Example 1 by combining 6-(2-(2-(2-(trifluoromethoxy)tetrafluoroethoxy)tetrafluoroethoxy)-2,2-difluoroethoxy)hex-1-ene (6.0 g, 12.4 mmol) and 5-hexyl-2-(4-(trifluoromethylsulfonyl)phenyl)pyrimidine (4.70 g, 12.4 mmol). The resulting mixture was quenched with water, and the resulting crude product was isolated by extraction with toluene and further purified essentially as in Example 1, followed by Kugelrohr distillation (187–92° C. at 0.01 to 0.015 torr) to provide a yield of 4.45 g.

Compound B, 5-heptyloxy-2-[4-(6-(2-(2-(2-(trifluoromethoxy)tetrafluoroethoxy)tetrafluoroethoxy)-2,2-difluoroethoxy)hexyl)phenyl]pyrimidine was prepared using essentially the procedure of Example 1 by combining 6-(2-(2-(2-(trifluoromethoxy)tetrafluoroethoxy)tetrafluoroethoxy)-2,2-difluoroethoxy)hex-1-ene and 5-heptyloxy-2-(4-(trifluoromethylsulfonyl)phenyl)pyrimidine.

Compound C, 5-heptyloxy-2-[4-(6-(3-(pentafluoroethoxy)-2,2,3,3-tetrafluoropropoxy)hexyl)phenyl]pyrimidine was prepared using essentially the procedure of Example 1 by combining 3-(pentafluoroethoxy)-2,2,3,3-tetrafluoropropoxy)hex-1-ene and 5-heptyloxy-2-(4-(trifluoromethylsulfonyl)phenyl)pyrimidine.

TABLE 3

| | Example No. | | | | | |
|---|---|---|---|---|---|---|
| Compound | 237 | 238 | 239 | 240 | 241 | 242 |
| Example 93 | 90 | | | | | |
| Example 12 of WO 96/33251 | 10 | | | | | |
| Example 155 | | 15 | 15 | 10 | | |
| Example 63 | | 30 | 30 | 20 | | |
| Example 211 | | 25 | | | | |
| Example 30 of US 5658491 | | 10 | 10 | 10 | | |
| Compound A | | 20 | 20 | 20 | | |
| Example 204 | | | 25 | | | |
| Example 34 | | | | 40 | | |
| Example 200 | | | | | 54 | |
| Example 13 | | | | | 46 | |
| Example 112 | | | | | | 15 |
| Example 44 | | | | | | 20 |
| Example 35 | | | | | | 20 |
| Example 151 | | | | | | 10 |
| Compound B | | | | | | 15 |
| Compound C | | | | | | 20 |
| Transition Temperature Data (° C.) | | | | | | |
| I to S$_A$ | 112.3 | 106.1 | 102.6 | 101.2 | 96.0 | 198.0 |
| to S$_C$ | 155.4 | 74.0 | 68.2 | 64 | 79.2 | 55.4 |
| to S$_{M1}$ | <6 | <1 | <1 | <−1 | 10 | <−5 |

TABLE 4

| Example No. | Temperature (° C.) | Reduced Temperature (T-T$_c$, ° C.) | Polarization (nC/cm$^2$) | Response Time ($\mu$s) | Smectic Viscosity (mPa.s) | Tilt Angle (degrees) |
|---|---|---|---|---|---|---|
| 237 | 46.6 | −8.8 | 13.4 | 6.1 | 8.2 | 14.8 |
| | 36.7 | −18.7 | 15.7 | 8.3 | 13.0 | 15.5 |
| | 26.8 | −28.6 | 17.4 | 10.9 | 19.0 | 15.4 |
| | 16.5 | −38.9 | 18.5 | 15.6 | 28.8 | 15.1 |
| | 6.4 | −49.0 | 19.8 | 24.4 | 48.4 | 14.8 |
| 238 | 62 | −10 | 22.5 | 6.1 | 13.7 | 23.3 |
| | 52 | −20 | 27.7 | 7.3 | 20.2 | 24.9 |
| | 42 | −30 | 31.9 | 9.0 | 28.7 | 25.6 |
| | 32 | 40 | 36.2 | 11.4 | 41.1 | 25.9 |
| | 22 | −50 | 40.7 | 15.9 | 64.5 | 26.0 |
| 239 | 58 | −10 | 20.7 | 6.3 | 13.1 | 22.4 |
| | 48 | 40 | 25.4 | 7.7 | 19.6 | 24.0 |
| | 38 | −30 | 29.1 | 9.5 | 27.5 | 24.6 |
| | 28 | 40 | 32.6 | 12.1 | 39.4 | 24.8 |
| | 18 | −50 | 35.7 | 17.7 | 63.1 | 24.8 |
| 240 | 52 | −10 | 24.3 | 6.3 | 15.4 | |
| | 42 | −20 | 28.8 | 7.4 | 21.5 | |
| | 32 | −30 | 33.4 | 9.4 | 31.4 | |
| | 22 | −40 | 37.1 | 12.8 | 47.5 | |
| | 12 | −50 | 41.8 | 18.7 | 78.2 | |

TABLE 4-continued

| Example No. | Temperature (° C.) | Reduced Temperature (T-$T_c$, ° C.) | Polarization (nC/cm$^2$) | Response Time (µs) | Smectic Viscosity (mPa.s) | Tilt Angle (degrees) |
|---|---|---|---|---|---|---|
| 241 | 69 | −10 | 33.7 | 6.9 | 23.1 | 29.0 |
| | 59 | −20 | 41.7 | 8.0 | 33.3 | 30.9 |
| | 49 | −30 | 48.5 | 9.6 | 46.6 | 31.8 |
| | 39 | −40 | 57.0 | 12.0 | 68.3 | 32.3 |
| | 29 | −50 | 64.9 | 15.7 | 102.2 | 32.5 |
| | 19 | −60 | 76.3 | 22.2 | 169.2 | 32.7 |
| 242 | 49 | −7 | 16.4 | 5.6 | 9.2 | 17.7 |
| | 38 | −17 | 21.6 | 8.5 | 18.3 | 19.6 |
| | 28 | −27 | 26.3 | 11.1 | 29.3 | 20.6 |
| | 23 | −32 | 28.4 | 12.9 | 36.6 | 20.9 |
| | 18 | −37 | 31.1 | 15.3 | 47.8 | 21.1 |
| | 8 | −47 | 36.8 | 23.4 | 86.0 | 21.5 |

The results shown in table 4 indicate that the compounds of the invention can be used in mixtures in liquid crystal display devices to provide low mixture viscosities and improve the performance of the devices.

Various modifications and alterations of this invention will become apparent to those skilled in the art without departing from the scope and spirit of this invention.

What is claimed is:

1. Fluorine-containing, chiral liquid crystal compounds having smectic mesophases or latent smectic mesophases, the compounds comprising (a) a chiral fluorochemical terminal portion comprising (i) at least one chiral center, which can optionally be heteroatom-substituted; (ii) a terminal fluoroalkyl, fluoroether, perfluoroalkyl, or perfluoroether group, wherein the fluoroalkyl and perfluoroalkyl groups are represented by the formula —$C_qF_{2q}X'$, wherein q is at least about 5 and X' is hydrogen or fluorine; and (iii) an alkylene or fluoroalkylene group optionally containing at least one catenary ether oxygen atom; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core.

2. The compounds of claim 1 wherein said chiral fluorochemical terminal portion is represented by the formula —D—R*—D—$R_f$, where R* is a cyclic or acyclic chiral moiety containing at least one chiral center; $R_f$ is fluoroalkyl, perfluoroalkyl, fluoroether, or perfluoroether; and each D is independently and non-directionally selected from the group consisting of a covalent bond, —C(=O)—O—$C_rH_{2r}$—, —O—$C_rH_{2r}$—, —O—(O=)C—$C_rH_{2r}$—, —C≡C—, —CH=CH—, —C(=O)—, —O-($C_sH_{2s}$O)$_t$-$C_rH_{2r}$—, —$C_rH_{2r}$—($C_sH_{2s}$O)$_t$-$C_rH_{2r}$—, —O—, —S—, —OSO$_2$—, —SO$_2$—, —SO$_2$—$C_rH_{2r}$—, —$C_rH_{2r}$—N—SO$_2$—, —N($C_pH_{2p+1}$)—
         |
         $C_pH_{2p+1}$

[—$C_rH_{2r}$—N—C(=O)—, —CH=N—,]

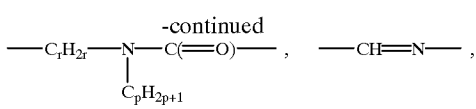

-continued

—$C_rH_{2r}$—N—C(=O)—, —CH=N—,
         |
         $C_pH_{2p+1}$ and combinations thereof, where one or more hydrogen atoms can optionally be replaced with fluorine, and where r and r' are independently integers of 0 to about 20, s is independently an integer of 1 to about 10 for each ($C_sH_{2s}$O), t is an integer of 1 to about 6, and p is an integer of 0 to about 4; with the proviso that there are at least 3 in-chain atoms between said central core and at least one said chiral center of R*.

3. The compounds of claim 2 wherein said $R_f$ is perfluoroalkyl or perfluoroether.

4. The compounds of claim 3 wherein said $R_f$ is perfluoroether.

5. The compounds of claim 1 wherein said compounds are represented by the general formula (I):

$$R\text{—}(M)_a\text{—}A\text{—}(N)_b\text{—}B\text{—}(P)_c\text{—}D\text{—}R^*\text{—}D\text{—}R_f \quad (I)$$
$$\quad\quad |\quad\quad\quad |\quad\quad\quad |$$
$$\quad\quad X_1\quad\quad Y_m\quad\quad Z_n$$

where M, N, and P are each independently selected from the group consisting of

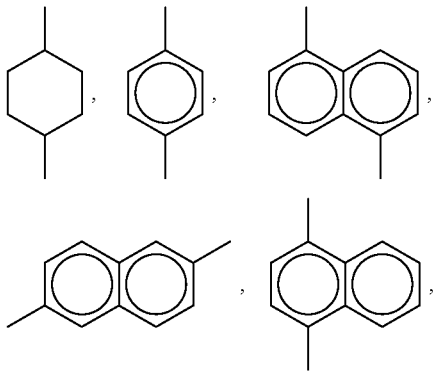

-continued

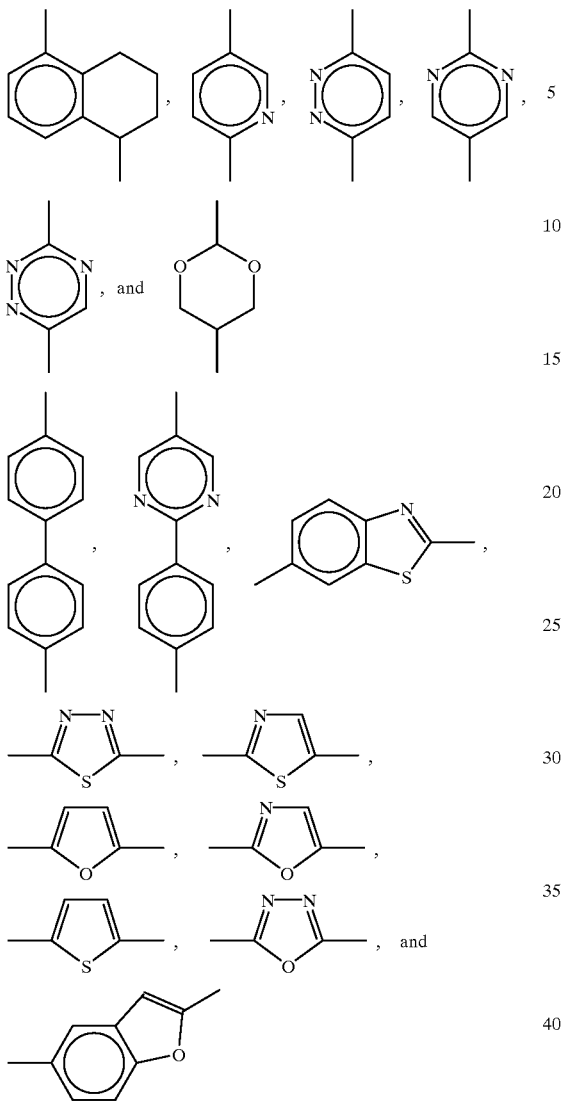

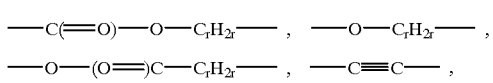

a, b, and c are each independently zero or an integer of from 1 to 3, with the proviso that the sum of a+b+c be at least 1;

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are each independently zero or an integer of 1 to 4;

each D is non-directionally and independently selected from the group consisting of a covalent bond,

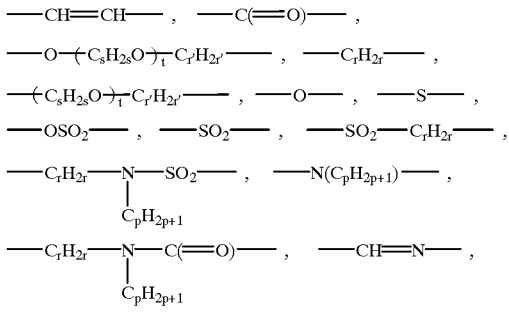

-continued

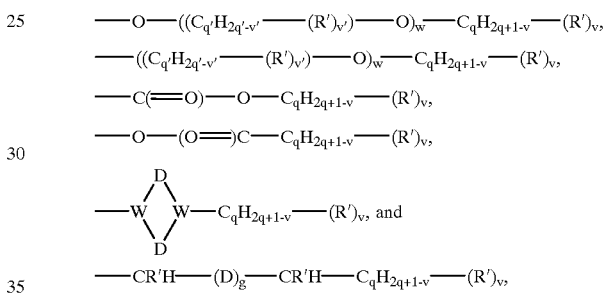

and combinations thereof, where one or more hydrogen atoms can optionally be replaced with fluorine, and where r and r' are independently integers of 0 to about 20, s is independently an integer of 1 to about 10 for each (C$_s$H$_{2s}$O), t is an integer of 1 to about 6, and p is an integer of 0 to about 4;

R is selected from the group consisting of

—O—((C$_{q'}$H$_{2q'-v'}$——(R')$_{v'}$)——O)$_w$—C$_q$H$_{2q+1-v}$——(R')$_v$,

—((C$_{q'}$H$_{2q'-v'}$——(R')$_{v'}$)——O)$_w$—C$_q$H$_{2q+1-v}$——(R')$_v$,

—C(=O)—O—C$_q$H$_{2q+1-v}$——(R')$_v$,

—O—(O=)C—C$_q$H$_{2q+1-v}$——(R')$_v$,

—W(D)(D)W—C$_q$H$_{2q+1-v}$——(R')$_v$, and

—CR'H——(D)$_g$——CR'H——C$_q$H$_{2q+1-v}$——(R')$_v$, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$; q' is independently an integer of 1 to about 20 for each (C$_{q'}$H$_{2q'}$—O); q is an integer of 1 to about 20; w is an integer of 0 to about 10; v is an integer of 0 to about 2; each v' is independently an integer of 0 to about 2; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and R can be chiral or achiral; and R* is a cyclic or acyclic chiral moiety containing at least one chiral center; and R$_f$ is fluoroalkyl, perfluoroalkyl, fluoroether, or perfluoroether group, wherein the fluoroalkyl and perfluoroalkyl groups are represented by the formula —C$_q$F$_{2q}$X', wherein q is at least about 5 and X' is hydrogen or fluorine;

with the proviso that there are at least 3 in-chain atoms between said central core structure —(M)$_a$—A—(N)$_b$—B—(P)$_c$— and at least one said chiral center of R*.

6. The compounds of claim 5 wherein said R* is selected from the group consisting of

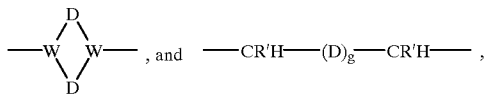, and —CR'H—(D)$_g$—CR'H—, where each R' is independently selected from the group consisting of —Cl, —F, —CF$_3$, —NO$_2$, —CN, —H, —C$_q$H$_{2q+1}$, —O—(O=)C—C$_q$H$_{2q+1}$, —C(=O)—O—C$_q$H$_{2q+1}$, —Br, —OH, and —OC$_q$H$_{2q+1}$; q' is independently an integer of 1 to about 20 for each (C$_q$H$_{2q'}$—O); q is an integer of 1 to about 20; w is an integer of 0 to about 10; v is an integer of 0 to about 3; each v' is independently an integer of 0 to about 3; g is an integer of 1 to about 3; each D is independently and non-directionally selected from the group set forth for D in claim 5, with the proviso that the ring containing D has from about 3 to about 10 ring atoms; each W is independently selected from the group consisting of N, CR', and SiR'; and with the proviso that R* is chiral.

7. The compounds of claim 6 wherein each said R' of said R* is independently selected from the group consisting of —H, —F, —CF$_3$, —Br, —OH, and —OCH$_3$.

8. The compounds of claim 5 wherein said R$_f$ is a perfluoroalkyl group represented by the formula —C$_q$F$_{2q}$X' wherein q is at least about 5 and X' is hydrogen or fluorine or a perfluoroether group.

9. The compounds of claim 8 wherein said R$_f$ is perfluoroether.

10. The compounds of claim 5 wherein said perfluoroalkyl is represented by the formula —C$_q$F$_{2q}$X' where q is at least about 5 and X' is hydrogen or fluorine; and said perfluoroether is represented by the formula —(C$_x$F$_{2x}$O)$_z$C$_y$F$_{2y+1}$, where x is independently an integer of 1 to about 10 for each (C$_x$F$_{2x}$O), y is an integer of 1 to about 10, and z is an integer of 1 to about 10.

11. The compounds of claim 5 wherein said compounds are represented by the general formula (II):

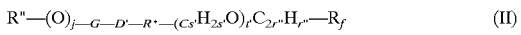 (II)

where R" is (R')$_v$—C$_q$H$_{2q+1-v}$, where q is an integer of 2 to about 10, each R' is independently selected from the group consisting of hydrogen, fluorine, chlorine, methyl, and perfluoromethyl, and v is an integer of 1 to about 2;

j is an integer of 0 or 1;

G is selected from the group consisting of

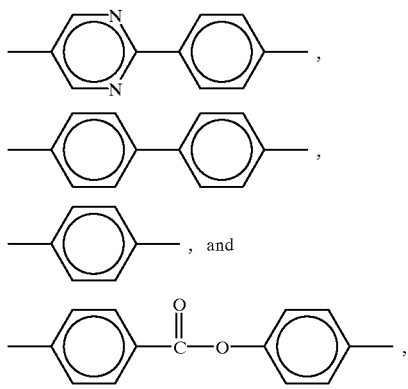

where one or more aromatic hydrogen atoms can be replaced with fluorine;

D' is selected from the group consisting of —O— (C$_s$H$_{2s}$O)$_t$ C$_r$H$_{2r'}$—, —C$_r$H$_{2r}$—, —(C$_s$H$_{2s}$O)$_t$C$_r$H$_{2r'}$—, and —O—C$_r$H$_{2r}$—, where r and r' are independently integers of 0 to about 12, s is independently an integer of 1 to about 10 for each (C$_s$H$_{2s}$O), and t is an integer of 1 to about 3;

R* is selected from the group consisting of —C$_q$H$_{2q-v}$— $_{(R')_v}$— and

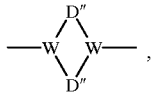, where R' is —F, q is an integer of 1 to about 4, v is an integer of 1 to about 3, W is N or CH, and D" is —C(=O)—O— or —CH$_2$—;

s' is an integer of 1 to about 6;

t' is an integer of 0 or 1;

r" is an integer of 1 to about 3; and

R$_f$ is selected from the group consisting of —C$_q$F$_{2q+1}$ and —(C$_x$F$_{2x}$O)$_z$C$_y$F$_{2y+1}$, where q is an integer of 5 to about 6, x is independently an integer of 1 to about 10 for each (C$_x$F$_{2x}$O), y is an integer of 1 to about 8, and z is an integer of 1 to about 5;

with the proviso that there are at least 3 in-chain atoms between said central core structure G and at least one said chiral center of R*.

12. The compounds of claim 11 wherein said s', said t', and said r" are each an integer of 1.

13. Fluorine-containing, chiral liquid crystal compounds having smectic mesophases or latent smectic mesophases, the compounds comprising (a) a chiral fluorochemical terminal portion represented by the formula —D—R*—D—R$_f$ where R* is a cyclic or acyclic chiral, moiety containing at least one chiral center; R$_f$ is perfluoroether; and each D is independently and non-directionally selected from the aroup consisting of a covalent bond,

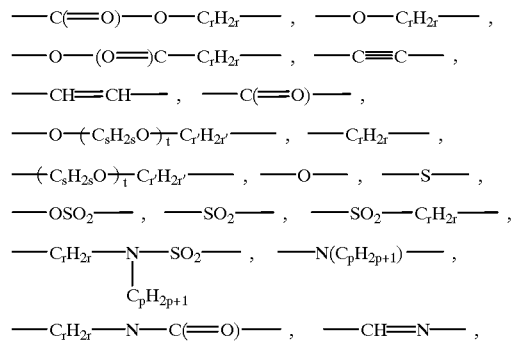

and combinations thereof where one or more hydrogene atoms can optionally be replaced with fluorine and where r and r' are independently integers of 0 to about 20, s is independently an integer of 1 to about 10 for each (C$_s$H$_{2s}$O, t is an integer of 1 to about 6, and p is an integer of 0 to about 4 with the proviso that there are at least 3 in-chain atoms between central core and at least one said chiral center of R*, (b) a chiral or achiral terminal portion consisting of a hydrocarbon or hydrocarbon ether group, and, when chiral, comprising at least one chiral center, which can optionally be heteroatom-substituted; and (c) a central core connecting said terminal portions.

14. mixture of liquid crystal compounds comprising at least one fluorine-containing liquid crystal compound of claim 1.

15. The mixture of claim 14 further comprising at least one other liquid crystal compound having at least one fluorinated terminal portion.

16. The mixture of claim wherein said other liquid crystal compound is a chiral or achiral, perfluoroether group-containing liquid crystal compound.

17. A liquid crystal device containing at least one fluorine-containing liquid crystal compound of claim 1.

18. The device of claim 17 further containing at least one other liquid crystal compound having at least one fluorinated terminal portion.

19. The device of claim 18 wherein said other liquid crystal compound is a chiral or achiral, perfluoroether group-containing liquid crystal compound.

20. Fluorine-containing, chiral liquid crystal compounds having smectic mesophases or latent smectic mesophases, the compounds comprising two fluorochemical terminal portions and being represented by the general formula VIII:

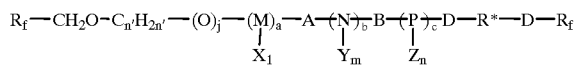

(VIII)

where n' is an integer of 0 to about 10; j is an integer of 0 or 1; each $R_f$ moiety is independently selected from the group consisting of fluoroalkyl, fluoroether, perfluoroalkyl, and perfluoroether; and all other moieties are as defined in claim 5 above.

21. The compounds of claim 20 wherein said compounds are represented by the general formula IX:

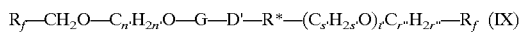

where n' is an integer of about 2 to about 6;

G is selected from the group consisting of

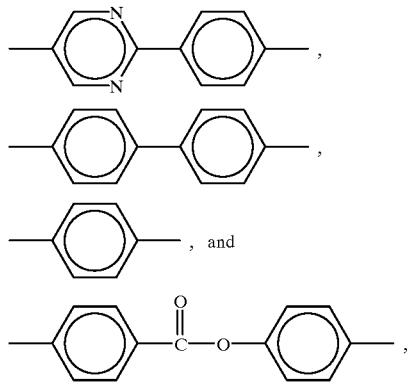

where one of more aromatic hydrogen atoms can be replaced with fluorine;

D' is selected from the group consisting of —O— $(C_sH_{2s}O)_t$ $C_{r'}H_{2r'}$—, —$C_rH_{2r}$—, —$(C_sH_{2s}O)_t$ $C_{r'}H_{2r'}$—, and —O—$C_rH_{2r}$— where r and r' are independently integers of 0 to about 12, s is independently an integer of 1 to about 10 for each $(C_sH_{2s}O)$, and t is an integer of 1 to about 3;

R* is selected from the group consisting of —$C_qH_{2q-v}$—(R')$_v$— and

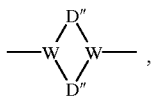

where R' is —F, 8 is an integer of 1 to about 4, v is an integer of 1 to about 3, W is N or CH, and D" is —C(=O)—O— or —$CH_2$—;

s' is an integer of 1 to about 6;

t' is an integer of 0 or 1;

r" is an integer of 1 to about 3; and each $R_f$ is independently selected from the group consisting of —$C_qF_{2q+1}$ and —$(C_xF_{2x}O)_zC_yF_{2y+1}$, where q is an integer of 1 to about 6, x is independently an integer of 1 to about 10 for each $(C_xF_{2x}O)$, y is an integer of 1 to about 8, and z is an integer of 1 to about 5;

with the proviso that there are at least 3 in-chain atoms between said central core structure G and at least one said chiral center of R*.

22. The compounds of claim 21 wherein said s', said t', and said r" are each an integer of 1.

23. Fluorine-containing, chiral liquid crystal compounds having smectic mesophases or latent smectic mesophases, the compounds comprising (a) a chiral fluorochemical terminal portion; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core;

wherein said chiral fluorochemical terminal portion is represented by the formula —D—R*—D—$R_f$, where R* is a cyclic or acyclic chiral moiety containing at least one chiral center; $R_f$ is perfluoroalkyl or perfluoroether; and each D is independently and non-directionally selected from the group consisting of a covalent bond, —C(=O)—O—$C_rH_{2r}$—, —O—$C_rH_{2r}$—, —O—(O=)C—$C_rH_{2r}$—, —C≡C—, —CH=CH—, —C(=O)—, —O—$(C_sH_{2s}O)_t$ $C_rH_{2r}$—, —$C_rH_{2r}$—, —$(C_sH_{2s}O)_t$$C_rH_{2r}$—, —O—, —S—, —$OSO_2$—, —$SO_2$—, —$SO_2$—$C_rH_{2r}$—, —$C_rH_{2r}$—N—$SO_2$—, —N($C_pH_{2p+1}$)—
　　　　　　|
　　　　$C_pH_{2p+1}$

[—$C_rH_{2r}$—N—C(=O)—, —CH=N—,]

—$C_rH_{2r}$—N—C(=O)—, —CH=N—,
　　　　　|
　　　$C_pH_{2p+1}$ and combinations thereof, where one or more hydrogen atoms can optionally be replaced with fluorine, and where r and r' are independently integers of 0 to about 20, s is independently an integer of 1 to about 10 for each $(C_sH_{2s}O)$, t is an integer of 1 to about 6, and p is an integer of 0 to about 4; with the proviso that there are at least 3 in-chain atoms between said central core and at least one said chiral center of R*.

24. Fluorine-containing, chiral liquid crystal compounds having smectic mesophases or latent smectic mesophases, the compounds comprising (a) a chiral fluorochemical terminal portion; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core;

wherein said compounds are represented by the general formula (I):

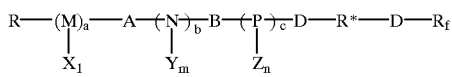

where M, N and P are each independently selected from the group consisting of

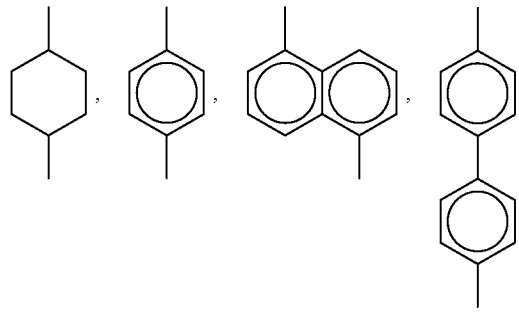

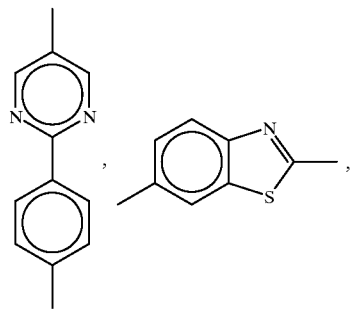

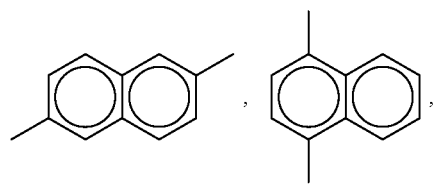

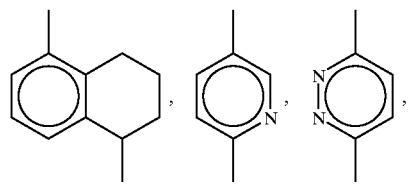

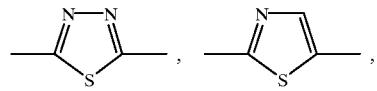

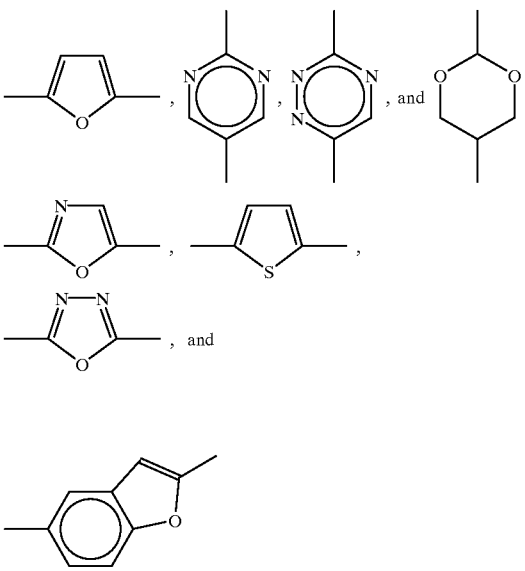

a, b, and c are each independently zero or an integer of from 1 to 3, with the proviso that the sum of a+b+c be at least 1;

each A and B are non-directionally and independently selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each X, Y, and Z are independently selected from the group consisting of —H, —Cl, —F, —Br, —I, —OH, —OCH$_3$, —CH$_3$, —CF$_3$, —OCF$_3$, —CN, and —NO$_2$;

each l, m, and n are independently zero or an integer of 1 to 4;

each D is non-directionally and independently selected from the group consisting of a covalent bond, —C(=O)—O—C$_r$H$_{2r}$—, —O—C$_r$H$_{2r}$—, —O—(O=)C—C$_r$H$_{2r}$—, —C≡C—, —CH=CH—, —C(=O)—, —O—(C$_s$H$_{2s}$O—)$_t$C$_r$H$_{2r}$—, —C$_r$H$_{2r}$—, —(C$_s$H$_{2s}$O—)$_t$C$_r$H$_{2r}$—, —O—, —S—, —OSO$_2$—, —SO$_2$—, —SO$_2$—C$_r$H$_{2r}$—, —C$_r$H$_{2r}$—N(C$_p$H$_{2p+1}$)—SO$_2$—, —N(C$_p$H$_{2p+1}$)—

—C$_r$H$_{2r}$—N(C$_p$H$_{2p+1}$)—C(=O)—, —CH=N—, and combinations thereof, where one or more hydrogen atoms can optionally be replaced with fluorine, and where r and r' are independently integers of 0 to about 20, s is independently an integer of 1 to about 10 for each (C$_s$H$_{2s}$O), t is an integer of 1 to about 6, and p is an integer of 0 to about 4;

R is selected from the group consisting of —O—((C$_{q'}$H$_{2q'-v'}$—(R')$_{v'}$)—O)$_w$—C$_q$H$_{2q+1-v}$—(R')$_v$, —((C$_{q'}$H$_{2q'-v'}$—(R')$_{v'}$)—O)$_w$—C$_q$H$_{2q+1-v}$—(R')$_v$, —C(=O)—O—C$_q$H$_{2q+1-v}$—(R')$_v$, —O—(O=)C—C$_q$H$_{2q+1-v}$—(R')$_v$,

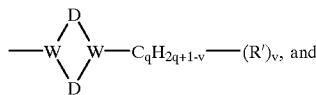

where each R' is independently selected from the group consisting of —Cl, —F, —CF$_3$, —NO$_2$, —CN, —H, —C$_q$H$_{2q+1}$,
—O—(O=)C—C$_q$H$_{2q+1}$, —C(=O)—O—C$_q$H$_{2q+1}$, —Br, —OH, and —OC$_q$H$_{2q+1}$; q' is independently an integer of 1 to about 20 for each (C$_{q'}$H$_{2q'}$—O); q is an integer of 1 to about 20; w is an integer of 0 to about 10; v is an integer of 0 to about 2; each v' is independently an integer of 0 to about 2; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and R can be chiral or achiral; and R* is a cyclic or acyclic chiral moiety containing at least one chiral center; and R$_f$ is perfluoroether; with the proviso that there are at least 3 in-chain atoms between said central core structure —(M)$_a$—A—(N)$_b$B—(P)$_c$— and at least one said chiral center of R*.

25. Fluorine-containing, chiral liquid crystal compounds having smectic mesophases or latent smectic mesophases, the compounds comprising (a) a chiral fluorochemical terminal portion; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core;

wherein said compounds are represented by the general formula (II):

R"—(O)$_j$—G—D'—R*—(C$_s$H$_{2s}$O)$_t$C$_r$H$_{2r'}$—R$_f$    (II)

where R" is (R')$_v$—C$_q$H$_{2q+1-v}$, where q is an integer of 2 to about 10, each R' is independently selected from the group consisting of hydrogen, fluorine, chlorine, methyl, and perfluoromethyl, and v is an integer of 1 to about 2;

j is an integer of 0 or 1;

G is selected from the group consisting of

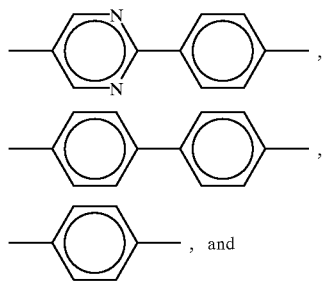

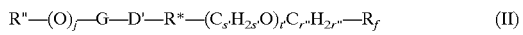

where one or more aromatic hydrogen atoms can be replaced with fluorine;

D' is selected from the group consisting of —O—(C$_s$H$_{2s}$O)$_t$ C$_{r'}$H$_{2r'}$—, —C$_r$H$_{2r}$—, —(C$_s$H$_{2s}$O)$_t$ C$_{r'}$H$_{2r'}$—, and —O—C$_r$H$_{2r}$—, where r and r' are independently integers of 0 to about 12, s is independently an integer of 1 to about 10 for each (C$_s$H$_{2s}$O), and t is an integer of 1 to about 3;

R* is selected from the group consisting of —C$_q$H$_{2q-v}$—(R')$_v$— and

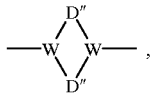

where R' is —F, q is an integer of 1 to about 4, v is an integer of 1 to about 3, W is N or CH, and D" is —C(=O)—O— or —CH$_2$—;

s' is an integer of 1 to about 6;

t' is an integer of 0 or 1;

r" is an integer of 1 to about 3; and

R$_f$ is selected from the group consisting of —C$_q$F$_{2q+1}$ and —(C$_x$F$_{2x}$O)$_z$C$_y$F$_{2y+1}$, where q is an integer of 1 to about 6, x is independently an integer of 1 to about 10 for each (C$_x$F$_{2x}$O), y is an integer of 1 to about 8, and z is an integer of 1 to about 5;

with the proviso that there are at least 3 in-chain atoms between said central core structure G and at least one said chiral center of R*.

26. A mixture of liquid crystal compounds comprising at least one fluorine-containing, chiral liquid crystal compound having a smectic mesophase or a latent smectic mesophase, the compound comprising (a) a chiral fluorochemical terminal portion comprising (i) at least one chiral center, which can optionally be heteroatom-substituted; (ii) a terminal fluoroalkyl, fluoroether, perfluoroalkyl, or perfluoroether group; and (iii) an alkylene or fluoroalkylene group optionally containing at least one catenary ether oxygen atom; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core; and at least one other liquid crystal compound having at least one fluorinated terminal portion, wherein said other liquid crystal compound is a chiral or achiral, perfluoroether group-containing liquid crystal compound.

27. A liquid crystal device containing at least one fluorine-containing, chiral liquid crystal compound having a smectic mesophase or a latent smectic mesophase, the compound comprising (a) a chiral fluorochemical terminal portion comprising (i) at least one chiral center, which can optionally be heteroatom-substituted; (ii) a terminal fluoroalkyl, fluoroether, perfluoroalkyl, or perfluoroether group; and (iii) an alkylene or fluoroalkylene group optionally containing at least one catenary ether oxygen atom; (b) a chiral or achiral terminal portion consisting of a hydrocarbon or hydrocarbon ether group and, when chiral, comprising at least one chiral center, which can optionally be heteroatom-substituted; and (c) a central core connecting said terminal portions; said alkylene or fluoroalkylene group of said chiral fluorochemical terminal portion having at least 3 in-chain atoms and being located between said chiral center of said chiral fluorochemical terminal portion and said central core; and at least one other liquid crystal compound having at least one fluorinated terminal portion, wherein said other liquid crystal compound is a chiral or achiral, perfluoroether group-containing liquid crystal compound.

28. Chiral liquid crystal intermediate compounds represented by the following general formulas IV and VI:

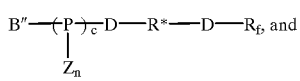
(IV)

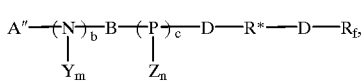
(VI)

where N and P are each independently selected from the group consisting of

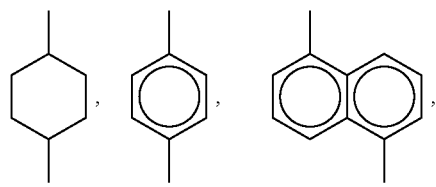

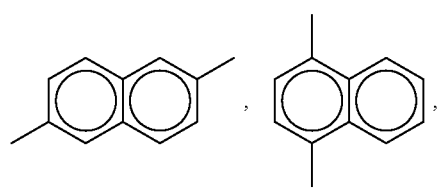

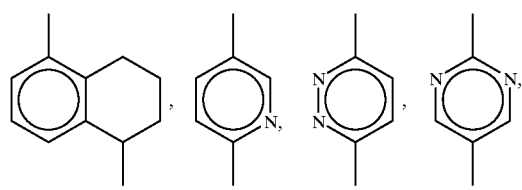

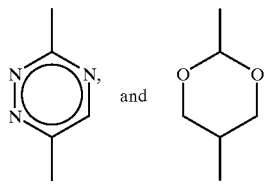

-continued

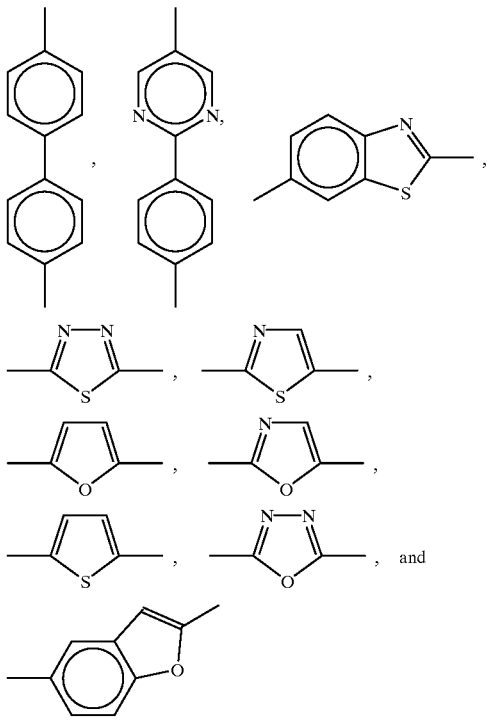

b and c are each independently zero or an integer of from 1 to 3;

B is non-directionally selected from the group consisting of a covalent bond, —C(=O)—O—, —C(=O)—S—, —C(=O)—Se—, —C(=O)—Te—, —(CH$_2$CH$_2$)$_k$— where k is 1 to 4, —CH=CH—, —C≡C—, —CH=N—, —CH$_2$—O—, —C(=O)—, and —O—;

each Y and Z are independently selected from the group consisting of —H, —Cl, —F, —Br, —I, —OH, —OCH$_3$, —CH$_3$, —CF$_3$, —OCF$_3$, —CN, and —NO$_2$;

each m and n are independently zero or an integer of 1 to 4;

each D is non-directionally and independently selected from the group consisting of a covalent bond, —C(=O)—O—C$_r$H$_{2r}$—, —O—C$_r$H$_{2r}$—, —O—(O=)C—C$_r$H$_{2r}$—, —C≡C—, —CH=CH—, —C(=O)—, —O—(C$_s$H$_{2s}$O)$_t$C$_r$H$_{2r}$—, —C$_r$H$_{2r}$—, —(C$_s$H$_{2s}$O)$_t$C$_r$H$_{2r}$—, —O—, —S—,

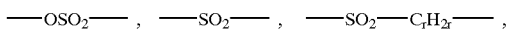

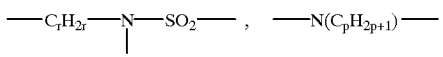

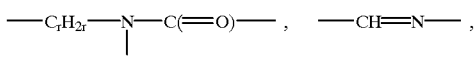

and combinations thereof, where one or more hydrogen atoms can optionally be replaced with fluorine, and where r and r' are independently integers of 0 to about 20, s is independently an integer of 1 to about 10 for each (C$_s$H$_{2s}$O), t is an integer of 1 to about 6, and p is an integer of 0 to about 4;

R* is a cyclic or acyclic chiral moiety containing at least one chiral center and selected from the group consisting of $-O-((C_{q'}H_{2q'-v'}-(R')_{v'})-O)_w-C_qH_{2q-v}-(R')_v$, $-((C_{q'}H_{2q'-v'}-(R')_{v'})-O)_w-C_qH_{2q-v}-(R')_v-$, $-C(=O)-O-C_qH_{2q-v}-(R')_v-$, $-O-(O=)C-C_qH_{2q-v}-(R')_v-$,

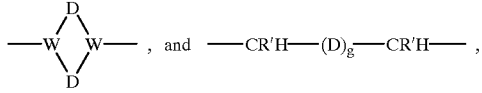, and $-CR'H-(D)_g-CR'H-$, where each R' is independently selected from the group consisting of $-Cl$, $-F$, $-CF_3$, $-NO_2$, $-CN$, $-H$, $-C_qH_{2q+1}$, $-O-(O=)C-C_qH_{2q+1}$, $-C(=O)-O-C_qH_{2q+1}$, $-Br$, $-OH$, and $-OC_qH_{2q+1}$; q' is independently an integer of 1 to about 20 for each $(C_qH_{2q'}-O)$; q is an integer of 1 to about 20; w is an integer of 0 to about 10; v is an integer of 0 to about 3; each v' is independently an integer of 0 to about 3; g is an integer of 1 to about 3; each D is independently and non-directionally selected from the group set forth for D above, with the proviso that the ring containing D has from about 3 to about 10 ring atoms; each W is independently selected from the group consisting of N, CR', and SiR'; and with the proviso that R* is chiral;

$R_f$ is perfluoroether;

with the proviso that there are at least 3 in-chain atoms between said central core structure

or

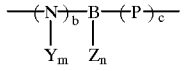

and at least one said chiral center of R*;

and A" and B" are selected from the group consisting of $-H$, $-Cl$, $-Br$, $-I$, $-OH$, $-COOH$, $-CH(CH_2OH)_2$, $-SH$, $-SeH$, $-TeH$, $-NH_2$, $-COCl$, $-CHO$, $-C\equiv CH$, dialkyl borane, $-CH=CH_2$, $-OSO_2R_f'''$, $-OSO_2CH_3$, $-OSO_2\text{-cyclo}(C_6H_4)-CH_3$, $-CH_2COOH$, $-NH(C=O)OC_qH_{2q+1}$, $-NCO$, and $-CH(C(O)O-C_qH_{2q+1})_2$, where $R_f'''$ is a perfluoroalkyl group having from 1 to about 10 carbon atoms and q is an integer of 0 to about 20.

29. The compounds of claim 25 wherein said s', said t', and said r" are each an integer of 1.

* * * * *

UNITED STATES PATENT AND TRADEMARK OFFICE
CERTIFICATE OF CORRECTION

PATENT NO. : 6,309,561 B1
DATED : October 30, 2001
INVENTOR(S) : Hasegawa, Masakazu It is certified that error appears in the above-identified patent and that said Letters Patent is hereby corrected as shown below:

Column 2
Line 30, delete "—$C_r,H_{2r'}$—," and insert in place thereof -- —$C_rH_{2r}$— --.
Line 32, after "—$OSO_2$—" insert therefore -- —$SO_2$—, --.

Column 5
Line 32, delete "—C≡—C—," and insert in place thereof -- —C≡C— --.
Line 47, delete "—$C_r,H_{2r},$—," and insert in place thereof -- —$C_rH_{2r}$— --
Line 50, after "—S—," insert -- —$OSO_2$—, --.

Column 5
Line 55, delete "—$NC_pH_{2p+1}$—," and insert in place thereof -- —$N(C_pH_{2p+1})$—, --.
Lines 55-56, delete " —$C_rH_{2r}$—N—$SO_2$— "
                                   |
                                $C_pH_{2p+1}$ Column 12
Line 66, after the word "Scheme" insert therefore --1 --.

Column 14
Line 38, after the word "as" delete "in".
Line 41, delete "$BF_3.Et_2O$" and insert in place thereof -- $BF_3•Et_2O$ --.
Line 64, delete "$BF_3.Et_2O$" and insert in place thereof -- $BF_3•Et_2O$ --.

Column 15
Line 22, delete "$BF_3•Et_2O$" and insert in place thereof -- $BF_3.Et_2O$ --.

Column 19
Line 19, delete "$BF_3.THF$" and insert in place thereof -- $BF_3•THF$ --.

Column 54
Example No. 110, delete "4.5" and insert in place thereof -- -4.5 --.

Column 77
Example No. 188, delete "34.4" and insert in place thereof 84.4, and delete "<--47" and insert in place thereof -- <-47 --, and delete "47" and insert in place thereof -- <47 --.

Column 86
Example No. 217, after "$F_4$" insert -- O --.

UNITED STATES PATENT AND TRADEMARK OFFICE
CERTIFICATE OF CORRECTION

PATENT NO.    : 6,309,561 B1
DATED         : October 30, 2001
INVENTOR(S)   : Hasegawa, Masakazu It is certified that error appears in the above-identified patent and that said Letters Patent is hereby corrected as shown below:

Column 88
Table 2, in the heading, delete "(mPa.s)" and insert in place thereof -- (mPa•s) --.
Table 2, Example No. 220, line 4, delete "40.0" and insert in place thereof -- -40.0 --.
Table 2, Example No. 221, line 4, delete "40.5" and insert in place thereof -- -40.5 --.
Table 2, Example No. 222, line 4, delete "18.9" under the Response Time column and insert --18.9 -- under the Tilt Angle column.
Table 2, Example No. 223, line 5, delete "49.7" and insert in place thereof -- -49.7 --.
Table 2, Example No. 224, line 5, delete "49.2" and insert in place thereof -- -49.2 --.
Table 2, Example No. 225, line 3, delete "41.8" and insert in place thereof -- -21.8 --.
Table 2, Example No. 225, line 5, delete "42.0" and insert in place thereof -- -42.0 --.

Column 89
Table 2, in the heading, delete "(mPa.s)" and insert in place thereof -- (mPa•s) --.
Table 2, Example 228, delete "compoun4" and insert in place thereof -- compound --.
Table 2, Example 228, line 4, delete "40.2" and insert in place thereof -- -40.2 --.
Table 2, Example 228, line 5, delete "49.9" and insert in place thereof -- -49.9 --.
Table 2, Example 229, line 4, delete "40.3" and insert in place thereof -- -40.3 --.
Table 2, Example 231, line 1, delete "4.6" and insert in place thereof -- -4.6 --.
Table 2, Example 231, line 5, delete "40.0" and insert in place thereof -- -40.0 --.
Table 2, Example 232, line 3, delete "30.2" and insert in place thereof -- -30.2 --.
Table 2, Example 234, line 4, delete "A1.6" and insert in place thereof -- -41.6 --.
Table 2, Example 234, line 5, delete "-S 1.6" and insert in place thereof -- -51.6 --.
Table 2, Example 236, line 4, delete "40.0" and insert in place thereof -- -40.0 --.

Column 92
Table 3, line 18, delete "Exampie" and insert in place thereof -- Example --.
Line 38, delete "198.0" and insert in place thereof -- 98.0 --.
Line 39, delete "155.4" and insert in place thereof -- 55.4 --.
Table 4, in the heading, delete "(mPa.s)" and insert in place thereof -- (mPa•s) --.
Table 4, Example No. 238, line 4, delete "40" and insert in place thereof -- -40 --.
Table 4, Example No. 239, line 2, delete "40" and insert in place thereof -- -20 --.
Table 4, Example No. 239, line 4, delete "40" and insert in place thereof -- -40 --.

Column 93
Table 4, in the heading, delete "(mPa.s)" and insert in place thereof -- (mPa•s) --.
Line 65, delete the bracketed formulas.

UNITED STATES PATENT AND TRADEMARK OFFICE
CERTIFICATE OF CORRECTION

PATENT NO.    : 6,309,561 B1  
DATED         : October 30, 2001  
INVENTOR(S)   : Hasegawa, Masakazu Page 3 of 3

It is certified that error appears in the above-identified patent and that said Letters Patent is hereby corrected as shown below:

Column 97  
Line 1, insert the following formulas: -- —O—(($C_q,H_{2q'-v'}$)—(R')$_{v'}$)—O)$_w$—$C_qH_{2q-v}$—(R')v—, —(($C_{q'}H_{2q'v'}$—(R')$_{v'}$)—O)$_w$—$C_qH_{2q-v}$—(R')v—, —C(=O)—O—$C_qH_{2q-v}$—(R')v—, —O—(O=)C—$C_qH_{2q-v}$—(R')v—, --.  
Line 38, delete the formula and insert in place thereof -- —R"—(O)$_j$—G—D'—R*($C_s$,$H_{2s}$.O)$_{t'}C_{r''}H_{2r''}$—$R_f$ --.

Column 98  
Lines 4-5, delete the formula and insert in place thereof -- —$C_qH_{2q-v}$—(R')$_v$— --.  
Line 19, before "5" insert the word -- about --.  
Line 53, delete "hydrogene" and insert in place thereof -- hydrogen --.  
Line 56, delete "($C_sH_{2s}$O," and insert in place thereof -- ($C_sH_{2s}$O), --.  
Line 65, before the word "mixture" insert -- A --.

Column 99  
Line 4, after the word "claim" insert -- 15 --.

Column 100  
Line 7, delete "8" and insert in place thereof -- q --.  
Line 53, delete the bracketed formulas.

Signed and Sealed this

Eighteenth Day of June, 2002

*Attest:*

*Attesting Officer*

JAMES E. ROGAN  
*Director of the United States Patent and Trademark Office*